(12) United States Patent
Konno et al.

(10) Patent No.: US 9,114,088 B2
(45) Date of Patent: Aug. 25, 2015

(54) COSMETIC PREPARATION FOR HAIR AND METHOD FOR APPLICATION THEREOF

(75) Inventors: Yoshihiro Konno, Nagakute (JP); Yosuke Kobayashi, Nagakute (JP)

(73) Assignee: HOYU CO., LTD., Nagoya-shi, Aichi (JP)

( * ) Notice: Subject to any disclaimer, the term of this patent is extended or adjusted under 35 U.S.C. 154(b) by 0 days.

(21) Appl. No.: 13/502,683

(22) PCT Filed: Nov. 11, 2010

(86) PCT No.: PCT/JP2010/070112
§ 371 (c)(1),
(2), (4) Date: Apr. 18, 2012

(87) PCT Pub. No.: WO2011/059027
PCT Pub. Date: May 19, 2011

(65) Prior Publication Data
US 2012/0207689 A1    Aug. 16, 2012

(30) Foreign Application Priority Data

Nov. 13, 2009    (JP) ................. 2009-260490

(51) Int. Cl.
*A61Q 5/08*    (2006.01)
*A61Q 5/10*    (2006.01)
*A61K 8/41*    (2006.01)
*A61K 8/04*    (2006.01)
*A61K 8/22*    (2006.01)

(52) U.S. Cl.
CPC ................. *A61K 8/416* (2013.01); *A61K 8/046* (2013.01); *A61K 8/22* (2013.01); *A61Q 5/08* (2013.01); *A61Q 5/10* (2013.01); *A61K 2800/88* (2013.01); *A61K 2800/882* (2013.01)

(58) Field of Classification Search
None
See application file for complete search history.

(56) References Cited

U.S. PATENT DOCUMENTS

| 8,388,696 | B2 * | 3/2013 | Fujinuma et al. | ................. 8/405 |
| 2003/0226217 | A1 * | 12/2003 | Bowes et al. | ..................... 8/405 |
| 2004/0213752 | A1 | 10/2004 | Fujinuma et al. | |
| 2006/0254001 | A1 | 11/2006 | Hoeffkes et al. | |
| 2010/0126522 | A1 | 5/2010 | Fujinuma et al. | |
| 2010/0126523 | A1 | 5/2010 | Fujinuma et al. | |
| 2012/0186598 | A1 | 7/2012 | Fujinuma et al. | |

FOREIGN PATENT DOCUMENTS

| EP | 0399157 A2 | 11/1990 |
| JP | 63-174917 A | 7/1988 |
| JP | 3-287521 A | 12/1991 |
| JP | H04-501422 A | 3/1992 |
| JP | H08-157343 A | 6/1996 |
| JP | 9-136818 A | 5/1997 |
| JP | 2004-091431 A | 3/2004 |
| JP | 2004-115410 A | 4/2004 |
| JP | 2007-503409 A | 2/2007 |
| JP | 2008-291020 A | 4/2008 |
| JP | 2008-208120 A | 9/2008 |
| JP | 2009-051856 A | 3/2009 |
| JP | 2009-154884 A | 7/2009 |
| JP | 2009-161491 A | 7/2009 |
| JP | 2006-342125 A | 12/2009 |
| TW | 200901910 A | 1/2009 |
| WO | WO 2008/136441 A1 | 11/2008 |

OTHER PUBLICATIONS

Official Action corresponding to Chinese Patent Application No. 201080049918.5 dated Sep. 12, 2013.
International Search Report (Form PCT/ISA/210) issued in International Patent Application No. PCT/JP2010/070112 on Jan. 18, 2011.
Official Action corresponding to Chinese Patent Application No. 201080049918.5 dated Mar. 4, 2013.
International Search Report (Form PCT/ISA/210) issued in International Patent Application No. PCT/JP2010/070112 on Jan. 11, 2011.
Official Action corresponding to Japanese Patent Application No. 2009-260490 dated Nov. 13, 2013.
Official Action corresponding to Korean Patent Application No. 10-2012-7014709 dated Nov. 8, 2013.
International Preliminary Report on Patentability—Chapter I of Patent Cooperation Treaty (Form PCT/IB/373) corresponding to International Patent Application No. PCT/JP2010/070112 dated Jun. 12, 2012 (including English Translation of Written Opinion of the International Searching Authority (Form PCT/ISA/237)).
Taiwanese Office Action for Application No. 099139085 dated Jul. 1, 2014.
Colombian Office Action for Application No. PCT/JP2010/070112 dated Nov. 11, 2010.
Korean Office Action for Application No. 10 2012/7014709 dated May 20, 2014.
Mexican Office Action for Application No. MX/a/2012/005561 dated Jul. 4, 2014.
Chinese Notification of the Decision of Rejection for Application No. 2010800499185 dated Apr. 30, 2014.
Colombian Office Action for Application No. 12-92123-2 dated May 19, 2014.
Korean Notice to File a Response for Application No. 10-2012-7014709 dated May 20, 2014.
Japanese Notification of the Decision of Rejection for Application No. 2009-260-490 dated Jun. 3, 2014.
Taiwanese Office Action for Application No. 02-23765349 dated Jul. 1, 2014.
Qingzhe, Jiang, et al. Surfactant science and application. China Petrochemical Press, First Edition, 2006. 5, p. 173-177; 298-300.

(Continued)

*Primary Examiner* — Jyothsna Venkat
(74) *Attorney, Agent, or Firm* — Jenkins, Wilson, Taylor & Hunt, P.A.

(57) ABSTRACT

A hair cosmetic composition to be used for dyeing or bleaching hair or for removing dye from hair is applied to the hair in a foamy form obtained by mixing a powdery agent and a liquid agent and foaming the mixture by shaking.

5 Claims, 2 Drawing Sheets

(56) References Cited

OTHER PUBLICATIONS

Colombian Office Action for Application No. 12-092123 dated Sep. 23, 2014.
Korean Office Action for Application No. 10 2012/7014709 dated Nov. 27, 2014.
Korean Office Action for Application No. 10-2012-7014709 dated Mar. 23, 2015.
Mexiacn Office Action for Application No. MX/a/2012/005561 dated Feb. 6, 2015.
Chinese Office Action for Application No. 201080049918.5 dated Apr. 22, 2015.

* cited by examiner

COSMETIC PREPARATION FOR HAIR AND METHOD FOR APPLICATION THEREOF

CROSS-REFERENCE TO RELATED APPLICATIONS

This application is filed under the provisions of 35 U.S.C. §371 and claims the priority of International Patent Application No. PCT/JP2010/070112 filed on Nov. 11, 2010, and of Japanese Patent Application No. 2009-260490 filed on Nov. 13, 2009. The disclosures of the foregoing international patent application and Japanese patent application are hereby incorporated by reference herein in their respective entireties.

TECHNICAL FIELD

The present invention relates to a hair cosmetic composition that is constituted as a hair dye or a hair bleach/hair dye remover and is applied to hair in a foamy form, and to a method for using the hair cosmetic composition. More specifically, the present invention relates to a hair cosmetic composition that can be mixed and foamed easily and can be retained favorably in a foamy form on hair.

BACKGROUND ART

For example, hair cosmetic compositions whose form in use is a foamy form, comprising a first agent containing an alkali agent and a second agent containing an oxidizing agent are known as hair cosmetic compositions used for dyeing or bleaching hair or for removing dye from hair. Such hair cosmetic compositions used in a foamy form are characterized by being less likely to drip, being easily applied to hair, and offering favorable impression from use, compared with those used in a liquid form. Conventional hair cosmetic compositions are disclosed in, for example, Patent Documents 1 to 3.

Patent Document 1 discloses an aerosol-type foamy oxidation hair dye composition, which is prepared in a foamy form in use using a propellant such as LPG. Patent Document 2 discloses a two-part composition for dyeing or bleaching hair, which is prepared in a foamy form in use using a squeeze foamer comprising a flexible container of synthetic resin, a dip tube for suction, and foam discharging means. Patent Document 3 discloses that a hair cosmetic composition in a foamy form is formed by shaking a squeeze-type foam discharging container containing a solution containing first and second agents to thereby mix air into the solution such that the solution is foamed, and by squeezing it through foam homogenizing means made of a net or a porous material.

PRIOR ART DOCUMENTS

Patent Document 1: Japanese. Laid-Open Patent Publication No. 09-136818
Patent Document 2 Japanese Laid-Open Patent Publication No. 2008-291020
Patent Document 3: Japanese Laid-Open Patent Publication No. 2009-154884

SUMMARY OF THE INVENTION

Problems that the Invention is to Solve

However, an aerosol-type foamy oxidation hair dye composition disclosed in Patent Document 1 is disadvantageous in disposal, because it is mainly packed into cans.

A two-part composition for dyeing or bleaching hair disclosed in Patent Document 2 tends to cause poor mixing and requires carefully performing discharge procedures, because a mixture of two agents is discharged without foaming. This problem is particularly remarkable in the case of mixing of a powdery agent and a liquid agent and is responsible for reduced operability.

A foamy hair cosmetic composition disclosed in Patent Document 3 requires squeezing a container relatively hard for discharging large bubbles through foam homogenizing means immediately after shaking and thus has an operability problem. The power required for squeezing may be reduced by decreasing the viscosity of the foam. In this case, the foamy hair cosmetic composition has the problem that it tends to rapidly drip after being applied to hair and is not favorably retained on hair.

The present invention is based on the findings obtained by the present inventors as a result of diligent studies that a foamy hair cosmetic composition obtained by mixing a powdery agent and a liquid agent and foaming the mixture by shaking has small bubbles. Such small bubbles eliminate the need for using foam homogenizing means. Thus, the mixing and foaming of the hair cosmetic composition can be performed easily. Moreover, it has also been demonstrated that such a foamy hair cosmetic composition is favorably retained on hair.

An objective of the present invention is to provide a hair cosmetic composition that can be mixed and foamed easily and can be retained favorably in a foamy form on hair, and a method for using the hair cosmetic composition.

Means for Solving the Problems

To achieve the above objective, one aspect of the present invention provides a hair cosmetic composition constituted as a hair dye or a hair bleach/hair dye remover comprising a plurality of agents, wherein the hair cosmetic composition is applied to hair in a foamy form obtained by mixing a powdery agent and a liquid agent and foaming the mixture by shaking.

A hair cosmetic composition according to the above aspect may contain an amphoteric surfactant or a cationic surfactant.

When a hair cosmetic composition according to the above aspect further contains an anionic surfactant in addition to a cationic surfactant, it is preferred that the hair cosmetic composition should be constituted such that in use the anionic surfactant comes into contact with the cationic surfactant in the presence of a solvent.

It is preferred that the cationic surfactant should contain an ammonium cationic surfactant having an alkyl group with 16 or more and 22 or less carbon atoms and an ammonium cationic surfactant having an alkyl group with 10 or more and less than 16 carbon atoms.

When a hair cosmetic composition according to the above aspect contains a nonionic polymer, it is preferred that the nonionic polymer should be incorporated in the powdery agent.

When a hair cosmetic composition according to the above aspect contains a thickener, it is preferred that the thickener should be incorporated in the powdery agent.

A hair cosmetic composition according to the above aspect may comprise a powdery first agent containing an alkali agent and a liquid second agent containing hydrogen peroxide as an oxidizing agent.

The second agent may further contain an amphoteric surfactant and a cationic polymer.

A hair cosmetic composition according to the above aspect may further contain an inorganic salt of alkali metal.

The second agent may further contain phenoxyethanol and at least one selected from benzoic acid and benzoates.

It is preferred that the alkali agent should be a carbonate. When a hair cosmetic composition according to the above aspect further contains 1 to 5% by mass of a chelating agent, it is preferred that the mass ratio of the content of the carbonate in the hair cosmetic composition to that of the chelating agent in the hair cosmetic composition should be 0.02 to 6.5.

Another aspect of the present invention provides a method for using a hair cosmetic composition according to the above aspect, comprising the steps of: forming the hair cosmetic composition in a foamy form by mixing a powdery agent and a liquid agent in the hair cosmetic composition and foaming the mixture by shaking; and applying the obtained hair cosmetic composition in a foamy form to hair by hand.

Effects of the Invention

The present invention provides a hair cosmetic composition that can be mixed and foamed easily and can be retained favorably in a foamy form on hair, and a method for using the hair cosmetic composition.

BRIEF DESCRIPTION OF THE DRAWINGS

FIG. 1(a) is a diagram showing a container containing first and second agents of the hair bleach hair dye remover before use. FIG. 1(b) is a diagram showing the manner of adding the first and second agents to a main body of the container. FIG. 1(c) is a diagram showing the manner of attaching a lid to the main body of the container and shaking the container up and down. FIG. 1(d) is a diagram showing the removal of the lid from the main body of the container for directly taking a foamy hair bleach/hair dye remover out of the main body of the container by hand and applying it to hair.

MODE FOR CARRYING OUT THE INVENTION

First Embodiment

Figure 1:
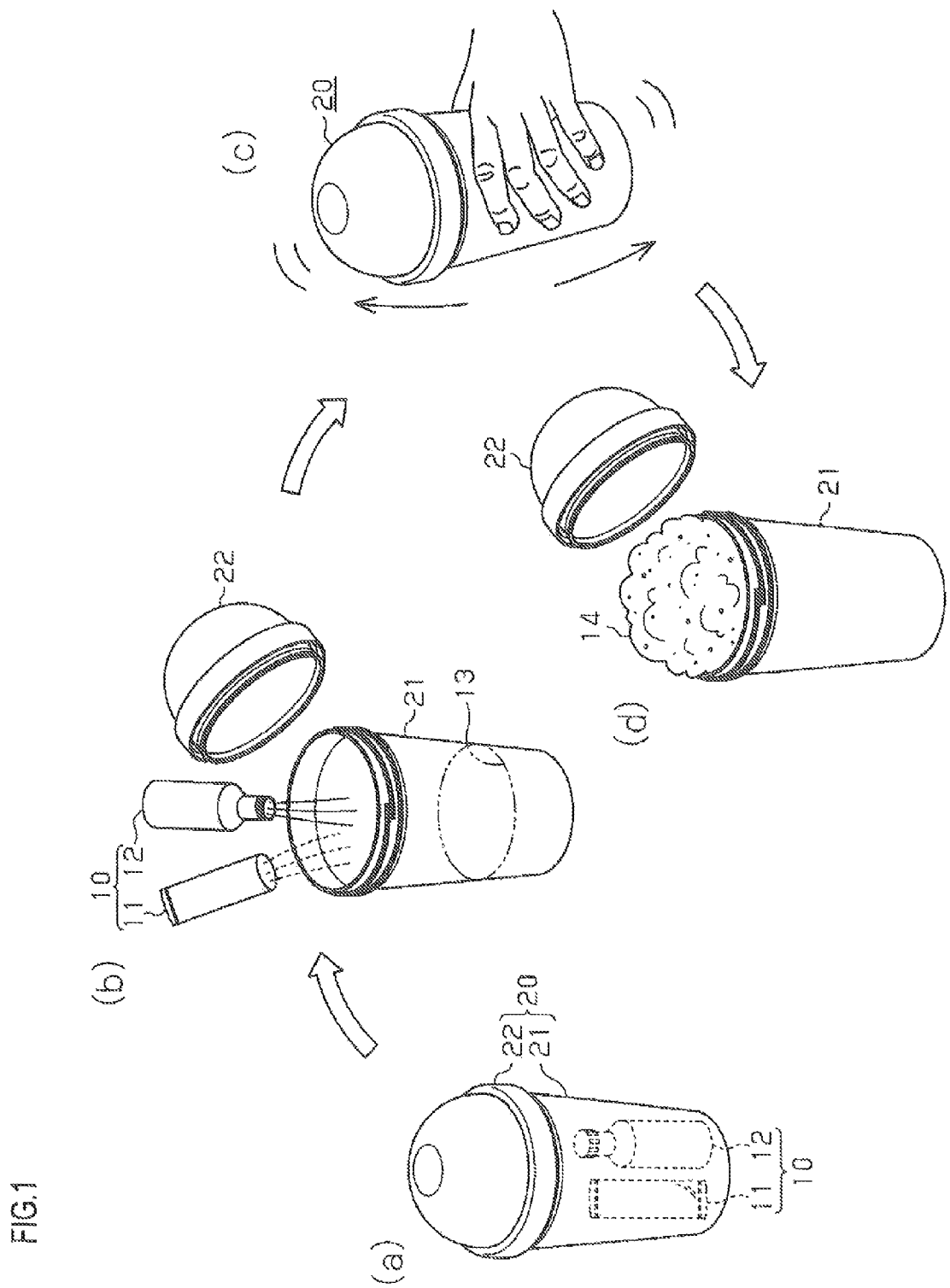
FIGS. 1(a) to 1(d) are diagrams illustrating a method for using a hair cosmetic comprising a two-part hair bleach/hair dye remover according to one embodiment of the present invention. More specifically.

Hereinafter, a first embodiment of the present invention will be described. A hair cosmetic composition according to the first embodiment is a two-part hair bleach/hair dye remover or a three-part hair bleach/hair dye remover.
<Two-Part Hair Bleach/Hair Dye Remover>

The two-part hair bleach/hair dye remover comprises, for example, a powdery first agent containing at least an alkali agent (hereinafter, also referred to as Component F) and a liquid second agent containing at least an oxidizing agent. This hair bleach/hair dye remover is prepared in a foamy form by mixing the first and second agents and foaming the mixture by shaking and then applied to hair for bleaching hair or removing dye from hair.
<First Agent in Two-Part Hair Bleach Hair Dye Remover>

In addition to the alkali agent as Component F, the first agent further contains, for example, an anionic surfactant (hereinafter, also referred to as Component C), a nonionic polymer (hereinafter, also referred to as Component D), a thickener (hereinafter, also referred to as Component E), and a chelating agent (hereinafter, also referred to as Component L).

The alkali agent has the function of improving hair bleaching or hair dye removing effects by promoting the action of the oxidizing agent contained in the second agent. It is preferred that the alkali agent used should be in a solid state at 25° C. (room temperature). Examples of such an alkali agent include silicate, carbonate (hereinafter, also referred to as Component f-1), metasilicate, sulfate, chloride, and phosphate.

Examples of the silicate include sodium silicate, potassium silicate, and magnesium silicate. The carbonate as Component f-1 also encompasses bicarbonate. Thus, examples of the carbonate include sodium carbonate, magnesium carbonate, ammonium carbonate, sodium bicarbonate, and ammonium bicarbonate. Examples of the metasilicate include sodium metasilicate and potassium metasilicate. Examples of the sulfate include ammonium sulfate. Examples of the chloride include ammonium chloride. Examples of the phosphate include primary ammonium phosphate and secondary ammonium phosphate.

Among these specific examples of the alkali agent, the carbonate is particularly preferable. When the carbonate is used as the alkali agent, the easiness of mixing and foaming of the hair bleach/hair dye remover is improved, and the retainability of the foamy hair bleach/hair dye remover on hair is improved. Furthermore, the generation of ammonia odor from the hair bleach/hair dye remover in use can be suppressed. Moreover, non-uniform lightness in hair after treatment with the hair bleach/hair dye remover can also be suppressed, because the carbonate does not generate heat of fusion when dissolved in a solvent such as water.

It is preferred that the alkali agent should be incorporated in an amount that allows the pH of the mixture of the first and second agents, i.e., the hair bleach/hair dye remover in use, to be in the range of 7 to 12. When the pH of the mixture of the first and second agents is 7 or higher, the action of hydrogen peroxide (hereinafter, also referred to as Component G) contained as the oxidizing agent in the second agent can be promoted strongly. When the pH of the mixture of the first and second agents is 12 or lower, hair can be prevented from being damaged by the hair bleach/hair dye remover applied to the hair.

The anionic surfactant as Component C has the function of improving the easiness of mixing and foaming of the hair bleach/hair dye remover and the retainability of the foamy hair bleach/hair dye remover on hair. Therefore, the first agent preferably contains the anionic surfactant. The anionic surfactant may be incorporated in either of the first or second agent or may be incorporated in both of the first and second agents. Examples of the anionic surfactant include alkyl ether sulfate, alkyl sulfate, alkenyl ether sulfate, alkenyl sulfate, olefin sulfonate, alkane sulfonate, saturated or unsaturated fatty acid salt, alkyl or alkenyl ether carboxylate, α-sulfone fatty acid salt, N-acylamino acid surfactants, phosphoric acid mono- or di-ester surfactants, and sulfosuccinic acid ester. A counter ion for the anionic group in these surfactants may be any of, for example, a sodium ion, a potassium ion, and triethanolamine. More specific examples of the alkyl sulfate include sodium lauryl sulfate and sodium cetyl sulfate. Examples of the sulfosuccinic acid ester include disodium lauryl sulfosuccinate. Only one kind of the anionic surfactant may be used, or two or more kinds of the anionic surfactants may be used in combination.

The content of the anionic surfactant in the mixture of the first and second agents is preferably 0.1 to 10% by mass, and more preferably 0.5 to 5% by mass. When the content of the anionic surfactant fails within any of these ranges, the effect of improving the easiness of mixing and foaming of the hair bleach/hair dye remover and the retainability of the foamy hair bleach/hair dye remover on hair can be obtained favorably. Moreover, the dryness of hair after treatment with the hair bleach/hair dye remover can also be suppressed.

It is preferred that the anionic surfactant should come into contact with a cationic surfactant as Component B in the presence of a solvent in use of the hair bleach/hair dye remover. Therefore, for example, the anionic surfactant may be incorporated in any one of the first and second agents, while the cationic surfactant may be incorporated in the other agent. Alternatively, both of the anionic surfactant and the cationic surfactant may be incorporated in the first agent having a powdery form. In this case, the foamability of the hair bleach/hair dye remover is improved, and the durability of foam obtained by foaming is enhanced. This further improves the easiness of mixing and foaming of the hair bleach/hair dye remover and the retainability of the foamy hair bleach/hair dye remover on hair. Furthermore, it also has the advantage that the rate of onset of a thickening effect is accelerated during the mixing of the first and second agents, and that the viscosity stability of the hair bleach/hair dye remover is improved.

To further improve the durability of foam obtained by foaming, it is preferred that the content of the anionic surfactant in the mixture of the first and second agents should be 0.1 to 3.0% by mass, and more preferably 0.5 to 1.5% by mass. Moreover, it is preferred that the content of the cationic surfactant in the mixture of the first and second agents should be 0.1 to 5.0% by mass, more preferably 0.5 to 4.5% by mass, and even more preferably 0.5 to 2.0% by mass. Furthermore, it is preferred that the mass ratio of the content of the anionic surfactant in the mixture of the first and second agents to that of the cationic surfactant in the same mixture should be in the range of 0.25 to 3, more preferably 0.4 to 3, and even more preferably 0.8 to 2.

To further accelerate the rate of onset of the thickening effect during the mixing of the first and second agents and to further improve the viscosity stability of the hair bleach/hair dye remover, it is preferred that the content of the anionic surfactant in the mixture of the first and second agents should be 0.01 to 10% by mass, and more preferably 0.5 to 5% by mass. Moreover, it is preferred that the mass ratio of the content of the anionic surfactant in the mixture of the first and second agents to that of the cationic surfactant in the same mixture should be in the range of 0.1 to 20, more preferably 0.5 to 10, and even more preferably 1 to 7.

The nonionic polymer as Component D has the function of improving the easiness of mixing and foaming of the hair bleach/hair dye remover and the retainability of the foamy hair bleach/hair dye remover on hair. Moreover, it also has the function of improving the foam quality of the foamy hair bleach/hair dye remover, for example, the homogeneity or elasticity of foam. Therefore, the first agent preferably contains the nonionic polymer. The nonionic polymer may be incorporated in either of the first or second agent or may be incorporated in both of the first and second agents.

The nonionic polymer used may be a natural macromolecule or may be a semi-synthetic or synthetic macromolecule. A natural or semi-synthetic nonionic sugar is preferably used to further improve the easiness of mixing and foaming of the hair bleach/hair dye remover and the retainability of the foamy hair bleach/hair dye remover on hair and to further improve the homogeneity and elasticity of the foamy hair bleach/hair dye remover. Oligosaccharide and polysaccharide having an α-glucose compound such as α-glucose or an α-glucose derivative as a constituent unit are particularly preferably used. Examples of the oligosaccharide and polysaccharide having an α-glucose compound as a constituent unit include starch, hydrolyzed starch, starch derivatives, dextran, dextrin, and cyclodextrin. Other examples of the nonionic sugar include cellulose and agar. A low water-soluble, dispersible nonionic polymer (e.g., starch and cyclodextrin) is more preferably used than a high water-soluble nonionic polymer for the same reason as that for the natural or semi-synthetic nonionic sugar. Examples of the nonionic synthetic macromolecule include polyvinylcaprolactam, PVP, (vinylpyrrolidone/VA) copolymers, polyvinyl alcohol, polyvinyl butyral, and highly polymerized polyethylene glycol.

When two or more kinds of nonionic polymers are used in combination, the easiness of mixing and foaming of the hair bleach/hair dye remover and the retainability of the foamy hair bleach/hair dye remover on hair may be further improved, or the homogeneity and elasticity of the foamy hair bleach/hair dye remover may be further improved. Particularly, it is preferred that two or more kinds of dispersible nonionic polymers should be used in combination. It is more preferred that at least one of the dispersible nonionic polymers used in combination should be starch.

The content of the nonionic polymer in the mixture of the first and second agents is preferably 0.3 to 15% by mass, and more preferably 1 to 10% by mass. When the content of the nonionic polymer falls within any of these ranges, the effect of improving the easiness of mixing and foaming of the hair bleach/hair dye remover and the retainability of the foamy hair bleach/hair dye remover on hair can be obtained favorably. Moreover, the homogeneity and elasticity of the foamy hair bleach/hair dye remover are further improved.

When starch is incorporated as the nonionic polymer in the first agent having a powdery form, the rate of onset of a thickening effect is accelerated during the mixing of the first and second agents, and the viscosity stability of the hair bleach/hair dye remover is improved. Examples of the starch include starch of cereals, starch of tubers, starch of beans, starch of wild grasses, stem or trunk starch, and modified starches (processed starches) thereof. More specifically, corn starch, tapioca starch, potato starch, sweet potato starch, sago starch, and modified starches thereof can be used. The modified starches refer to those obtained by artificially changing the physical properties of starch by subjecting the starch to derivatization treatment (e.g., etherification, esterification, and grafting), decomposition treatment (e.g., roasting, enzymatic denaturation, oxidation, and acid treatment), or processing (e.g., gelatinization, granulation, and pore introduction). Only one kind of the starch may be used, or two or more kinds of the starches may be used in combination.

To further accelerate the rate of onset of the thickening effect during the mixing of the first and second agents and to further improve the viscosity stability of the hair bleach/hair dye remover, it is preferred that the content of the starch in the mixture of the first and second agents should be 0.1 to 20% by mass, and more preferably 2 to 10% by mass.

The thickener as Component E has the function of improving the easiness of mixing and foaming of the hair bleach/hair dye remover and the retainability of the foamy hair bleach/hair dye remover on hair. Moreover, it also has the function of imparting appropriate viscosity to the hair bleach/hair dye remover such that the hair bleach/hair dye remover is prevented from dripping from hair when applied to the hair. Therefore, the first agent preferably contains the thickener. The thickener may be incorporated in either of the first or second agent or may be incorporated in both of the first and second agents. Specific examples of the thickener include natural macromolecules, semi-synthetic macromolecules, synthetic macromolecules, and inorganic macromolecules.

Examples of the natural macromolecules include guar gum, locust bean gum, quince seeds, carrageenan, galactan, gum arabic, tragacanth gum, pectin, mannan, xanthan gum, succinoglucan, curdlan, hyaluronic acid, gelatin, casein, albumin, and collagen.

Examples of the semi-synthetic macromolecules include methylcellulose, ethylcellulose, hydroxyethylcellulose, hydroxypropylcellulose, hydroxypropylmethylcellulose, carboxymethylcellulose, sodium carboxymethylcellulose, methylhydroxypropylcellulose, alginic acid propylene glycol ester, and alginate.

Examples of the synthetic macromolecules include Polyvinylpyrrolidone, polyvinyl methyl ether, carboxyvinyl polymers, sodium polyacrylate, polyacrylamide, polyethylene oxide, ethylene oxide-propylene oxide block copolymers, and acrylic acid-alkyl acrylate copolymers. Moreover, a copolymer comprising half ester of itaconic acid and polyoxyethylene alkyl ether or ester of methacrylic acid and polyoxyethylene alkyl ether, and at least one monomer selected from acrylic acid, methacrylic acid, and alkyl esters thereof may be used.

Examples of the inorganic macromolecules include bentonite, magnesium aluminum silicate, Laponite, hectorite, and silicic acid anhydride.

Only one kind of the thickener may be used, or two or more kinds of the thickeners may be used in combination.

The content of the thickener in the mixture of the first and second agents preferably 0.1 to 20% by mass, and more preferably 1 to 5% by mass. When the content of the thickener falls within any of these ranges, the effect of improving the easiness of mixing and foaming of the hair bleach/hair dye remover and the retainability of the foamy hair bleach/hair dye remover on hair can be obtained favorably. Moreover, reduction in the applicability of the hair bleach/hair dye remover can also be suppressed.

For accelerating the rate of onset of the thickening effect during the mixing of the first and second agents and for improving the viscosity stability of the hair bleach hair dye remover, it is preferred that the content of the thickener in the mixture of the first and second agents should be 0.05 to 20% by mass, and more preferably 0.5 to 4% by mass. Moreover, it is preferred that the mass ratio of the content of the starch in the mixture of the first and second agents to that of the thickener in the same mixture should be 0.1 to 20, more preferably 1 to 7, and even more preferably 1 to 3. When this mass ratio falls within any of these ranges, the rate of onset of the thickening effect during the mixing of the first and second agents is further accelerated, and the viscosity stability of the hair bleach/hair dye remover is further improved.

The chelating agent as Component L has the function of improving the easiness of mixing and foaming of the hair bleach/hair dye remover and the retainability of the foamy hair bleach/hair dye remover on hair. The chelating agent also has the function of suppressing the roughness of hair that may be caused by using a carbonate as the alkali agent as Component F and the function of improving hair texture after treatment with the hair bleach/hair dye remover, i.e., the smoothness during finger combing. Therefore, the first agent preferably contains the chelating agent. The chelating agent may be incorporated in either of the first or second agent or may be incorporated in both of the first and second agents.

Examples of the chelating agent include edetic acid (ethylenediaminetetraacetic acid (EDTA)), ethylenediaminehydroxyethyltriacetic acid, dihydroxyethylethylenediaminediacetic acid, 1,3-propanediaminetetraacetic acid, diethylenetriaminepentaacetic acid, triethylenetetraminehexaacetic acid, nitrilotriacetic acid, hydroxyethyl iminodiacetic acid, L-aspartic acid-N,N-diacetic acid, aminotrimethylenephosphonic acid, hydroxyethanediphosphonic acid, salts thereof, derivatives thereof, and salts of the derivatives thereof. Only one kind of the chelating agent may be used, or two or more kinds of the chelating agents may be used in combination.

The content of the chelating agent in the mixture of the first and second agents is preferably 1 to 5% by mass, and more preferably 1 to 3% by mass. When the content of the chelating agent falls within any of these ranges, the effect of improving the easiness of mixing and foaming of the hair bleach/hair dye remover and the retainability of the foamy hair bleach/hair dye remover on hair can be obtained favorably. Moreover, hair texture after treatment with the hair bleach/hair dye remover can be further improved.

When a carbonate is used as the alkali agent as Component F, the mass ratio ((f-1)/L) of the content of the carbonate in the mixture of the first and second agents to that of the chelating agent in the same mixture is preferably 0.02 to 6.5, more preferably 0.5 to 4.5, and even more preferably 0.9 to 4.5. When this mass ratio falls within any of these ranges, the easiness of mixing and foaming of the hair bleach/hair dye remover and the retainability of the foamy hair bleach/hair dye remover on hair are more greatly improved. Moreover, reduction in hair texture after treatment with the hair bleach/hair dye remover that may be caused by a carbonate can be suppressed more strongly.

The first agent may further contain, if necessary, any of components other than the components described above, for example, oil components, polyhydric alcohols, additional surfactants other than the surfactants described above, sugars, antiseptics, stabilizers, pH adjusters, plant extracts, crude drug extracts, vitamins, perfumes, antioxidants, UV absorbers, oxidation aids, excipients, and additives.

The oil components play a role in moisturizing hair. Examples of the oil components include oil and fat, wax, higher alcohol, hydrocarbon, higher fatty acid, alkyl glyceryl ether, ester, and silicone.

Examples of the oil and fat include lanolin, olive oil, camellia oil, shea butter, almond oil, safflower oil, sunflower oil, soybean oil, cottonseed oil, sesame oil, corn oil, rapeseed oil, rice bran oil, rice germ oil, grape seed oil, avocado oil, macadamia nut oil, castor oil, coconut oil, and evening primrose oil.

Examples of the wax include bee wax, candelilla wax, carnauba wax, jojoba oil, and lanolin.

Examples of the higher alcohol include cetyl alcohol (cetanol), 2-hexyldecanol, stearyl alcohol, isostearyl alcohol, cetostearyl alcohol, oleyl alcohol, arachyl alcohol, behenyl alcohol, 2-octyldodecanol, lauryl alcohol, myristyl alcohol, decyltetradecanol, and lanolin alcohol.

Examples of the hydrocarbon include paraffin, olefin oligomers, polyisobutene, hydrogenated polyisobutene, mineral oil, squalane, polybutene, polyethylene, microcrystalline wax, and Vaseline.

Examples of the higher fatty acid include lauric acid, myristic acid, palmitic acid, stearic acid, behenic acid, isostearic acid, 12-hydroxystearic acid, oleic acid, and lanolin fatty acid.

Examples of the alkyl glyceryl ether include batyl alcohol, chimyl alcohol, selachyl alcohol, and isostearyl glyceryl ether.

Examples of the ester include diisopropyl adipate, isopropyl myristate, cetyl octanoate, sononyl isononanoate, octyldodecyl myristate, isopropyl palmitate, stearyl stearate, myristyl myristate, isotridecyl myristate, 2-ethylhexyl palmitate, octyldodecyl ricinoleate, fatty acid cholesteryl/lanosteryl having 10 to 30 carbon atoms, cetyl lactate, lanolin acetate, ethylene glycol di-2-ethylhexanoate, pentaerythritol fatty acid ester, dipentaerythritol fatty acid ester, cetyl caprate, glyceryl tricaprylate, diisostearyl malate, dioctyl succinate, and cetyl 2-ethylhexanoate.

Examples of the silicone include dimethylpolysiloxane (dimethicone), methylphenylpolysiloxane, decamethylcyclopentasiloxane, dodecamethylcyclohexasiloxane, terminal hydroxy group-modified dimethylpolysiloxane, highly polymerized silicone having an average polymerization degree of 650 to 10,000, polyether-modified silicone (e.g., (PEG/PPG/butylene/dimethicone) copolymers), amino-modified silicone, betaine-modified silicone, alkyl-modified silicone, alkoxy-modified silicone, mercapto-modified silicone, carboxy-modified silicone, and fluorine-modified silicone. Only one kind of the silicone may be used, or two or more kinds of silicones may be used in combination.

Examples of the polyhydric alcohols include glycol compounds and glycerin compounds. Examples of the glycol compounds include ethylene glycol, diethylene glycol, triethylene glycol, polyethylene glycol, propylene glycol, dipropylene glycol, isoprene glycol, and 1,3-butylene glycol. Examples of the glycerin compounds include glycerin, diglycerin, and polyglycerin.

The additional surfactants play a role as an emulsifier or solubilizer and are used to adjust the viscosity of the hair bleach/hair dye remover or to improve its viscosity stability. Moreover, it also has the function of improving the foamability of the hair bleach/hair dye remover and the function of improving the foam quality of the foamy hair bleach/hair dye remover, for example, the elasticity of foam. The surfactant used may be any of cationic surfactants, amphoteric surfactants, and nonionic surfactants. The cationic surfactant may be incorporated in the first agent without impairing the effect of the present invention.

Examples of the cationic surfactants include lauryl trimethyl ammonium chloride, cetyl trimethyl ammonium chloride, stearyl trimethyl ammonium chloride, alkyl trimethyl ammonium chloride, distearyl dimethyl ammonium chloride, cetyl trimethyl ammonium bromide, stearyl trimethyl ammonium bromide, lanolin fatty acid aminopropylethyldimethyl ammonium ethyl sulfate, stearyl trimethyl ammonium saccharine, cetyl trimethyl ammonium saccharine, methacryloyloxyethyl trimethyl ammonium chloride, and behenyl trimethyl ammonium methyl sulfate.

Examples of the amphoteric surfactants include fatty acid amidopropyldimethylaminoacetic acid betaine, alkyldimethylaminoacetic acid betaine, N-acylaminoethyl-N-2-hydroxyethyl aminocarboxylate, N-acylaminoethyl-N-carboxymethoxy ethyl aminocarboxylate, and hydroxyalkyl (C12-14) hydroxyethyl sarcosine.

Examples of the fatty acid amidopropyldimethylaminoacetic acid betaine include coconut oil fatty acid amidopropyldimethylaminoacetic acid betaine (also called cocamidopropyl betaine or coconut oil fatty acid amidopropyl betaine), palm oil fatty acid amidopropyldimethylaminoacetic acid betaine, lauric acid amidopropyldimethylaminoacetic acid betaine (also called lauramidopropyl betaine or amidopropyl betaine laurate), and ricinoleic acid amidopropyldimethylaminoacetic acid betaine. The fatty acid amidopropyldimethylaminoacetic acid betaine may be incorporated in the first agent in a salt form such as sodium salt, potassium salt, or triethanolamine salt.

Examples of the alkyldimethylaminoacetic acid betaine include decyldimethylaminoacetic acid betaine, lauryldimethylaminoacetic acid betaine, myristyldimethylaminoacetic acid betaine, cetyldimethylaminoacetic acid betaine, stearyldimethylaminoacetic acid betaine, oleyldimethylaminoacetic acid betaine, behenyldimethylaminoacetic acid betaine, and coconut oil alkyldimethylaminoacetic acid betaine. The alkyldimethylaminoacetic acid betaine may be incorporated in the first agent in a salt form such as sodium salt, potassium salt, or triethanolamine salt.

Examples of the N-acylaminoethyl-N-2-hydroxyethyl aminocarboxylate include sodium cocoamphoacetate (N-coconut oil fatty acid acyl-N'-carboxymethyl-N'-hydroxyethyl-ethylenediamine; also called 2-alkyl-N-carboxymethyl-N-hydroxyethylimidazolinium betaine), sodium cocoamphopropionate (N-coconut oil fatty acid acyl-N'-carboxyethyl-N'-hydroxyethylethylenediamine), sodium lauroamphoacetate (N-lauroyl-N'-carboxymethyl-N'-hydroxyethylethylenediamine), sodium olive amphoacetate, sodium cocoa butter amphoacetate, sodium sesame amphoacetate, sodium sweet almond amphoacetate, stearoamphoacetate, sodium palm amphoacetate, sodium peanut amphoacetate, sodium sunflower seed amphoacetate, and sodium cottonseed amphoacetate.

Examples of the N-acylaminoethyl-N-carboxymethoxy ethyl aminocarboxylate include sodium cocoamphodiacetate, sodium cocoamphodipropionate, and sodium lauroamphodiacetate.

Specific examples of the nonionic surfactants include ether nonionic surfactants and ester nonionic surfactants.

Specific examples of the ether nonionic surfactants include polyoxyethylene (hereinafter, referred to as POE) cetyl ether (Ceteth), POE stearyl ether (Steareth), POE behenyl ether, POE oleyl ether (Oleth), POE lauryl ether (Laureth), POE octyldodecyl ether, POE hexyldecyl ether, POE isostearyl ether, POE nonylphenyl ether, and POE octylphenyl ether.

Specific examples of the ester nonionic surfactants include POE sorbitan monooleate, POE sorbitan monostearate, POE sorbitan monopalmitate, POE sorbitan monolaurate, POE sorbitan trioleate, POE glycerin monostearate, POE glycerin monomyristate, POE sorbitol tetraoleate, POE sorbitol hexastearate, POE sorbitol monolaurate, POE sorbitol bee wax, polyethylene glycol monooleate, polyethylene glycol monostearate, polyethylene glycol monolaurate, lipophilic glycerin monooleate, lipophilic glycerin monostearate, self-emulsifying glycerin monostearate, sorbitan monooleate, sorbitan sesquioleate, sorbitan trioleate, sorbitan monostearate, sorbitan monopalmitate, sorbitan monolaurate, sucrose fatty acid ester, decaglyceryl monolaurate, decaglyceryl monostearate, decaglyceryl monooleate, and decaglyceryl monomyristate.

Only one kind of the additional surfactant may be used, or two or more kinds of the additional surfactants may be used in combination.

For improving the foam quality of the foamy hair bleach/hair dye remover, it is preferred that the content (content in use) of the surfactant in the mixture of the first and second agents should be 1.5 to 10% by mass, more preferably 3 to 8% by mass, and even more preferably 3 to 5% by mass.

Examples of the sugars include sorbitol and maltose.

Examples of the antiseptics include paraben.

Examples of the stabilizers include phenacetin, 8-hydroxyquinoline, acetanilide, sodium pyrophosphate, barbituric acid, uric acid, and tannic acid.

Examples of the pH adjusters include citric acid, tartaric acid, lactic acid, malic acid, succinic acid, fumaric acid, maleic acid, pyrophosphoric acid, gluconic acid, glucuronic acid, benzoic acid, 2-amino-2-methyl-1,3-propanediol, and basic amino acids.

Examples of the antioxidants include ascorbic acid and sulfite.

Examples of the oxidizing aids include persulfates such as ammonium persulfate, potassium persulfate, and sodium persulfate. The oxidizing aids are used to further improve the hair bleaching or hair dye removing effects of the hair bleach/hair dye remover.

Examples of the excipients include sodium sulfate.

Examples of the additives include dispersants. Examples of the dispersants include metal salts of stearic acid such as calcium stearate and magnesium stearate, talc, crystalline cellulose, and low substituted hydroxypropylcellulose.

The first agent has a powdery form. The powdery form described herein conceptually encompasses a particulate form.

<Second Agent in Two-Part Hair Bleach/Hair Dye Remover>

In addition to the oxidizing agent, the second agent further contains, for example, an amphoteric surfactant (hereinafter, also referred to as Component A), a cationic surfactant (hereinafter, also referred to as Component B), a cationic polymer (hereinafter, also referred to as Component H), an inorganic salt of alkali metal (hereinafter, also referred to as Component I), phenoxyethanol (hereinafter, also referred to as Component J), and at least one selected from benzoic acid and benzoates (hereinafter, also referred to as Component K).

The amphoteric surfactant as Component A has the function of improving the easiness of mixing and foaming of the hair bleach/hair dye remover and the retainability of the foamy hair bleach/hair dye remover on hair. Moreover, it has the function of emulsifying the second agent for adjustment to appropriate viscosity or improvement in the viscosity stability, the function of enhancing the volume and fineness of foam obtained by the foaming of the mixture of the first and second agents, the function of quickly initiating foaming under non-aerosol conditions, and the function of improving hair texture after treatment with the hair bleach/hair dye remover in collaboration with the cationic polymer as Component H. Therefore, the second agent preferably contains the amphoteric surfactant. The amphoteric surfactant may be incorporated in either of the first or second agent or may be incorporated in both of the first and second agents. Examples of the amphoteric surfactant contained in the second agent include the same as those described above as specific examples of the amphoteric surfactant contained in the first agent. A betaine-based amphoteric surfactant is preferably used to stabilize the pH of the second agent. Only one kind of the amphoteric surfactant may be used, or two or more kinds of the amphoteric surfactants may be used in combination. Moreover, a commercially available amphoteric surfactant containing an inorganic salt of alkali metal may be used.

Examples of commercially available amphoteric surfactants containing an inorganic salt of alkali metal include OBAZOLINE CBA-30 (coconut oil fatty acid amidopropyl betaine; manufactured by Toho Chemical Industry Co., Ltd.), SOFTAZOLINE CPB (coconut oil fatty acid amidopropyl betaine; manufactured by Kawaken Fine Chemicals Co., Ltd.), RIKABION B-200 (coconut oil fatty acid amidopropyl betaine; manufactured by New Japan Chemical Co., Ltd.), OBAZOLINE LB (lauryldimethylaminoacetic acid betaine; manufactured by Toho Chemical Industry Co., Ltd.), and SOFTAZOLINE LPB (amidopropyl betaine laurate; manufactured by Kawaken Fine Chemicals Co., Ltd.). Examples of commercially available amphoteric surfactants containing no inorganic salt of alkali metal include TAIPOL SOFT AM-100N (coconut oil fatty acid amidopropyl betaine; manufactured by Taiko Oil Chemicals Co., Ltd.), AMOGEN CB-H (coconut oil fatty acid amidopropyl betaine; manufactured by Dai-Ichi Kogyo Seiyaku Co., Ltd.), OBAZOLINE LB-SF (lauryldimethylaminoacetic acid betaine; manufactured by Toho Chemical. Industry Co., Ltd.), SOFTAZOLINE CPB-R (coconut oil fatty acid amidopropyl betaine; manufactured by Kawaken Fine Chemicals Co., Ltd.), and SOFTAZOLINE LPB-R (amidopropyl betaine laurate; manufactured by Kawaken Fine Chemicals Co., Ltd.).

The content of the amphoteric surfactant in the mixture of the first and second agents is preferably 0.1 to 10% by mass, and more preferably 0.5 to 5% by mass. When the content of the amphoteric surfactant falls within any of these ranges, the effect of improving the easiness of mixing and foaming of the hair bleach/hair dye remover and the retainability of the foamy hair bleach/hair dye remover on hair can be obtained favorably. Moreover, the dryness of hair after treatment with the hair bleach/hair dye remover can be suppressed.

To further improve the foamability of the hair bleach/hair dye remover, it is preferred that the content of the amphoteric surfactant in the mixture of the first and second agents should be 0.5 to 10.0% by mass, and more preferably 1.5 to 4.0% by mass.

To further improve hair texture after treatment with the hair bleach/hair dye remover, it is preferred that the content of the amphoteric surfactant in the second agent should be 0.5 to 12% by mass, more preferably 1.5 to 10% by mass, and even more preferably 1.5 to 3.5% by mass.

The cationic surfactant as Component B has the function of improving the easiness of mixing and foaming of the hair bleach/hair dye remover and the retainability of the foamy hair bleach/hair dye remover on hair. Therefore, the second agent preferably contains the cationic surfactant. The anionic surfactant may be incorporated in the second agent without impairing the effect of the present invention. Examples of the cationic surfactant include the same as those described above as specific examples of the cationic surfactant contained in the first agent. Only one kind, of the cationic surfactant may be used, or two or more kinds of the cationic surfactants may be used in combination.

To further improve the easiness of mixing and foaming of the hair bleach/hair dye remover and the retainability of the foamy hair bleach/hair dye remover on hair, it is preferred that the cationic surfactant should contain an ammonium cationic surfactant having an alkyl group with 16 or more and 22 or less carbon atoms (hereinafter, also referred to as Component b-1) and an ammonium cationic surfactant having an alkyl group with 10 or more and less than 16 carbon atoms (hereinafter, also referred to as Component b-2). In this case, the foam quality of the foamy hair bleach/hair dye remover is also advantageously improved.

Examples of the ammonium cationic surfactant as Component b-1 include dimethyl ammonium cationic surfactants and trimethyl ammonium cationic surfactants. More specifically, for example, cetyl trimethyl ammonium chloride (cetrimonium chloride, C16), stearyl trimethyl ammonium chloride (steartrimonium chloride, C18), distearyl dimethyl ammonium chloride (C18), behenyl trimethyl aluminum chloride (behentrimonium chloride, C22), distearyl dimethyl ammonium chloride (distearyl dimonium chloride, C18), cetyl trimethyl ammonium bromide (C16), stearyl trimethyl ammonium bromide (C18), stearyl trimethyl ammonium saccharine (C18), cetyl trimethyl ammonium saccharine (C16), and behenyl trimethyl ammonium methyl sulfate (C22) can be used. Among them, trimethyl ammonium surfactants having an alkyl group with 16 or more carbon atoms are preferable, and cetyl trimethyl ammonium or a salt thereof is more preferable.

Examples of the ammonium cationic surfactant as Component b-2 include dimethyl ammonium cationic surfactants and trimethyl ammonium cationic surfactants. More specific examples thereof include compounds derived from those described above as specific examples of the ammonium cationic surfactant as Component b-1 by changing the number of carbon atoms in the alkyl group to 10 or more and less than 16. Among them, trimethyl ammonium cationic surfactants having an alkyl group with 10 or more and less than 16 carbon atoms are preferable. Trimethyl ammonium cationic surfactants having an alkyl group with 10 or more and 15 or less carbon atoms are more preferable. Trimethyl ammonium cationic surfactants having an alkyl group with 10 or more and 14 or less carbon atoms are even more preferable. Specific examples of the trimethyl ammonium cationic surfactants having an alkyl group with 10 or more and 14 or less carbon atoms include dodecyl trimethyl ammonium (C10), lauryl trimethyl ammonium (C12), myristyl trimethyl ammonium (C14), and salts thereof, preferably lauryl trimethyl ammonium (C12) and a salt thereof. In this context, the number of carbon atoms in the ammonium cationic surfactant refers to the number of carbon atoms in the principal chain of the alkyl group. For example, the number of carbon atoms in a double-chain cationic surfactant refers to the number of carbon atoms in an alkyl chain having the largest number of carbon atoms.

The content of the cationic surfactant in the mixture of the first and second agents is preferably 0.1 to 10% by mass, and more preferably 0.5 to 5% by mass. When the content of the cationic surfactant falls within any of these ranges, the effect of improving the easiness of mixing and foaming of the hair bleach/hair dye remover and the retainability of the foamy hair bleach/hair dye remover on hair can be obtained favorably. Moreover, the dryness of hair after treatment with the hair bleach/hair dye remover can also be suppressed.

To further improve the foam quality of the foamy hair bleach/hair dye remover and hair texture after treatment with the hair bleach/hair dye remover, it is preferred that the content of the ammonium cationic surfactant as Component b-1 in the mixture of the first and second agents should be 0.1 to 10% by mass, and more preferably 0.2 to 2% by mass. Moreover, it is preferred that the content of the ammonium cationic surfactant as Component b-2 in the mixture of the first and second agents should be 0.1 to 10% by mass, and more preferably 0.4 to 4% by mass. Moreover, it is preferred that the mass ratio of the content of the ammonium cationic surfactant as Component b-2 in the mixture of the first and second agents to that of the ammonium cationic surfactant as Component b-1 in the same mixture should be in the range of 0.4 to 5.

The cationic polymer as Component H has the function of improving the easiness of mixing and foaming of the hair bleach/hair dye remover and the retainability of the foamy hair bleach/hair dye remover on hair. Moreover, it also has the function of improving hair texture after treatment with the hair bleach/hair dye remover in collaboration with the amphoteric surfactant as Component A. Therefore, the second agent preferably contains the cationic polymer. The cationic polymer may be incorporated in either of the first or second agent or may be incorporated in both of the first and second agents.

For example, the cationic polymer may contain an amino or ammonium group in the polymer chain or may contain a diallyl quaternary ammonium salt as a constituent unit. Examples of the cationic polymer include cationized cellulose derivatives, cationic starch, cationized guar gum derivatives, diallyl quaternary ammonium salt-acrylamide copolymers, and quaternary polyvinylpyrrolidone derivatives. More specific examples thereof include dimethyl diallyl ammonium chloride-acrylamide copolymers, dimethyl diallyl ammonium chloride-acrylic acid copolymers, polydimethylmethylenepiperidinium chloride, and hydroxyethylcellulose dimethyl diallyl ammonium.

Among them, cationic polymers that are in a liquid state at 25° C. are preferably used to further improve hair texture after treatment with the hair bleach/hair dye remover. Examples of the cationic polymers that are in a liquid state at 25° C. include MERQUAT 550 (dimethyl diallyl ammonium chloride-acrylamide copolymer), MERQUAT 280, 295 (dimethyl diallyl ammonium chloride-acrylic acid copolymer), and MERQUAT 100 (polydimethylmethylenepiperidinium chloride). These commercially available cationic polymers are dissolved in a solvent and are thus good in miscibility with other components.

Also when a dimethyl diallyl ammonium chloride polymer, a dimethyl diallyl ammonium chloride-acrylamide copolymer, or a dimethyl diallyl ammonium chloride-acrylic acid copolymer is used as the cationic polymer, hair texture after treatment with the hair bleach/hair dye remover is further improved. Particularly, when a carbonate is used as the alkali agent as Component F, the roughness of hair after treatment with the hair bleach/hair dye remover that may be caused by the carbonate can be suppressed, as in the chelating agent as Component L.

The content of the cationic polymer in the mixture of the first and second agents is preferably 0.05 to 5% by mass, and more preferably 0.1 to 2% by mass. When the content of the cationic polymer falls within any of these ranges, the effect of improving the easiness of mixing and foaming of the hair bleach/hair dye remover and the retainability of the foamy hair bleach/hair dye remover on hair can be obtained favorably. Moreover, reduction in hair texture due to the stickiness of hair after treatment with the hair bleach, air dye remover can also be suppressed.

To further improve hair texture after treatment with the hair bleach/hair dye remover, it is preferred that the content of the cationic polymer in the second agent should be 0.01 to 5% by mass, and more preferably 0.1 to 4% by mass.

The inorganic salt of alkali metal as Component I has the function of improving the easiness of mixing and foaming of the hair bleach/hair dye remover and the retainability of the foamy hair bleach/hair dye remover on hair. Moreover, particularly when hydrogen peroxide is used as the oxidizing agent and the amphoteric surfactant is incorporated in the second agent, the inorganic salt of alkali metal also has the function of improving the stability of the hydrogen peroxide by stabilizing the pH of the second agent. Therefore, the second agent preferably contains the inorganic salt of alkali metal. The inorganic salt of alkali metal may be incorporated in either of the first or second agent or may be incorporated in both of the first and second agents.

Examples of the inorganic salt of alkali metal include chloride, sulfate, nitrate, and phosphate of alkali metal. The alkali metal may be, for example, sodium, potassium, or lithium. Thus, the inorganic salt of alkali metal may be, for example, sodium chloride, potassium chloride, sodium sulfate, or potassium sulfate. From the viewpoint of pH stability, it is preferred that the inorganic salt of alkali metal should be a neutral salt.

The content of the inorganic salt of alkali metal in the mixture of the first and second agents is preferably 0.05 to 5% by mass, and more preferably 0.1 to 2% by mass. When the content of the inorganic salt of alkali metal falls within any of these ranges, the effect of improving the easiness of mixing and foaming of the hair bleach/hair dye remover and the retainability of the foamy hair bleach/hair dye remover on hair can be obtained favorably.

For improving the pH stability of the second agent, it is preferred that the content of the inorganic salt of alkali metal in the second agent should be 0.01 to 5% by mass, more preferably 0.05 to 1.5% by mass, and even more preferably 0.25 to 1.25% by mass.

Likewise, for improving the pH stability of the second agent, it is preferred that the mass ratio (A/I) of the content of the amphoteric surfactant in the second agent to that of the inorganic salt of alkali metal in the second agent should be 1.5 to 50, more preferably 2 to 25, even more preferably 2 to 10, and most preferably 2.5 to 7.5.

To further improve the stability of hydrogen peroxide, it is preferred that the pH of the second agent should be 2 to 6, and more preferably 3 to 5.

Phenoxyethanol as Component J and at least one selected from benzoic acid and benzoates as Component K have the function of improving the easiness of mixing and foaming of the hair bleach/hair dye remover and the retainability of the foamy hair bleach/hair dye remover on hair. Moreover, when hydrogen peroxide is used as the oxidizing agent, they also have the function of improving the stability of hydrogen peroxide. Therefore, the second agent preferably contains the phenoxyethanol and at least one selected from benzoic acid and benzoates. Examples of the benzoates include sodium benzoate and potassium benzoate.

The content of phenoxyethanol in the mixture of the first and second agents is preferably 0.05 to 1% by mass, more preferably 0.15 to 1% by mass, and even more preferably 0.15 to 0.8% by mass. When the content of phenoxyethanol falls within any of these ranges, the effect of improving the easiness of mixing and foaming of the hair bleach/hair dye remover and the retainability of the foamy hair bleach/hair dye remover on hair can be obtained favorably. Moreover, the stability of hydrogen peroxide used as the oxidizing agent is further improved. Furthermore, the generation of odor derived from phenoxyethanol can be suppressed.

The content of at least one selected from benzoic acid and benzoates, i.e., the component K, in the mixture of the first and second agents is preferably 0.01 to 1% by mass, more preferably 0.1 to 1% by mass, and even more preferably 0.15 to 1% by mass. When the content of the component K falls within any of these ranges, the effect of improving the easiness of mixing and foaming of the hair bleach/hair dye remover and the retainability of the foamy hair bleach/hair dye remover on hair can be obtained favorably. Moreover, the stability of hydrogen peroxide used as the oxidizing agent is further improved. Furthermore, rise in the alkali level of the hair bleach/hair dye remover that is responsible for scalp stimulation when the hair bleach/hair dye remover is applied to hair, or reduction in the solubility of benzoic acid and benzoates can also be suppressed.

When the second agent contains hydrogen peroxide, it is preferred, for improving the stability of hydrogen peroxide by suppressing the decomposition of hydrogen peroxide, that the mass ratio (J/K) of the content of phenoxyethanol in the second agent to that of at least one selected from benzoic acid and benzoates in the second agent should be 0.2 to 2.5, and more preferably 0.2 to 1.0.

The oxidizing agents have the function of decolorizing melanin contained in hair. Examples of the oxidizing agent include hydrogen peroxide, urea peroxide, melamine peroxide, sodium percarbonate, potassium percarbonate, sodium perborate, potassium perborate, ammonium persulfate, sodium peroxide, potassium peroxide, magnesium peroxide, barium peroxide, calcium peroxide, strontium peroxide, hydrogen peroxide adducts of sulfate, hydrogen peroxide adducts of phosphate, and hydrogen peroxide adducts of pyrophosphate.

The content of the oxidizing agent in the second agent is preferably 0.1 to 15.0% by mass, more preferably 2.0 to 9.0% by mass, and most preferably 3.0 to 6.0% by mass. When the content of the oxidizing agent falls within any of these ranges, melanin in hair can be decolorized favorably without largely damaging the hair when the hair bleach/hair dye remover is applied to the hair.

When the second agent contains hydrogen peroxide as the oxidizing agent, it is preferred, for improving the stability of hydrogen peroxide, that the second agent should contain a stabilizer such as hydroxyethanediphosphonic acid and a salt thereof. Examples of the salt of hydroxyethanediphosphonic acid include tetrasodium hydroxyethanediphosphonate and disodium hydroxyethanediphosphonate.

The second agent may further contain components generally contained in the conventional hair bleach/hair dye remover without impairing the effect of each component in the second agent. For example, the components that may be contained in the first agent except for the alkali agent may be incorporated appropriately without impairing the effect of the present invention.

The second agent has a liquid form. The liquid form described herein conceptually encompasses gels, creams, and emulsions.

For example, any of water, ethanol, n-propanol, isopropanol, methyl cellosolve, ethyl cellosolve, methyl carbitol, ethyl carbitol, benzyl alcohol, phenethyl alcohol, γ-phenylpropyl alcohol, cinnamic alcohol, anise alcohol, p-methylbenzyl alcohol, α-dimethylphenethyl alcohol, α-phenylethanol, phenoxyethanol, phenoxyisopropanol, 2-benzyloxyethanol, N-alkylpyrrolidone, alkylene carbonate, and alkyl ether are used as solvents for dissolving each component in the second agent. Among them, water is preferably used because of its good ability to dissolve each component in the second agent. When water is used as a solvent, the content (content in use) of water in the mixture of the first and second agents is preferably 50% by mass or more, and more preferably 60% by mass or more.

The second agent is prepared by mixing the components of the second agent. The order in which the components of the second agent are mixed is not particularly limited. For improving the stability of hydrogen peroxide by improving the ph stability of the second agent by the action of the inorganic salt of alkali metal, it is preferred that before mixing of hydrogen peroxide and the amphoteric surfactant, the components of the second agent except for hydrogen peroxide should be mixed first to prepare an amphoteric surfactant-containing aqueous solution. It is preferred that the mixing of hydrogen peroxide and the amphoteric surfactant should be performed by mixing this amphoteric surfactant-containing aqueous solution with a hydrogen peroxide-containing aqueous solution.

The amphoteric surfactant-containing aqueous solution is prepared, for example, by mixing the amphoteric surfactant and water with all of other components, if any, except for hydrogen peroxide and the inorganic salt of alkali metal and then further mixing the inorganic salt of alkali metal therewith. All of the other components may be mixed with a mixture obtained by mixing the amphoteric surfactant and water with the inorganic salt of alkali, metal. Alternatively, the amphoteric surfactant and water may be mixed with a portion of the other components and then further mixed with the inorganic salt of alkali metal and the remaining portion of the other components in this order.

Alternatively, the amphoteric surfactant-containing aqueous solution can also be prepared by mixing the inorganic salt of alkali metal with all of other components, if any, except for hydrogen peroxide and the amphoteric surfactant and then further mixing the amphoteric surfactant therewith. All of the other components may be mixed with a mixture obtained by mixing the inorganic salt of alkali metal with the amphoteric surfactant. Alternatively, the inorganic salt of alkali metal may be mixed with a portion of the other components and then further mixed with the amphoteric surfactant and the remaining portion of the other components in this order.

The content of the amphoteric surfactant in the amphoteric surfactant-containing aqueous solution is preferably 10 to 50% by mass, more preferably 20 to 40% by mass, and even more preferably 30 to 40% by mass. When the content of the amphoteric surfactant is 13% by mass or more, the effect of improving the stability of hydrogen peroxide can be obtained favorably. When the content of the amphoteric surfactant is 50% by mass or less, the amphoteric surfactant can be prevented from being deposited.

The content of the inorganic salt of alkali metal in the amphoteric surfactant-containing aqueous solution is preferably 0.1 to 20% by mass, more preferably 0.5 to 15% by mass, even more preferably 2.5 to 12.5% by mass, and most preferably 3 to 10% by mass. When the content of the inorganic salt of alkali metal falls within any of these ranges, the effect of improving the stability of the hydrogen peroxide can be obtained favorably.

The mass ratio (A/I) of the content of the amphoteric surfactant in the amphoteric surfactant-containing aqueous solution to that of the inorganic salt of alkali metal in the amphoteric surfactant-containing aqueous solution is preferably 1.5 to 50, more preferably 2 to 25, even more preferably 2 to 10, and most preferably 2.5 to 7.5. When this mass ratio falls within any of these ranges, the stability of the hydrogen peroxide is further improved.

It is preferred that the amphoteric surfactant and the inorganic salt of alkali metal should be mixed with each other within their respective predetermined concentration ranges in the preparation of the amphoteric surfactant-containing aqueous solution.

For example, when the amphoteric surfactant is mixed with water and then the inorganic salt of alkali metal is added to the mixture, the amount of water added with respect to 1 part by mass of the amphoteric surfactant is preferably 0.5 to 4 parts by mass, and more preferably 1 to 3 parts by mass. If this amount of water added is less than 0.5 parts by mass, the solubility of the amphoteric surfactant might be reduced. If this amount of water added exceeds 4 parts by mass, the pH stability of the second agent, and by extension, the stability of the hydrogen peroxide, might be reduced as a result of the decreased concentration of the amphoteric surfactant in the amphoteric surfactant-containing aqueous solution.

Moreover, for example, when the inorganic salt of alkali metal is mixed with water and then the amphoteric surfactant is added to the mixture, the amount of water added with respect to 1 part by mass of the inorganic salt of alkali metal is preferably 5 to 30 parts by mass, and more preferably 10 to 20 parts by mass. If this amount of water added is less than 5 parts by mass, the solubility of the inorganic salt of alkali metal might be reduced. If this amount of water added exceeds 30 parts by mass, the pH stability of the second agent, and by extension, the stability of the hydrogen peroxide, might be reduced as a result of the decreased concentration of the inorganic salt of alkali metal in the amphoteric surfactant-containing aqueous solution.

The content of the hydrogen peroxide in the hydrogen peroxide-containing aqueous solution mixed with the amphoteric surfactant-containing aqueous solution in the preparation of the second agent is preferably 25 to 40% by mass or 30 to 35% by mass. If this content of the hydrogen peroxide is less than 25% by mass, the stability of the hydrogen peroxide in the second agent may be reduced. If this content of the hydrogen peroxide exceeds 40% by mass, such a hydrogen peroxide-containing aqueous solution is difficult to obtain as a commercially available product, and the rate of decomposition of the hydrogen peroxide might be increased during storage.

The hair bleach/hair dye remover is prepared in a foamy form by mixing the first and second agents and foaming the mixture by shaking and then applied in a necessary amount to hair by hand using thin-gloves or with a comb or brush.

<Three-Part Hair Bleach/Hair Dye Remover>

The three-part hair bleach/hair dye remover comprises, for example, a first agent containing an alkali agent, a second agent having the same composition as that of the second agent in the two-part hair bleach/hair dye remover, and a third agent having the same composition as that of the first agent in the two-part hair bleach/hair dye remover except that the alkali agent is omitted. This hair bleach/hair dye remover is prepared in a foamy form by mixing all of the first, second, and third agents and foaming the mixture by shaking and then applied to hair for bleaching hair or removing dye from hair. The three-part hair bleach/hair dye remover thus constituted has favorable storage stability.

Next, a hair cosmetic used for preparing a hair bleach/hair dye remover having a foamy form will be described with reference to FIGS. 1(*a*) to 2.

As shown in FIG. 1(*a*), the hair cosmetic comprises a hair bleach/hair dye remover 10 and a liquid-tight sealable container 20 as a foaming tool for shaking the hair bleach/hair dye remover 10. A first agent 11 and a second agent 12 in the hair bleach/hair dye remover 10 are individually packaged and contained in the container 20 for storage until use. The package forms of the first agent 11 and the second agent 12 are not particularly limited and may be, for example, any of bottle, pillow, and tube packages.

The container 20 is provided with a bottomed cylindrical main body 21 and a hemispherical lid 22 for sealing the opening of the main body 21. The main body 21 has a shape having the opening larger in diameter than the bottom. Moreover, the main body 21 has a curved inside surface.

The peripheral edge of the lid 22 flanged with a fitting portion, and this fitting portion is fitted to the opening of the main body 21. For the container 20 shown in FIG. 1(*a*), the fitting portion of the lid, 22 is fitted to the opening of the main body 21, and the lid 22 is turned such that the lid 22 is attached to the main body 21 in a liquid-tight manner.

The container 20 is formed such that it can contain the individually packaged first agent 11 and second agent Specifically, as shown in FIG. 1(*a*), the container 20 is used as an exterior package that stores together the first agent 11 and the second agent 12 until use of the hair bleach/hair dye remover 10. The container 20 not only contains the first agent 11 and the second agent 12 but may contain accessories such as gloves and instructions used in hair bleaching or hair dye removal treatment. From the viewpoint of weight reduction, it is preferred that the container 20 should be formed from a resin or paper provided with water resistance. Print can also be made on the outside surface of the main body 21, for example, using a shrink film.

In use, the lid 22 is first removed from the main body 21, and the individually packaged first agent 11 and second agent 12 are taken out of the main body 21. Next, the packages of the first agent 11 and the second agent 12 are opened. As shown in FIG. 1(b), the first agent 11 and the second agent 12 are put in the main body 21. As a result, the first agent 11 and the second agent 12 come into contact with each other in the main body 21 to obtain a mixture 13. Subsequently, as shown in FIG. 1(c), the lid 22 is attached to the main body 21, and the container 20 is shaken up and down. During this shaking, the mixing of the first agent 11 and the second agent 12 proceeds in the container 20, and air is mixed into the mixture 13 by shaking. The mixture 13 is foamed by thus shaking up the mixture 13 with air. Then, after the predetermined number of shakes of the container 20, the shaking is stopped to complete foaming. A foamy hair bleach/hair dye remover 14 thus obtained is directly taken out of the main body 21, for example, by hand, after removal of the lid 22 from the main body 21 as shown in FIG. 1(d), and applied to hair. This hair bleach/hair dye remover is prepared in a foamy form and can thus easily conform to hair without dripping. After the application of the hair bleach/hair dye remover to hair, hair bleaching or hair dye removal proceeds while the hair bleach/hair dye remover is left. After a lapse of the predetermined time, the hair is washed with water or hot water for washing off the hair bleach/hair dye remover on the hair to complete the hair bleaching or hair dye removal treatment.

Figure 2:
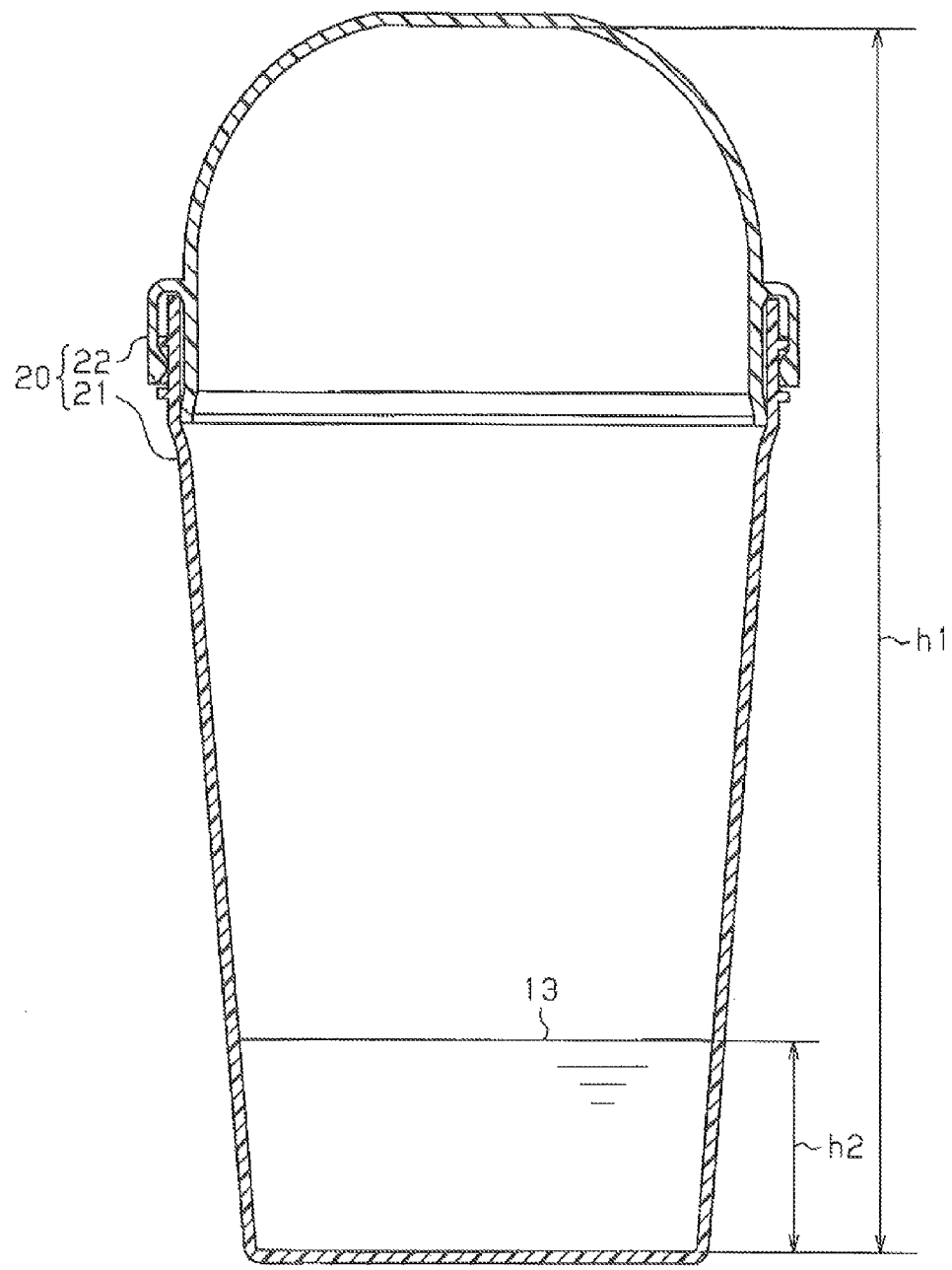
FIG. 2 is a cross-sectional view of the container of FIG. 1.

Since the main body 21 has a bottomed cylindrical shape having the opening larger in diameter than the bottom as shown in FIG. 2, the foamy hair bleach/hair dye remover 14 in the main body 21 is easily taken out, for example, by hand. Moreover, since the main body 21 has a curved inside surface, the foamy hair bleach/hair dye remover 14 in the main body 21 can be taken out easily even by hand without leaving a large portion.

It is preferred that the ratio (mL/g) of the interior content (mL) of the container 20 to the mass (g) of the mixture 13 of the first agent 11 and the second agent 12 of the hair bleach/hair dye remover should be in the range of 2 to 15. When this ratio is 2 or more, a vacant space in the container 20 containing the mixture 13 is easily secured, promoting the mixing of air into the mixture 13 by shaking. As a result, the number of shakes necessary for sufficiently foaming the mixture 13 can be reduced. However, if the ratio exceeds 15, the foamy hair bleach/hair dye remover 14 in the container 20 might be difficult to take out due to an increased redundant space in the container 20 after the completion of foaming.

The container 20 has a larger size in the height direction than that in the diameter direction. Therefore, the container 20 is easy to grasp. The height (represented by h1 in FIG. 2) of an accommodating portion in the container 20 is preferably 10 to 25 cm. When this height h1 is 10 cm or larger, the sufficient interior volume of the container 20 is easily secured. However, if the height h1 exceeds 25 cm, the container 20 might be difficult to handle due to its too large size.

It is preferred that the ratio (h1/h2) of the height h1 (cm) of the accommodating portion in the container 20 to the height (cm; represented by h2 in FIG. 2) of the mixture 13 of the hair bleach/hair dye remover before foaming in the container 20 should be in the range of 2 to 15. When this ratio is 2 or more, a vacant space in the container 20 containing the mixture 13 is easily secured, promoting the mixing of air into the mixture 13 by shaking. As a result, the number of shakes necessary for sufficiently foaming the mixture 13 can be reduced. However, if the h1/h2 ratio exceeds 15, the foamy hair bleach/hair dye remover 14 in the main body 21 might be difficult to take out due to an increased redundant space in the main body 21 after the completion of foaming.

This embodiment has the following advantages.

The two-part hair bleach/hair dye remover of this embodiment comprises a powdery first agent and a liquid second agent. A foamy hair bleach/hair dye remover obtained by mixing the first and second agents and foaming the mixture by shaking has small bubbles. In this case, the need of using foam homogenizing means as described in Patent Document 3 is eliminated. Thus, the hair bleach/hair dye remover can be mixed and foamed easily. Moreover, the foamy hair bleach/hair dye remover having small bubbles is favorably retained on hair.

The hair bleach/hair dye remover can be foamed easily to a high degree using the container 20 having a simple structure shown in FIGS. 1(a) to 2, without using a foamer container having a complicated structure or a propellant as in aerosols. Moreover, when this container 20 is used, the foamy hair bleach/hair dye remover can be obtained easily in relatively large amounts by single operation. Furthermore, the foaming procedures using this container 20 are easily performed without the need of skills and can thus be performed with enjoyment.

When the hair bleach/hair dye remover contains an amphoteric surfactant, the easiness of mixing and foaming of the hair bleach/hair dye remover is improved, and the retainability of the foamy hair bleach/hair dye remover on hair is improved. The amphoteric surfactant can also emulsify the second agent for adjustment to appropriate viscosity or improvement in viscosity stability.

When the hair bleach/hair dye remover contains a cationic surfactant, the easiness of mixing and foaming of the hair bleach/hair dye remover is improved, and the retainability of the foamy hair bleach/hair dye remover on hair is improved.

When the hair bleach/hair dye remover further contains an anionic surfactant in addition to the cationic surfactant, it is preferred that the hair bleach/hair dye remover should be constituted such that the anionic surfactant and the cationic surfactant come into contact with each other in the presence of a solvent in use of the hair bleach/hair dye remover. In this case, the easiness of mixing and foaming of the hair bleach/hair dye remover is further improved, and the retainability of the foamy hair bleach/hair dye remover on hair is also further improved. Moreover, the foamability of the hair bleach/hair dye remover is improved, and the durability of foam obtained by foaming is also enhanced.

When the cationic surfactant contains an ammonium cationic surfactant having an alkyl group with 16 or more and 22 or less carbon atoms and an ammonium cationic surfactant having an alkyl group with 10 or more and less than 16 carbon atoms, the easiness of mixing and foaming of the hair bleach/hair dye remover is further improved, and the retainability of the foamy hair bleach/hair dye remover on hair is also further improved. Moreover, the foam quality of the foamy hair bleach/hair dye remover is improved.

When the hair bleach/hair dye remover contains an anionic surfactant or an amphoteric surfactant, it becomes easy to enhance the foamability of the hair bleach/hair dye remover.

Also when the first agent in the hair bleach/hair dye remover contains a nonionic polymer, the easiness of mixing and foaming of the hair bleach/hair dye remover is improved, and the retainability of the foamy hair bleach/hair dye remover on hair is improved. Moreover, the foam quality of the foamy hair bleach/hair dye remover, for example, the homogeneity or elasticity of foam, is also improved.

Also when the first agent in the hair bleach/hair dye remover contains a thickener, the easiness of mixing and foaming of the hair bleach/hair dye remover is improved, and the retainability of the foamy hair bleach/hair dye remover on hair is improved. Moreover, the hair bleach/hair dye remover when applied to hair drips insubstantially from the hair by virtue of appropriate viscosity imparted by the thickener to the hair bleach/hair dye remover.

The hair bleach/hair dye remover may contain an anionic surfactant, a cationic surfactant, a thickener other than starch, and starch. The starch may be incorporated in the first agent having a powdery form, and the hair bleach/hair dye remover may be constituted such that the anionic surfactant and the cationic surfactant come into contact with each other in the presence of a solvent in use of the hair bleach/hair dye remover. In this case, the onset of a thickening effect can quickly take place during the mixing of the first and second agents.

When the starch is incorporated in the powdery first agent, the rate of onset of a thickening effect can be accelerated during the mixing of the first and second agents. In addition, the viscosity stability of the hair bleach/hair dye remover can be improved.

Also when the second agent in the hair bleach/hair dye remover contains a cationic polymer, the easiness of mixing and foaming of the hair bleach/hair dye remover is improved, and the retainability of the foamy hair bleach/hair dye remover on hair is improved. Moreover, hair texture after treatment with the hair bleach/hair dye remover can be improved. Particularly, when the cationic polymer is incorporated together with hydrogen peroxide in either of the first or second agent of the hair bleach/hair dye remover, the hair texture improving effect of the cationic polymer can be enhanced.

Also when the second agent in the hair bleach/hair dye remover contains an inorganic salt of alkali metal, the easiness of mixing and foaming of the hair bleach/hair dye remover is improved, and the retainability of the foamy hair bleach/hair dye remover on hair is improved. Moreover, when hydrogen peroxide is used as an oxidizing agent and an amphoteric surfactant is incorporated in the second agent, the inorganic salt of alkali metal can improve the stability of the hydrogen peroxide.

Also when the second agent in the hair bleach/hair dye remover contains phenoxyethanol and at least one selected from benzoic acid and benzoates, the easiness of mixing and foaming of the hair bleach hair dye remover is improved, and the retainability of the foamy hair bleach/hair dye remover on hair is improved. Moreover, when hydrogen peroxide is used as an oxidizing agent, phenoxyethanol and benzoic acid or benzoates can improve the stability of the hydrogen peroxide.

When hydrogen peroxide is used as an oxidizing agent, the combined use of the surfactant, phenoxyethanol, and at least one selected from benzoic acid and benzoates can further improve the stability of hydrogen peroxide.

It is preferred that the alkali agent should be a carbonate. Moreover, when the content of the chelating agent in the mixture of the first and second agents is 1 to 5% by mass, it is preferred that the mass ratio of the content of the carbonate in the mixture of the first and second agents to that of the chelating agent in the same mixture should be 0.02 to 6.5. In this case as well, the easiness of mixing and foaming of the hair bleach/hair dye remover is improved, and the retainability of the foamy hair bleach/hair dye remover on hair is improved. Moreover, reduction in hair texture after treatment with the hair bleach/hair dye remover that is caused by the use of the carbonate can be suppressed.

Second Embodiment

Hereinafter, a second embodiment of the present invention will be described. A hair cosmetic composition according to the second embodiment is a two-part hair dye. The hair dye of this embodiment comprises, for example, a powdery first agent and a liquid second agent containing at least an oxidizing agent. This hair dye is prepared in a foamy form by mixing the first and second agents and foaming the mixture by shaking and then applied to hair for dyeing hair.

In addition to an alkali agent as Component F, the first agent further contains, for example, an anionic surfactant as a component C, a nonionic polymer as a component D, a thickener as a component E, a chelating agent as a component L, and an oxidation dye.

The oxidation dye can develop color due to oxidative polymerization induced by the oxidizing agent contained in the second agent of the hair dye and comprises at least a dye intermediate. The oxidation dye may contain a coupler in addition to the dye intermediate.

Examples of the dye intermediate include p-phenylenediamine, toluene-2,5-diamine (p-toluoylenediamine), N-phenyl-p-phenylenediamine, 4,4'-diaminodiphenylamine, p-aminophenol, o-aminophenol, p-methylaminophenol, N,N-bis(2-hydroxyethyl)-p-phenylenediamine, 2-hydroxyethyl-p-phenylenediamine, o-chloro-p-phenylenediamine, 4-amino-m-cresol, 2-amino-4-hydroxyethylaminoanisole, 2,4-diaminophenol, and salts thereof. Only one kind of the dye intermediate may be used, or two or more kinds of the dye intermediates may be used in combination.

The coupler develops color through binding to the dye intermediate. Examples of the coupler include resorcin, 5-amino-o-cresol, m-aminophenol, α-naphthol, 5-(2-hydroxyethylamino)-2-methylphenol, m-phenylenediamine, 2,4-diaminophenoxyethanol, toluene-3,4-diamine, 2,6-diaminopyridine, diphenylamine, N,N-diethyl-m-aminophenol, phenyl methylpyrazolone, and salts thereof. Only one kind of the coupler may be used, or two or more kinds of the couplers may be used in combination. The oxidation dye containing both of the dye intermediate and the coupler is preferably used because it is easy to change the color tone of hair to a desired one.

The first agent in the hair dye may further contain, as appropriate, at least one selected from oxidation dyes and direct dyes listed in, for example, "Japanese Standards of Quasi-Drugs Ingredients" (issued in June 2006, Yakuji Nippo Ltd.).

The second agent in the hair dye has, for example, the same composition as that of the second agent in the hair bleach/hair dye remover according to the first embodiment.

The first agent in the hair dye has a powdery form. The second agent has a liquid form. The hair dye is prepared in a foamy form by mixing the first and second agents and foaming the mixture by shaking and then applied in a necessary amount to hair by hand using thin-gloves or with a comb or brush. The preparation of the hair dye having a foamy form may be performed using the container 20 shown in FIGS. 1(a) to 2, as in the hair bleach/hair dye remover according to the first embodiment.

The second embodiment has the following advantages in addition to those of the first, embodiment.

The hair dye of the second embodiment comprises a powdery first agent and a liquid second agent. A foamy hair dye obtained by mixing the first and second agents and foaming the mixture by shaking has small bubbles. Thus, the hair dye can be mixed and foamed easily, as in the hair bleach/hair dye remover of the first embodiment. Moreover, the foamy hair dye is favorably retained on hair.

The first and second embodiments may be modified as follows.

Although the hair cosmetic compositions of the first and second embodiments comprise a powdery first agent and a liquid second agent, the first and second agents may be in liquid and powdery forms, respectively. In this case as well, the easiness of mixing and foaming of the hair cosmetic composition and the retainability of the foamy hair cosmetic composition on hair can be improved. When the first agent has a liquid form, ammonia or alkanolamine that is in a liquid state at 25° C. may be used as an alkali agent.

The two-part hair dye of the second embodiment may be constituted by changing it to a three-part type comprising at least a powdery agent and a liquid agent or a multipart type comprising four or more agents.

In the first and second embodiments, the foaming procedures performed for obtaining a foamy hair cosmetic composition may be changed as follows: the hair cosmetic composition may be made foamy by mixing air by application of vibration into the hair cosmetic composition before foaming. Alternatively, the hair cosmetic composition may be made foamy by mixing air by application of rotation into the hair cosmetic composition before foaming. Specifically, the foaming of the hair cosmetic composition by shaking means that the hair cosmetic composition is made foamy by shaking up the hair cosmetic composition with air, by applying vibration to the hair cosmetic composition, or by applying rotation to the hair cosmetic composition.

According to such types of the foaming procedures, the foaming tool used for foaming the hair cosmetic composition can be changed. For example, when the hair cosmetic composition is foamed mainly by application of vibration, vibrator and a hand-operated whisk are preferable as the foaming tool. When the hair cosmetic composition is foamed mainly by application of rotation, a stirring rod, a stirring bar, and an electric whisk are preferable as the foaming tool. The foaming of the hair cosmetic composition using such a foaming tool is performed within, for example, a container having an opening at the upper end, after addition of the hair cosmetic composition to the container. In any of these cases, the hair cosmetic composition can be foamed easily and favorably.

The shape of the main body 21 of the container 20 shown in FIGS. 1(a) to 2 is not limited to a bottomed cylindrical shape and may be, for example, a bottomed rectangular tubular form. Moreover, the shape of the lid 22 may be changed appropriately according to, for example, the shape of the main body 21.

The storage state of the individually packaged first and second agents before use is not limited to the state in which they are contained in the container 20 as shown in FIG. 1(a). Specifically, at least one of the first and second agents may be stored outside the container 20.

For foaming the hair cosmetic composition by shaking up it with air, the container 20 may be shaken, for example, by turning the wrist of hand grasping the container 20, instead of shaking the container 20 up and down as shown in FIG. 1(c).

EXAMPLES

Next, the present invention will be described more specifically with reference to Examples and Comparative Examples.

Test 1

Hair bleaches of Examples 1-1 to 1-12 and Comparative Examples 1-1 to 1-8 were prepared. The hair bleaches of Examples 1-1 to 1-12 were a two-part type comprising a powdery first agent and an emulsion second agent. The first and second agents in the hair bleaches of these Examples had the compositions shown in Table 1. The hair bleaches of Comparative Examples 1-1 to 1-8 were a two-part type comprising liquid first and second agents. The first and second agents in the hair bleaches of these Comparative Examples had the compositions shown in Table 2. In Tables 1 and 2, units for the numeric values representing the content of each component in the hair bleaches are % by mass. The first and second agents of the hair bleaches of Examples were mixed at a mass ratio of 1:5. The first and second agents of the hair bleaches of Comparative Examples were mixed at a mass ratio of 1:1.5.

In Examples 1-1 to 1-11 and Comparative Examples 1-3 and 1-7, the mixing of the first and second agents was performed using a shaker comprising the same container as the container 20 shown in FIGS. 1(a) to 2. More specifically, after addition of the first and second agents to the container, the container was shaken twenty times to obtain a foamy hair bleach. In Example 1-12, a foamy hair bleach was obtained using a whisk (muddler for hair coloring agents). In Comparative Examples 1-1 and 1-5, the first and second agents were mixed without foaming in a squeeze foamer container 1 (container included in PRETTIA (manufactured by Kao Corp.)) and then discharged from the container to obtain a foamy hair bleach. In Comparative Examples 1-2 and 1-6, the first and second agents were mixed without foaming in a pump discharging container (F5L-type foamer container; manufactured by Daiwa Can Company) and then discharged from the container to obtain a foamy hair bleach. In Comparative Examples 1-4 and 1-8, the first and second agents were mixed by shaking using a squeeze foamer container 2 (container included in PRETTIA (manufactured by Kao Corp.) except that a dip tube for suction was omitted) and then discharged from the container to obtain a foamy hair bleach. The hair bleach of each of Examples and Comparative Examples was evaluated for the easiness of mixing and foaming and retainability on hair. The results are shown in Tables 1 and 2.

The "Mass ratio of carbonate (f-1)/L" column of Table 1 represents the mass ratio of the content of the carbonate in the hair bleach in use to that of the chelating agent in the same hair bleach.

<Easiness of Mixing and Foaming>

Whether or not the mixing and foaming of the first and second agents in the hair bleach of each of Examples and Comparative Examples was easy was evaluated on a 1-to-5 scale as follows.

5: Exceedingly easy.

4: Considerably easy.

3: Slightly easy.

2: Less easy.

1: Not easy.

<Retainability on Hair>

A hair bundle of 30 cm in length was dangled, and the foamy hair bleach of each of Examples and Comparative Examples was attached to the upper portion of the hair bundle. Then, the movement of the attached foam was observed after being left for 30 minutes, and evaluated on a 1-to-5 scale as follows.

5: The foam does not move.

4: The foam moves insubstantially.

3: The foam does not show mach movement.

2: The foam moves considerably.

1: The foam moves very much.

TABLE 1

|     |                                              | Example 1-1 | Example 1-2 | Example 1-3 | Example 1-4 | Example 1-5 | Example 1-6 |
|-----|----------------------------------------------|-------------|-------------|-------------|-------------|-------------|-------------|
|     | First agent (powdery)                        |             |             |             |             |             |             |
| (F) | Ammonium sulfate                             | 15          | 15          | 15          | 15          | 15          | 15          |
|     | Magnesium stearate                           | 1           | 1           | 1           | 1           | 1           | 1           |
| (L) | Trisodium ethylenediaminehydroxyethyltriacetate | 4        | 4           | 4           | 4           | 4           | 4           |
| (D) | Cyclodextrin                                 | 5           | 5           | 5           | 5           | 5           |             |
| (D) | Potato starch                                | 10          | 10          | 10          | 10          | 10          |             |
| (C) | Disodium lauryl sulfosuccinate               | 5           | 17          | 5           |             | 5           | 5           |
| (L) | Tetrasodium edetate                          | 5           | 5           | 5           | 5           | 5           | 5           |
| (E) | Carboxymethylcellulose                       | 2           | 2           | 2           | 2           | 2           | 2           |
| (f-1) | Sodium carbonate                           | 25          | 25          | 25          | 25          | 25          | 25          |
| (E) | Hydroxyethylcellulose                        | 15          | 15          | 15          | 15          | 15          | 30          |
|     | Ascorbic acid                                | 0.1         | 0.1         | 0.1         | 0.1         | 0.1         | 0.1         |
|     | Sodium sulfate                               | 12.9        | 0.9         | 12.9        | 17.9        | 12.9        | 12.9        |
|     | Total amount of first agent                  | 100         | 100         | 100         | 100         | 100         | 100         |
|     | Second agent (liquid)                        |             |             |             |             |             |             |
| (G) | 35 w/v % hydrogen peroxide                   | 12          | 12          | 12          | 12          | 12          | 12          |
| (A) | Coconut oil fatty acid amidopropyl betaine   | 2.4         |             | 3.78        | 2.4         | 2.4         | 2.4         |
| (b-2) | Laury trimethyl ammonium chloride          | 1           | 1           |             | 1           |             | 1           |
| (b-1) | Cetyl trimethyl ammonium chloride          | 0.38        | 0.38        |             | 0.38        | 1.38        | 0.38        |
| (C) | Disodium lauryl sulfosuccinate               |             |             |             | 1           |             |             |
| (H) | Dimethyl diallyl ammonium chloride-acrylamide copolymer | 0.02 | 0.02 | 0.02 | 0.02 | 0.02 | 0.02 |
| (H) | Polydimethylmethylenepiperidinium chloride   | 0.5         | 0.5         | 0.5         | 0.5         | 0.5         | 0.5         |
|     | Hydroxyethanediphosphonic acid               | 0.2         | 0.2         | 0.2         | 0.2         | 0.2         | 0.2         |
| (J) | Phenoxyethanol                               | 0.2         | 0.2         | 0.2         | 0.2         | 0.2         | 0.2         |
|     | Dipropylene glycol                           | 0.15        | 0.15        | 0.15        | 0.15        | 0.15        | 0.15        |
| (K) | Sodium benzoate                              | 0.2         | 0.2         | 0.2         | 0.2         | 0.2         | 0.2         |
| (I) | Sodium chloride                              | 0.4         | 0.4         | 0.4         | 0.4         | 0.4         | 0.4         |
|     | Purified water                               | Remainder   | Remainder   | Remainder   | Remainder   | Remainder   | Remainder   |
|     | Total amount of second agent                 | 100         | 100         | 100         | 100         | 100         | 100         |
|     | Mixing ratio (mass ratio) between first and second agents | 1:5 | 1:5 | 1:5 | 1:5 | 1:5 | 1:5 |
|     | Mass ratio of carbonate (f-1)/L              | 2.78        | 2.78        | 2.78        | 2.78        | 2.78        | 2.78        |
|     | Foam preparation container                   | Shaker      | Shaker      | Shaker      | Shaker      | Shaker      | Shaker      |
|     | Evaluation                                   |             |             |             |             |             |             |
|     | Easiness of mixing and foaming               | 5           | 5           | 5           | 3           | 5           | 4           |
|     | Retainability on hair                        | 5           | 4           | 3           | 3           | 4           | 4           |

|     |                                              | Example 1-7 | Example 1-8 | Example 1-9 | Example 1-10 | Example 1-11 | Example 1-12 |
|-----|----------------------------------------------|-------------|-------------|-------------|--------------|--------------|--------------|
|     | First agent (powdery)                        |             |             |             |              |              |              |
| (F) | Ammonium sulfate                             | 15          | 15          | 15          | 15           | 15           | 15           |
|     | Magnesium stearate                           | 1           | 1           | 1           | 1            | 1            | 1            |
| (L) | Trisodium ethylenediaminehydroxyethyltriacetate | 4        | 4           | 4           | 4            |              | 4            |
| (D) | Cyclodextrin                                 | 5           | 5           | 5           | 5            | 5            | 5            |
| (D) | Potato starch                                | 10          | 10          | 10          | 10           | 10           | 10           |
| (C) | Disodium lauryl sulfosuccinate               | 5           | 5           | 5           | 5            | 5            |              |
| (L) | Tetrasodium edetate                          | 5           | 5           | 5           | 5            |              | 5            |
| (E) | Carboxymethylcellulose                       |             | 2           | 2           | 2            | 2            | 2            |
| (f-1) | Sodium carbonate                           | 25          | 25          | 25          | 25           | 25           | 25           |
| (E) | Hydroxyethylcellulose                        | 17          | 15          | 15          | 15           | 15           | 15           |
|     | Ascorbic acid                                | 0.1         | 0.1         | 0.1         | 0.1          | 0.1          | 0.1          |
|     | Sodium sulfate                               | 12.9        | 12.9        | 12.9        | 12.9         | 21.9         | 12.9         |
|     | Total amount of first agent                  | 100         | 100         | 100         | 100          | 100          | 100          |
|     | Second agent (liquid)                        |             |             |             |              |              |              |
| (G) | 35 w/v % hydrogen peroxide                   | 12          | 12          | 12          | 12           | 12           | 12           |
| (A) | Coconut oil fatty acid amidopropyl betaine   | 2.4         | 2.4         | 2.4         | 2.4          | 2.4          | 2.4          |
| (b-2) | Laury trimethyl ammonium chloride          | 1           | 1           | 1           | 1            | 1            | 1            |
| (b-1) | Cetyl trimethyl ammonium chloride          | 0.38        | 0.38        | 0.38        | 0.38         | 0.38         | 0.38         |
| (C) | Disodium lauryl sulfosuccinate               |             |             |             |              |              |              |
| (H) | Dimethyl diallyl ammonium chloride-acrylamide copolymer | 0.02 |          | 0.02        | 0.02         | 0.02         | 0.02         |

TABLE 1-continued

|   | | | | | | | |
|---|---|---|---|---|---|---|---|
| (H) | Polydimethylmethylenepiperidinium chloride | 0.5 | | 0.5 | 0.5 | 0.5 | 0.5 |
|  | Hydroxyethanediphosphonic acid | 0.2 | 0.2 | 0.2 | 0.2 | | 0.2 |
| (J) | Phenoxyethanol | 0.2 | 0.2 | 0.2 | | 0.2 | 0.2 |
|  | Dipropylene glycol | 0.15 | 0.15 | 0.15 | 0.15 | 0.15 | 0.15 |
| (K) | Sodium benzoate | 0.2 | 0.2 | 0.2 | | 0.2 | 0.2 |
| (I) | Sodium chloride | 0.4 | 0.4 | | 0.4 | 0.4 | 0.4 |
|  | Purified water | Remainder | Remainder | Remainder | Remainder | Remainder | Remainder |
|  | Total amount of second agent | 100 | 100 | 100 | 100 | 100 | 100 |
|  | Mixing ratio (mass ratio) between first and second agents | 1:5 | 1:5 | 1:5 | 1:5 | 1:5 | 1:5 |
|  | Mass ratio of carbonate (f-1)/L | 2.78 | 2.78 | 2.78 | 2.78 | — | 2.78 |
|  | Foam preparation container | Shaker | Shaker | Shaker | Shaker | Shaker | Whisk |
|  | Evaluation | | | | | | |
|  | Easiness of mixing and foaming | 5 | 5 | 5 | 5 | 4 | 4 |
|  | Retainability on hair | 4 | 5 | 5 | 5 | 5 | 4 |

TABLE 2

|   | | Comparative Example 1-1 | Comparative Example 1-2 | Comparative Example 1-3 | Comparative Example 1-4 | Comparative Example 1-5 | Comparative Example 1-6 | Comparative Example 1-7 | Comparative Example 1-8 |
|---|---|---|---|---|---|---|---|---|---|
|  | First agent (liquid) | | | | | | | | |
|  | 28% ammonia | 8.5 | 8.5 | 8.5 | 8.5 | 6 | 6 | 6 | 6 |
| (f-1) | Ammonium bicarbonate | 8 | 8 | 8 | 8 | 10 | 10 | 10 | 10 |
|  | Decyl poly(1.4)glucoside | 3.2 | 3.2 | 3.2 | 3.2 | 6 | 6 | 6 | 6 |
|  | POE(23) lauryl ether | 2 | 2 | 2 | 2 | 2 | 2 | 2 | 2 |
|  | Propylene glycol | 4 | 4 | 4 | 4 | 4 | 4 | 4 | 4 |
|  | Ethanol | | | | | 7 | 7 | 7 | 7 |
| (H) | Dimethyl diallyl ammonium chloride-acrylamide copolymer | 0.5 | 0.5 | 0.5 | 0.5 | 0.5 | 0.5 | 0.5 | 0.5 |
| (L) | Tetrasodium edetate | 0.1 | 0.1 | 0.1 | 0.1 | 0.1 | 0.1 | 0.1 | 0.1 |
|  | Ascorbic acid | 0.4 | 0.4 | 0.4 | 0.4 | 0.3 | 0.3 | 0.3 | 0.3 |
|  | Anhydrous sodium sulfite | 0.5 | 0.5 | 0.5 | 0.5 | 0.4 | 0.4 | 0.4 | 0.4 |
|  | Purified water | Remainder | Remainder | Remainder | Remainder | Remainder | Remainder | Remainder | Remainder |
|  | Total amount of first agent | 100 | 100 | 100 | 100 | 100 | 100 | 100 | 100 |
|  | Second agent (liquid) | | | | | | | | |
| (G) | 35 w/v % hydrogen peroxide | 16.3 | 16.3 | 16.3 | 16.3 | 16.3 | 16.3 | 16.3 | 16.3 |
| (C) | Sodium POE(2.5) lauryl ether sulfate | 1.9 | 1.9 | 1.9 | 1.9 | 0.5 | 0.5 | 0.5 | 0.5 |
|  | Glycerin mono-2-ethylhexyl ether | | | | | 0.1 | 0.1 | 0.1 | 0.1 |
| (A) | Amidopropyl betaine laurate | | | | | 0.1 | 0.1 | 0.1 | 0.1 |
|  | Lauric acid | 0.04 | 0.04 | 0.04 | 0.04 | 0.01 | 0.01 | 0.01 | 0.01 |
|  | Cetyl alcohol | 0.6 | 0.6 | 0.6 | 0.6 | 0.58 | 0.58 | 0.58 | 0.58 |
|  | Stearyl alcohol | | | | | 0.15 | 0.15 | 0.15 | 0.15 |
|  | Hydroxyethanediphosphonic acid | 0.08 | 0.08 | 0.08 | 0.08 | 0.08 | 0.08 | 0.08 | 0.08 |
|  | Sodium hydroxide | Appropriate amount | Appropriate amount | Appropriate amount | Appropriate amount | Appropriate amount | Appropriate amount | Appropriate amount | Appropriate amount |
|  | Purified water | Remainder | Remainder | Remainder | Remainder | Remainder | Remainder | Remainder | Remainder |
|  | Total amount of second agent | 100 | 100 | 100 | 100 | 100 | 100 | 100 | 100 |
|  | Mixing ratio (mass ratio) between first and second agents | 1:1.5 | 1:1.5 | 1:1.5 | 1:1.5 | 1:1.5 | 1:1.5 | 1:1.5 | 1:1.5 |
|  | Foam preparation container | Squeeze foamer container 1 | Pump discharging container | Shaker | Squeeze foamer container 2 | Squeeze foamer container 1 | Pump discharging container | Shaker | Squeeze foamer container 2 |
|  | Evaluation | | | | | | | | |
|  | Easiness of mixing and foaming | 1 | 1 | 5 | 4 | 1 | 1 | 5 | 4 |
|  | Retainability on hair | 1 | 1 | 1 | 1 | 1 | 1 | 1 | 1 |

As shown in Table 1, the foamy hair bleaches of Examples that were prepared by using the powdery first agent and the liquid second agent and shaking the mixture using a shaker produced favorable results in both the evaluations for the easiness of mixing and foaming and retainability on hair.

As shown in Table 2, the foamy hair bleaches of Comparative Examples 1-1 and 1-5 that were prepared by using the squeeze foamer container 1 and mixing the first and second agents without foaming, followed by discharge from the container produced results inferior to those of Examples in both the evaluations for the easiness of mixing and foaming and retainability on hair.

The foamy hair bleaches of Comparative Examples 1-2 and 1-6 that were prepared by using the pump discharging container and mixing the first and second agents without foaming, followed by discharge from the container produced results inferior to those of Examples in both the evaluations for the easiness of mixing and foaming and retainability on hair.

The foamy hair bleaches of Comparative Examples 1-3 and 1-7 that were prepared by using the first and second agents both in a liquid form and shaking the mixture using a shaker produced results inferior to those of Examples in the evaluation for retainability on hair.

The foamy hair bleaches of Comparative Examples 1-4 and 1-8 that were prepared by using the squeeze foamer container 2 and mixing the first and second agents by shaking, followed by discharge from the container produced result inferior to those of Examples in the evaluation for retainability on hair.

Test 2

Examples 2-1 to 2-9

Oxidation hair dyes of Examples 2-1 to 2-9 were prepared. These oxidation hair dyes were a two-part type comprising powdery first agent and a liquid second agent. The first and second agents had the composition shown in Table 3. In Table 3, units for the numeric values representing the content of each component in the oxidation, hair dyes are % by mass. The first agent is not necessarily required to have a powdery form, and the second agent is not necessarily required to have a liquid form.

Next, the oxidation hair dye of each of Examples was foamed using the same sealable container (A1) as the container 20 shown in FIGS. 1(a) to 2 or a whisk (B) for oxidation hair dye preparation. The sealable container used had a capacity of 770 mL, a height of 17 cm, and an inside diameter of 7 to 8 cm. To this container, 150 g of the mixture of the first and second agents was added, and the container was shaken up and down 20 times. The mixture of the first and second agents was thus shaken up with air to obtain an oxidation hair dye in a foamy form. Alternatively, to a 600 mL cup, 150 g of the mixture of the first and second agents was added and then stirred by the predetermined number of rotations of the whisk to obtain an oxidation hair dye in a foamy form.

Reference Example 2-1

A two-part oxidation hair dye having the same composition as that of the oxidation hair dye of Example 2-1 was foamed according to a routine method, using a squeeze-type foamer container (C).

Reference Example 2-2

A two-part oxidation hair dye having the same composition as that of the oxidation hair dye of Example 2-1 was foamed according to a routine method using a pump-type foamer container (D).

Reference Examples 2-3 and 2-4

A two-part oxidation hair dye having the same composition as that of the oxidation hair dye of Example 2-1 except that the amphoteric surfactant was omitted was foamed in the same way as in Example 2-1.

<Foam Volume>

The state after foaming was visually observed by expert panelists for the oxidation hair dyes of Examples and Reference Examples. As a result, each oxidation hair dye was evaluated according to the evaluation criteria: those excellent in foam volume were given a score 5; those good in foam volume were given a score 4; those having favorable foaming were given a score 3; those having a slightly poor foam volume were given a score 2; and those having a poor foam volume were given a score 1. Numeric values of the evaluation results are shown in the "Evaluation for foam volume" column of Table 3.

<Fineness of Foam>

The state after foaming was visually observed by expert panelists for the oxidation hair dyes of Examples and Reference Examples. As a result, each oxidation hair dye was evaluated according to the evaluation criteria: those excellent for fineness of foam were given a score 5; those good for fineness of foam were given a score 4; those having favorable fineness of foam were given a score 3; those having slightly coarse foam were given a score 2; and those having very coarse foam were given a score 1. Numeric values of the evaluation results are shown in the "Evaluation for fineness of foam" column of Table 3.

<Handleability after Foaming>

Expert panelists took in hand with gloves (made of polyethylene) the oxidation hair dye of each of Examples and Reference Examples after foaming and transferred it to hair. At this time, the state in which each oxidation hair dye was retained on hand was observed by the expert panelists. As a result, each oxidation hair dye was evaluated according to the evaluation criteria: those excellent in retainability on hand were given a score 5; those good in retainability were given a score 4; those having favorable retainability were given a score 3; those having slightly poor retainability were given a score 2; and those having poor retainability were given a score 1. Numeric values of the evaluation results are shown in the "Evaluation for handleability after foaming" column of Table 3.

TABLE 3

|  | Example 2-1 | Example 2-2 | Example 2-3 | Example 2-4 | Example 2-5 | Example 2-6 | Example 2-7 |
|---|---|---|---|---|---|---|---|
| First agent | | | | | | | |
| Ammonium sulfate | 15 | 15 | 15 | 15 | 15 | 15 | 15 |
| Sodium carbonate | 30 | 30 | 30 | 30 | 30 | 30 | 30 |
| Disodium adetate | 3 | 3 | 3 | 3 | 3 | 3 | 3 |

TABLE 3-continued

| | | | | | | | |
|---|---|---|---|---|---|---|---|
| Magnesium stearate | 1 | 1 | 1 | 1 | 1 | 1 | 1 |
| Toluene-2,5-diamine sulfate | 3 | 3 | 3 | 3 | 3 | 3 | 3 |
| Sodium lauryl sulfate | 5 | 5 | 5 | 5 | 5 | 5 | 5 |
| Carboxymethylcellulose | 15 | 15 | 15 | 15 | 15 | 15 | 15 |
| Sodium sulfate | Remainder | Remainder | Remainder | Remainder | Remainder | Remainder | Remainder |
| Total | 100 | 100 | 100 | 100 | 100 | 100 | 100 |
| Second agent | | | | | | | |
| 35% hydrogen peroxide | 15 | 15 | 15 | 15 | 15 | 15 | 15 |
| Coconut oil fatty acid amidopropyl betaine | 2.4 | — | — | 0.6 | 1.8 | 3 | 4 |
| Lauryldimethylaminoacetic acid betaine | — | 2.4 | — | — | — | — | — |
| Amidopropyl betaine laurate | — | — | 2.4 | — | — | — | — |
| POE(5) lauryl ether | 0.5 | 0.5 | 0.5 | 0.5 | 0.5 | 0.5 | 0.5 |
| Stearyl trimethyl ammonium chloride | 1 | 1 | 1 | 1 | 1 | 1 | 1 |
| Sodium lauryl sulfate | — | — | — | — | — | — | — |
| Purified water | Remainder | Remainder | Remainder | Remainder | Remainder | Remainder | Remainder |
| Total | 100 | 100 | 100 | 100 | 100 | 100 | 100 |
| Mixing ratio (first agent:second agent) | 1:5 | 1:5 | 1:5 | 1:5 | 1:5 | 1:5 | 1:5 |
| Content of amphoteric surfactant in mixture | 2.0 | 2.0 | 2.0 | 0.5 | 1.5 | 2.5 | 3.3 |
| Foaming tool | A1 | A1 | A1 | A1 | A1 | A1 | A1 |
| Evaluation for foam volume | 5 | 5 | 5 | 3 | 4 | 5 | 5 |
| Evaluation for fineness of foam | 5 | 5 | 5 | 3 | 4 | 5 | 4 |
| Evaluation for handleability after foaming | 5 | 5 | 5 | 5 | 5 | 5 | 5 |

| | Example 2-8 | Example 2-9 | Reference Example 2-1 | Reference Example 2-2 | Reference Example 2-3 | Reference Example 2-4 |
|---|---|---|---|---|---|---|
| First agent | | | | | | |
| Ammonium sulfate | 15 | 15 | 15 | 15 | 15 | 15 |
| Sodium carbonate | 30 | 30 | 30 | 30 | 30 | 30 |
| Disodium adetate | 3 | 3 | 3 | 3 | 3 | 3 |
| Magnesium stearate | 1 | 1 | 1 | 1 | 1 | 1 |
| Toluene-2,5-diamine sulfate | 3 | 3 | 3 | 3 | 3 | 3 |
| Sodium lauryl sulfate | 5 | 5 | 5 | 5 | 5 | 5 |
| Carboxymethylcellulose | 15 | 15 | 15 | 15 | 15 | 15 |
| Sodium sulfate | Remainder | Remainder | Remainder | Remainder | Remainder | Remainder |
| Total | 100 | 100 | 100 | 100 | 100 | 100 |
| Second agent | | | | | | |
| 35% hydrogen peroxide | 15 | 15 | 15 | 15 | 15 | 15 |
| Coconut oil fatty acid amidopropyl betaine | 6 | 2.4 | 2.4 | 2.4 | — | — |
| Lauryldimethylaminoacetic acid betaine | — | — | — | — | — | — |
| Amidopropyl betaine laurate | — | — | — | — | — | — |
| POE(5) lauryl ether | 0.5 | 0.5 | 0.5 | 0.5 | 0.5 | 0.5 |
| Stearyl trimethyl ammonium chloride | 1 | 1 | 1 | 1 | 3.4 | — |
| Sodium lauryl sulfate | — | — | — | — | — | 3.4 |
| Purified water | Remainder | Remainder | Remainder | Remainder | Remainder | Remainder |
| Total | 100 | 100 | 100 | 100 | 100 | 100 |
| Mixing ratio (first agent:second agent) | 1:5 | 1:5 | 1:5 | 1:5 | 1:5 | 1:5 |
| Content of amphoteric surfactant in mixture | 5.0 | 2.0 | 2.0 | 2.0 | 0.0 | 0.0 |
| Foaming tool | A1 | B | C | D | A1 | A1 |
| Evaluation for foam volume | 5 | 4 | 1 | 1 | 1 | 5 |
| Evaluation for fineness of foam | 3 | 4 | 1 | 1 | 1 | 1 |
| Evaluation for handleability after foaming | 4 | 4 | x | x | x | 1 |

As shown in Table 3, Examples 2-1 to 2-9 were given a score 3 or higher in all the results for foam volume, the fineness of foam, and handleability after foaming. Particularly, Examples 2-1 to 2-3, 2-5 to 2-7, and 2-9 were given a score 4 or higher in all the results for foam volume, the fineness of foam, and handleability after foaming. These results demonstrated that it is preferred that the content of the amphoteric surfactant in the oxidation hair dye (in the mixture) should be in the range of 1.5 to 4.0% by mass.

By contrast, Reference Examples 2-1 and 2-2 were given a score 1 in the result for foam volume, because squeeze-type and pump-type foamer containers, respectively, were used as foaming tools. Reference Example 2-3 used the same sealable container as that of Example 2-1 and however, was given a score 1 in the result for foam volume, because the oxidation hair dye contained a cationic surfactant instead of an amphoteric surfactant. Reference Example 2-4 was given a score 1 in the result for the fineness of foam, because the oxidation hair dye contained an anionic surfactant instead of an amphoteric surfactant in Reference Examples 2-1 to 2-3, the mark "x" shown in the "Evaluation for handleability after foaming" column of Table 3 represents the incapability of evaluation due to a lack of foaming.

Example 2-1a

An oxidation hair dye in a foamy form was obtained in the same way as in Example 2-1 except that the number of up and down shakes was changed to 10.

Examples 2-1b and 2-1c

An oxidation hair dye in a foamy form was obtained in the same way as in Example 2-1 except that sealable containers (A2 and A3) differing in capacity were used and the number of up and down shakes was changed to 10.

Examples 2-1d to 2-1f

An oxidation hair dye in a foamy form was obtained in the same way as in Example 2-1 except that the amount of the oxidation hair dye added to the sealable container (A1) was changed and the number of up and down shakes of the sealable container (A1) was changed to 10.
(Evaluation)
Examples 2-1a to 2-1f were evaluated for the <foam volume> and the <fineness of foam>. Numeric values of the evaluation results are shown in the "Evaluation for foam volume" and "Evaluation for fineness of foam" columns of Table 4.

As shown in Table 4, Examples 2-1a, 2-1c, and 2-1e were given a score 4 or 5 in the evaluation results for foam volume and the fineness of foam and were better than Examples 2-1b and 2-1d. These results demonstrated that it is preferred that the ratio (mL/g) of the interior volume (unit: mL) of the sealable container to the mass (unit: g) of the oxidation hair dye (mixture) should be in the range of 2 to 15.

Test 3

Examples 3-1 to 3-8 and Reference Examples 3-1 to 3-4

Oxidation hair dyes of Examples 3-1 to 3-8 and Reference Examples 3-1 to 3-4 were prepared. These oxidation hair dyes were a two-part type comprising a powdery first agent and a liquid second agent. The first and second agents had the composition shown in Tables 5 and 6. In Tables 5 and 6 and subsequent Tables 7 and 8, units for the numeric values representing the content of each component in the oxidation hair dyes are % by mass. The first agent is not necessarily required to have a powdery form, and the second agent is not necessarily required to have a liquid form. In Tables 5 to 8, the mixing ratio represents a mass ratio.

Next, the oxidation hair dye of each of Examples and Reference Examples was foamed using the same sealable container as the container 20 shown in FIGS. 1(a) to 2. The sealable container used had a capacity of 770 mL, a height of 17 cm, and an inside diameter of 7 to 8 cm. To this container, 150 g of the mixture of the first and second agents was added, and the container was shaken up and down 20 times. The mixture of the first and second agents was thus shaken up with air to obtain an oxidation hair dye in a foamy form.

Examples 3-9 to 3-24

An oxidation hair dye in a foamy form was obtained in the same way as in Example 3-1 from a two-part oxidation hair dye differing in the content of at least one of the anionic and cationic surfactants from the composition of the oxidation hair dye of Example 3-1.
<Foamability>
The state after foaming was visually observed by expert panelists for the oxidation hair dyes of Examples and Reference Examples. The results were evaluated according to the following evaluation criteria.
5: The amount of foaming is excellent.
4: The amount of foaming is good.
3: The amount of foaming is favorable.
2: The amount of foaming is slightly poor.
1: The amount of foaming is poor.
Numeric values of the evaluation results are shown in the "Evaluation for foamability" column of Tables 5 to 8.

TABLE 4

| | | Example 2-1a | Example 2-1b | Example 2-1c | Example 2-1d | Example 2-1e | Example 2-1f |
|---|---|---|---|---|---|---|---|
| Sealable container | Type | A1 | A2 | A3 | A1 | A1 | A1 |
| | Interior volume (mL) | 770 | 230 | 2000 | 770 | 770 | 770 |
| | Height (cm) of accommodating portion | 17 | 7 | 30 | 17 | 17 | 17 |
| Mixture of first and second agents | Mass (g) | 150 | 150 | 150 | 30 | 72 | 450 |
| | Height (cm) before foaming | 4 | 4 | 2.5 | 1 | 2 | 10 |
| Interior volume (mL)/mass (g) of mixture | | 5.1 | 1.5 | 13.3 | 25.7 | 10.7 | 1.7 |
| Height (cm) of accommodating portion/height (cm) of mixture before foaming | | 4.1 | 1.8 | 12.0 | 17.0 | 8.5 | 1.7 |
| Evaluation for foam volume | | 5 | 3 | 5 | 3 | 4 | 3 |
| Evaluation for fineness of foam | | 5 | 3 | 4 | 3 | 4 | 3 |

‹Evaluation for Durability of Foam›

Time-dependent change in the state after foaming was visually observed by expert panelists for the oxidation hair dyes of Examples and Reference Examples. As a result, those in which little disappearance (break) of foam (defoaming) was observed after a lapse of 10 minutes immediately after foaming were given a score 5; those in which the disappearance (break) of approximately 10% foam was observed after this lapse of 10 minutes were given a score 4; those in which the disappearance (break) of approximately 20% foam was observed after this lapse of 10 minutes were given a score 3; those in which the disappearance (break) of approximately 30% foam was observed after this lapse of 10 minutes were given a score 2; and those in which the disappearance (break) of approximately 40% foam was observed after this lapse of 10 minutes were given a score 1. Numeric values of the evaluation results are shown in the "Evaluation for durability of foam" column of Tables 5 to 8.

TABLE 5

|  |  | Example 3-1 | Example 3-2 | Example 3-3 | Example 3-4 | Example 3-5 | Example 3-6 | Example 3-7 | Example 3-8 |
|---|---|---|---|---|---|---|---|---|---|
|  | First agent |  |  |  |  |  |  |  |  |
|  | Ammonium sulfate | 15 | 15 | 15 | 15 | 15 | 15 | 15 | 15 |
|  | Sodium carbonate | 30 | 30 | 30 | 30 | 30 | 30 | 30 | 30 |
|  | Disodium edetate | 3 | 3 | 3 | 3 | 3 | 3 | 3 | 3 |
|  | Magnesium stearate | 1 | 1 | 1 | 1 | 1 | 1 | 1 | 1 |
|  | Toluene-2,5-diamine sulfate | 3 | 3 | 3 | 3 | 3 | 3 | 3 | 3 |
| (C) | Sodium lauryl sulfate | 5 | — | — | 5 | 5 | — | 5 | 5 |
| (C) | Sodium cetyl sulfate | — | 5 | — | — | — | — | — | — |
| (C) | Disodium lauryl sulfosuccinate | — | — | 5 | — | — | — | — | — |
| (B) | Stearyl trimethyl ammonium chloride | — | — | — | — | — | 5 | — | — |
|  | Carboxymethylcellulose | 15 | 15 | 15 | 15 | 15 | 15 | 15 | 15 |
|  | Sodium sulfate | Remainder | Remainder | Remainder | Remainder | Remainder | Remainder | Remainder | Remainder |
|  | Total | 100 | 100 | 100 | 100 | 100 | 100 | 100 | 100 |
|  | Second agent |  |  |  |  |  |  |  |  |
|  | 35% hydrogen peroxide | 15 | 15 | 15 | 15 | 15 | 15 | 15 | 15 |
| (A) | Coconut oil fatty acid amidopropyl betaine | 2.4 | 2.4 | 2.4 | 2.4 | 2.4 | 2.4 | — | — |
| (A) | Lauryldimethylaminoacetic acid betaine | — | — | — | — | — | — | 2.4 | — |
| (A) | Amidopropyl betaine laurate | — | — | — | — | — | — | — | 2.4 |
|  | POE(5) lauryl ether | 0.5 | 0.5 | 0.5 | 0.5 | 0.5 | 0.5 | 0.5 | 0.5 |
| (B) | Stearyl trimethyl ammonium chloride | 1 | 1 | 1 | — | — | — | 1 | 1 |
| (B) | Distearyl dimethyl ammonium chloride | — | — | — | 1 | — | — | — | — |
| (B) | Lauryl trimethyl ammonium chloride | — | — | — | — | 1 | — | — | — |
| (C) | Sodium lauryl sulfate | — | — | — | — | — | 1 | — | — |
|  | Purified water | Remainder | Remainder | Remainder | Remainder | Remainder | Remainder | Remainder | Remainder |
|  | Total | 100 | 100 | 100 | 100 | 100 | 100 | 100 | 100 |
|  | Mixing ratio (first agent:second agent) | 1:5 | 1:5 | 1:5 | 1:5 | 1:5 | 1:5 | 1:5 | 1:5 |
|  | Content of (C) in use | 0.8 | 0.8 | 0.8 | 0.8 | 0.8 | 0.8 | 0.8 | 0.8 |
|  | Content of (B) in use | 0.8 | 0.8 | 0.8 | 0.8 | 0.8 | 0.8 | 0.8 | 0.8 |
|  | Mass ratio (C)/(B) | 1 | 1 | 1 | 1 | 1 | 1 | 1 | 1 |
|  | Evaluation for foamability | 5 | 5 | 5 | 5 | 5 | 5 | 5 | 5 |
|  | Evaluation for durability of foam | 5 | 5 | 5 | 5 | 5 | 5 | 5 | 5 |

TABLE 6

|  |  | Reference Example 3-1 | Reference Example 3-2 | Reference Example 3-3 | Reference Example 3-4 |
|---|---|---|---|---|---|
|  | First agent |  |  |  |  |
|  | Ammonium sulfate | 15 | 15 | 15 | 15 |
|  | Sodium carbonate | 30 | 30 | 30 | 30 |
|  | Disodium edentate | 3 | 3 | 3 | 3 |
|  | Magnesium stearate | 1 | 1 | 1 | 1 |
|  | Toluene-2,5-diamine sulfate | 3 | 3 | 3 | 3 |
| (C) | Sodium lauryl sulfate | 5 | 5 | 5 | — |
| (B) | Stearyl trimethyl ammonium chloride | — | — | — | — |
|  | Sucrose fatty acid ester | — | — | — | 5 |
|  | Carboxymethylcellulose | 15 | 15 | 15 | 15 |
|  | Sodium sulfate | Remainder | Remainder | Remainder | Remainder |
|  | Total | 100 | 100 | 100 | 100 |
|  | Second agent |  |  |  |  |
|  | 35% hydrogen peroxide | 15 | 15 | 15 | 15 |
| (A) | Coconut oil fatty acid amidopropyl betaine | 2.4 | 2.4 | 2.4 | 2.4 |
|  | POE(5) lauryl ether | 0.5 | 0.5 | 0.5 | 0.5 |
| (B) | Stearyl trimethyl ammonium chloride | — | — | — | 1 |
|  | Sodium lauryl sulfate | 1 | — | — | — |
|  | POE(5.5) cetyl ether | — | 1 | — | — |

TABLE 6-continued

|  | Reference Example 3-1 | Reference Example 3-2 | Reference Example 3-3 | Reference Example 3-4 |
|---|---|---|---|---|
| Dimethyl diallyl ammonium chloride-acrylic acid copolymer | — | — | 1 | — |
| Purified water | Remainder | Remainder | Remainder | Remainder |
| Total | 100 | 100 | 100 | 100 |
| Mixing ratio (first agent:second agent) | 1:5 | 1:5 | 1:5 | 1:5 |
| Content of (C) in use | 1.7 | 0.8 | 0.8 | — |
| Content of (B) in use | — | — | — | 0.8 |
| Mass ratio (C)/(B) | — | — | — | — |
| Evaluation for foamability | 3 | 3 | 3 | 2 |
| Evaluation for durability of foam | 1 | 1 | 1 | 1 |

TABLE 7

|  |  | Example 3-9 | Example 3-10 | Example 3-11 | Example 3-12 | Example 3-13 | Example 3-14 | Example 3-15 | Example 3-16 |
|---|---|---|---|---|---|---|---|---|---|
|  | First Agent |  |  |  |  |  |  |  |  |
|  | Ammonium sulfate | 15 | 15 | 15 | 15 | 15 | 15 | 15 | 15 |
|  | Sodium carbonate | 30 | 30 | 30 | 30 | 30 | 30 | 30 | 30 |
|  | Disodium edetate | 3 | 3 | 3 | 3 | 3 | 3 | 3 | 3 |
|  | Magnesium stearate | 1 | 1 | 1 | 1 | 1 | 1 | 1 | 1 |
|  | Toluene-2,5-diamine sulfate | 3 | 3 | 3 | 3 | 3 | 3 | 3 | 3 |
| (C) | Sodium lauryl sulfate | 1.25 | 2 | 5 | 5 | 5 | 5 | 5 | 5 |
|  | Carboxymethylcellulose | 15 | 15 | 15 | 15 | 15 | 15 | 15 | 15 |
|  | Sodium sulfate | Remainder | Remainder | Remainder | Remainder | Remainder | Remainder | Remainder | Remainder |
|  | Total | 100 | 100 | 100 | 100 | 100 | 100 | 100 | 100 |
|  | Second agent |  |  |  |  |  |  |  |  |
|  | 35% hydrogen peroxide | 15 | 15 | 15 | 15 | 15 | 15 | 15 | 15 |
| (A) | Coconut oil fatty acid amidopropyl betaine | 2.4 | 2.4 | 2.4 | 2.4 | 2.4 | 2.4 | 2.4 | 2.4 |
|  | POE(5) lauryl ether | 0.5 | 0.5 | 0.5 | 0.5 | 0.5 | 0.5 | 0.5 | 0.5 |
| (B) | Stearyl trimethyl ammonium chloride | 1 | 1 | 0.33 | 0.5 | 0.65 | 1.2 | 2 | 3 |
|  | Purified water | Remainder | Remainder | Remainder | Remainder | Remainder | Remainder | Remainder | Remainder |
|  | Total | 100 | 100 | 100 | 100 | 100 | 100 | 100 | 100 |
|  | Mixing ratio (first agent:second agent) | 1:5 | 1:5 | 1:5 | 1:5 | 1:5 | 1:5 | 1:5 | 1:5 |
|  | Content of (C) in use | 0.2 | 0.3 | 0.8 | 0.8 | 0.8 | 0.8 | 0.8 | 0.8 |
|  | Content of (B) in use | 0.8 | 0.8 | 0.3 | 0.4 | 0.5 | 1.0 | 1.7 | 2.5 |
|  | Mass ratio (C)/(B) | 0.25 | 0.4 | 3.0 | 2.0 | 1.5 | 0.8 | 0.5 | 0.3 |
|  | Evaluation for foamability | 5 | 5 | 5 | 5 | 5 | 5 | 5 | 4 |
|  | Evaluation for durability of foam | 3 | 4 | 4 | 4 | 5 | 5 | 5 | 3 |

TABLE 8

|  |  | Example 3-17 | Example 3-18 | Example 3-19 | Example 3-20 | Example 3-21 | Example 3-22 | Example 3-23 | Example 3-24 |
|---|---|---|---|---|---|---|---|---|---|
|  | First agent |  |  |  |  |  |  |  |  |
|  | Ammonium sulfate | 15 | 15 | 15 | 15 | 15 | 15 | 15 | 25 |
|  | Sodium carbonate | 30 | 30 | 30 | 30 | 30 | 30 | 30 | 40 |
|  | Disodium edetate | 3 | 3 | 3 | 3 | 3 | 3 | 3 | 3 |
|  | Magnesium stearate | 1 | 1 | 1 | 1 | 1 | 1 | 1 | 1 |
|  | Toluene-2,5-diamine sulfate | 3 | 3 | 3 | 3 | 3 | 3 | 3 | 3 |
| (C) | Sodium lauryl sulfate | 7.5 | 7.5 | 7.5 | 7.5 | 7.5 | 7.5 | 10 | 5 |
|  | Carboxymethylcellulose | 15 | 15 | 15 | 15 | 15 | 15 | 15 | 15 |
|  | Sodium sulfate | Remainder | Remainder | Remainder | Remainder | Remainder | Remainder | Remainder | Remainder |
|  | Total | 100 | 100 | 100 | 100 | 100 | 100 | 100 | 100 |
|  | Second agent |  |  |  |  |  |  |  |  |
|  | 35% hydrogen peroxide | 15 | 15 | 15 | 15 | 15 | 15 | 15 | 15 |
| (A) | Coconut oil fatty acid amidopropyl betaine | 2.4 | 2.4 | 2.4 | 2.4 | 2.4 | 2.4 | 2.4 | 2.4 |
|  | POE(5) lauryl ether | 0.5 | 0.5 | 0.5 | 0.5 | 0.5 | 0.5 | 0.5 | 0.5 |
| (B) | Stearyl trimethyl ammonium chloride | 0.5 | 0.75 | 1 | 2 | 3 | 5 | 1 | 1 |
|  | Purified water | Remainder | Remainder | Remainder | Remainder | Remainder | Remainder | Remainder | Remainder |
|  | Total | 100 | 100 | 100 | 100 | 100 | 100 | 100 | 100 |
|  | Mixing ratio (first agent:second agent) | 1:5 | 1:5 | 1:5 | 1:5 | 1:5 | 1:5 | 1:5 | 1:5 |

TABLE 8-continued

|  | Example 3-17 | Example 3-18 | Example 3-19 | Example 3-20 | Example 3-21 | Example 3-22 | Example 3-23 | Example 3-24 |
|---|---|---|---|---|---|---|---|---|
| Content of (C) in use | 1.3 | 1.3 | 1.3 | 1.3 | 1.3 | 1.3 | 1.7 | 0.8 |
| Content of (B) in use | 0.4 | 0.6 | 0.8 | 1.7 | 2.5 | 4.2 | 0.8 | 0.8 |
| Mass ratio (C)/(B) | 3.0 | 2.0 | 1.5 | 0.8 | 0.5 | 0.3 | 2.0 | 1.0 |
| Evaluation for foamability | 4 | 5 | 5 | 5 | 5 | 5 | 4 | 5 |
| Evaluation for durability of foam | 3 | 5 | 5 | 5 | 4 | 4 | 4 | 5 |

Each Example shown in Table 5 was given a score 4 or higher in both the evaluation results for foamability and durability of foam. As shown in Table 6, Reference Examples 3-1 to 3-4 were given a score 1 in the evaluation result for durability of foam.

In Reference Examples 3-1 to 3-3, the second agent did not contain a cationic surfactant, though the first agent contained an anionic surfactant. In Reference Example 3-1, the cationic surfactant contained in the second agent of Example 3-1 was changed to an anionic surfactant. In Reference Example 3-2, the cationic surfactant contained in the second agent of Example 3-1 was changed to a nonionic surfactant POE (5.5) cetyl ether. In Reference Example 3-3, the cationic surfactant contained in the second agent of Example 3-1 was changed to a cationic polymer dimethyl diallyl ammonium chloride-acrylic acid copolymer. In Reference Example 3-4, the anionic surfactant contained in the first agent of Example 3-1 was changed to a nonionic surfactant sucrose fatty acid ester.

These results of Examples and Reference Examples demonstrated the superiority of such constitution that the anionic surfactant and the cationic surfactant are separate until use and come into contact with each other in use.

As shown in Tables 7 and 8, the results better than those of Reference Examples are easily obtained by allowing the mass ratio of the anionic surfactant to the cationic surfactant to fall within the range of 0.25 to 3.

Test 4

Hair dyes of Examples 4-1 to 4-12 and Reference Examples 4-1 and 4-2 comprising a powdery first agent and a liquid second agent containing components shown in Tables 9 and 10 were prepared. In Tables 9 and 10, units for the numeric values representing the content of each component in the hair dyes are % by mass.

First, the first and second agents in the hair dye of each of Examples and Reference Examples were added to the same sealable container as the container 20 shown in FIGS. 1(*a*) to 2. This container was tightly closed and shaken approximately 20 to 30 times for shaking the mixture of the first and second agents in the container to obtain a foamy hair dye. The obtained foamy hair dye was taken in gloved hand, applied to a bundle of human black hair, and then left at room temperature (25° C.) for 30 minutes. Then, the hair dye attached to the hair bundle was washed off with water, and the hair bundle was shampooed two times and treated with a hair conditioner once. Subsequently, the hair bundle was dried in hot air and then left for 1 day to obtain a dyed hair bundle.

The foamy hair dyes obtained by foaming the hair dyes of Examples 4-1 to 4-12 and Reference Examples 4-1 and 4-2 were evaluated for the homogeneity of foam, the elasticity of foam, and miscibility according to the methods shown below. They were also evaluated for the texture of the hair bundle during the wash off of the hair dye and the uniform dyeability of the obtained hair bundle according to the methods shown below. The results are shown in Tables 9 and 10.

<Homogeneity of Foam>

The obtained foamy hair dye was left for 10 minutes in a sealable container and evaluated for the quality of foam positioned in the upper and lower portions of the sealable container by observation by expert panelists with the touch of hand on the foam in the "Homogeneity of foam" columns of Tables 9 and 10, the score "5" indicates that there is no difference in foam quality between the positions; the score "4" indicates that there is little difference in foam quality between the positions; the score "3" indicates that there is not much difference in foam quality between the positions; the score "2" indicates that there is difference in foam quality between the positions; and the score "1" indicates that there is large difference in foam quality between the positions.

<Elasticity of Foam>

The obtained foamy hair dye was evaluated for elasticity by observation by expert panelists with the touch of hand on the foam. In the "Elasticity of foam" columns of Tables 9 and 10, the score "5" indicates that the foam does not lose its shape when taken in hand (the foam pushes back when pressed); the score "4" indicates that the foam insubstantially loses its shape when taken in hand; the score "3" indicates that the foam does not lose much shape when taken in hand; the score "2" indicates that the foam loses its shape when taken in hand; and the score "1" indicates that the foam loses much shape when taken in hand (the foam does not push back when pressed).

<Miscibility>

The obtained foamy hair dye was evaluated for the miscibility between the powdery first agent and the liquid second agent by visually observing for the presence or absence of an unmixed-in lump of powder by expert panelists. In the "Miscibility of foam" columns of Tables 9 and 10, the score "5" indicates that there is no unmixed-in lump of powder (sufficiently mixed); the score "4" indicates that there are few unmixed-in lumps of powders; the score "3" indicates that there is not much unmixed-in lump of powder; the score "2" indicates that there are noticeable unmixed-in lumps of powder; and the score "1" indicates that there are many noticeable unmixed-in lumps of powder (unmixed).

<Hair Texture (Stickiness)>

The texture of the hair bundle (hair) during the wash off of the hair dye was evaluated by observation by expert panelists with the touch of hand on the hair bundle. In the "Hair texture (stickiness)" columns of Tables 9 and 10, the score "5" indicates that there is no stickiness; the score "4" indicates that there is little stickiness; the score "3" indicates that there is not: much stickiness; the score "2" indicates that there is perceivable stickiness; and the score "1" indicates that there is strongly perceivable stickiness.

<Uniform Dyeability>

The dyed hair bundle was evaluated for uniform dyeability by visual observation under standard light, source by expert panelists. In the "Uniform dyeability" columns of Tables 9 and 10, the score "5" indicates that there is no non-uniformity of dyeing; the score "4" indicates that there is little non-uniformity of dyeing; the score "3" indicates that there is not much non-uniformity of dyeing; the score "2" indicates that there is noticeable non-uniformity of dyeing; and the score "1" indicates that there is very noticeable non-uniformity of dyeing.

TABLE 9

|  |  | Example 4-1 | Example 4-2 | Example 4-3 | Example 4-4 | Example 4-5 | Example 4-6 | Example 4-7 |
|---|---|---|---|---|---|---|---|---|
| | First agent (powdery) | | | | | | | |
| | Ammonium sulfate | 15 | 15 | 15 | 15 | 15 | 15 | 15 |
| | Sodium carbonate | 30 | 30 | 30 | 30 | 30 | 30 | 30 |
| | Disodium edetate | 3 | 3 | 3 | 3 | 3 | 3 | 3 |
| | Magnesium stearate | 1 | 1 | 1 | 1 | 1 | 1 | 1 |
| | Toluene-2,5-diamine sulfate | 3 | 3 | 3 | 3 | 3 | 3 | 3 |
| (C) | Sodium lauryl sulfate | 5 | 5 | 5 | 5 | 5 | 5 | 5 |
| (D) | Potato starch | 30 | | | 15 | 25 | 15 | 25 |
| (D) | Cyclodextrin | | 30 | | 15 | 5 | | |
| (D) | Hydroxyethylcellulose | | | 30 | | | 15 | 5 |
| | Carboxymethylcellulose | | | | | | | |
| | Hydroxyethylcellulose dimethyl diallyl ammonium chloride | | | | | | | |
| | Sodium sulfate | Remainder | Remainder | Remainder | Remainder | Remainder | Remainder | Remainder |
| | Total | 100 | 100 | 100 | 100 | 100 | 100 | 100 |
| | Second agent (liquid) | | | | | | | |
| | 35% hydrogen peroxide | 15 | 15 | 15 | 15 | 15 | 15 | 15 |
| (A) | Coconut oil fatty acid amidopropyl betaine | 2.4 | 2.4 | 2.4 | 2.4 | 2.4 | 2.4 | 2.4 |
| | POE(5) lauryl ether (nonionic surfactant) | 0.5 | 0.5 | 0.5 | 0.5 | 0.5 | 0.5 | 0.5 |
| (B) | Stearyl trimethyl ammonium chloride | 1 | 1 | 1 | 1 | 1 | 1 | 1 |
| | Purified water | Remainder | Remainder | Remainder | Remainder | Remainder | Remainder | Remainder |
| | Total | 100 | 100 | 100 | 100 | 100 | 100 | 100 |
| | First agent:second agent mixing ratio (mass ratio) | 1:5 | 1:5 | 1:5 | 1:5 | 1:5 | 1:5 | 1:5 |
| | Amount of component D incorporated in use | 5.0 | 5.0 | 5.0 | 5.0 | 5.0 | 5.0 | 5.0 |
| | Amount of all surfactants incorporated in use | 4.1 | 4.1 | 4.1 | 4.1 | 4.1 | 4.1 | 4.1 |
| Evaluation | Homogeneity of foam | 4 | 4 | 3 | 5 | 5 | 4 | 5 |
| | Miscibility | 5 | 5 | 4 | 5 | 5 | 5 | 5 |
| | Hair texture (stickiness) | 5 | 5 | 5 | 5 | 5 | 5 | 5 |
| | Uniform dyeability | 4 | 4 | 3 | 5 | 5 | 4 | 5 |
| | Elasticity of foam | 5 | 5 | 3 | 5 | 5 | 4 | 5 |

TABLE 10

|  |  | Example 4-8 | Example 4-9 | Example 4-10 | Example 4-11 | Example 4-12 | Example 4-13 | Example 4-14 | Reference Example 4-1 | Reference Example 4-2 |
|---|---|---|---|---|---|---|---|---|---|---|
| | First agent (powdery) | | | | | | | | | |
| | Ammonium sulfate | 15 | 15 | 15 | 15 | 15 | 15 | 15 | 15 | 15 |
| | Sodium carbonate | 30 | 30 | 30 | 30 | 30 | 30 | 30 | 30 | 30 |
| | Disodium edetate | 3 | 3 | 3 | 3 | 3 | 3 | 3 | 3 | 3 |
| | Magnesium stearate | 1 | 1 | 1 | 1 | 1 | 1 | 1 | 1 | 1 |
| | Toluene-2,5-diamine sulfate | 3 | 3 | 3 | 3 | 3 | 3 | 3 | 3 | 3 |
| (C) | Sodium lauryl sulfate | 5 | 5 | 5 | 3.2 | 4 | 7.2 | 7.9 | 5 | 5 |
| (D) | Potato starch | 1.6 | 6.3 | 36 | 25 | 25 | 25 | 25 | | |
| (D) | Cyclodextrin | 0.3 | 1.3 | 7 | 5 | 5 | 5 | 5 | | |
| (D) | Hydroxyethylcellulose | | | | | | | | | |
| | Carboxymethylcellulose | | | | | | | | 30 | |
| | Hydroxyethylcellulose dimethyl diallyl ammonium chloride | | | | | | | | | 30 |
| | Sodium sulfate | Remainder | Remainder | | Remainder | Remainder | Remainder | Remainder | Remainder | Remainder |
| | Total | 100 | 100 | 100 | 100 | 100 | 100 | 100 | 100 | 100 |
| | Second agent (liquid) | | | | | | | | | |
| | 35% hydrogen peroxide | 15 | 15 | 15 | 15 | 15 | 15 | 15 | 15 | 15 |
| (A) | Coconut oil fatty acid amidopropyl betaine | 2.4 | 2.4 | 2.4 | 0.9 | 2 | 4 | 8 | 2.4 | 2.4 |
| | POE(5) lauryl ether (nonionic surfactant) | 0.5 | 0.5 | 0.5 | 0.32 | 0.4 | 0.7 | 0.8 | 0.5 | 0.5 |
| (B) | Stearyl trimethyl ammonium chloride | 1 | 1 | 1 | 0.64 | 0.8 | 1.4 | 1.6 | 1 | 1 |
| | Purified water | Remainder | Remainder | Remainder | Remainder | Remainder | Remainder | Remainder | Remainder | Remainder |
| | Total | 100 | 100 | 100 | 100 | 100 | 100 | 100 | 100 | 100 |
| | First agent:second agent mixing ratio (mass ratio) | 1:5 | 1:5 | 1:5 | 1:5 | 1:5 | 1:5 | 1:5 | 1:5 | 1:5 |

TABLE 10-continued

|  |  | Example 4-8 | Example 4-9 | Example 4-10 | Example 4-11 | Example 4-12 | Example 4-13 | Example 4-14 | Reference Example 4-1 | Reference Example 4-2 |
|---|---|---|---|---|---|---|---|---|---|---|
|  | Amount of component D incorporated in use | 0.3 | 1.3 | 7.2 | 5.0 | 5.0 | 5.0 | 5.0 | — | — |
|  | Amount of all surfactants incorporated in use | 4.1 | 4.1 | 4.1 | 2.1 | 3.3 | 6.3 | 10.0 | 4.1 | 4.1 |
| Evaluation | Homogeneity of foam | 3 | 4 | 5 | 4 | 4 | 4 | 4 | 1 | 1 |
|  | Miscibility | 3 | 4 | 5 | 4 | 5 | 5 | 3 | 1 | 1 |
|  | Hair texture (stickiness) | 5 | 5 | 5 | 5 | 5 | 4 | 3 | 5 | 5 |
|  | Uniform dyeability | 3 | 4 | 5 | 4 | 4 | 4 | 4 | 1 | 1 |
|  | Elasticity of foam | 3 | 4 | 5 | 3 | 5 | 5 | 3 | 3 | 1 |

As shown in Tables 9 and 10, each Example containing a nonionic polymer produced favorable evaluation results for all the evaluation items. Particularly, it was demonstrated that Examples 4-1 and 4-2 containing, as a nonionic polymer, starch or cyclodextrin, which was oligosaccharide or polysaccharide comprising an α-glucose compound as a constituent unit, were more highly regarded than Example 4-3 containing a different nonionic polymer in the evaluation results for the homogeneity of foam, the elasticity of foam, miscibility, and uniform dyeability. Moreover, it was demonstrated that Examples 4-4 and 4-5 containing two kinds of nonionic polymers were more highly regarded than Examples 4-1 and 4-2 containing one kind of nonionic polymer in the same amount in the evaluation results for the homogeneity of foam and uniform dyeability.

On the other hand, it was demonstrated that Reference Example 4-1 containing an anionic polymer instead of a nonionic polymer was less regarded than Examples in the evaluation results for the homogeneity of foam, miscibility, and uniform dyeability. Moreover, it was demonstrated that Reference Example 4-2 containing a cationic polymer instead of a nonionic polymer was less regarded than Examples in the evaluation results for the homogeneity of foam, the elasticity of foam, miscibility, and uniform dyeability.

Test 5

Examples 5-1 to 5-5 and Reference Examples 5-1 to 5-3

Oxidation hair dyes of Example 5-1 to 5-5 and Reference Examples 5-1 to 5-3 were prepared. These oxidation hair dyes were a two-part type comprising a powdery first agent and a liquid second agent. The first and second agents had the compositions shown in Table 11. In Table 11 and subsequent Tables 12 and 13, units for the numeric values representing the content of each component in the oxidation hair dyes are % by mass.

Next, the oxidation hair dye of each of Examples and Reference Examples was foamed using the same sealable container as the container 20 shown in FIGS. 1(a) to 2. The sealable container used had a capacity of 770 mL, a height of 17 cm, and an inside diameter of 7 to 2 cm. To this container, 150 g of the mixture of the first and second agents was added, and the container was shaken up and down 20 times. The mixture of the first and second agents was thus shaken up with air to obtain an oxidation hair dye in a foamy form.

Examples 5-6 to 5-17

An oxidation hair dye in a foamy form was obtained in the same way as in Example 5-1 from oxidation hair dyes differing in the content of at least one of the ammonium cationic surfactant having an alkyl group with 16 or more and 22 or less carbon atoms as a component b-1 and the ammonium cationic surfactant having an alkyl group with 10 or more and less than 16 carbon atoms as a component b-2 from the composition of the oxidation hair dye of Example 5-1.

<Evaluation for Operability>

Expert panelists placed the oxidation hair dye of each of Examples and Reference Examples on their hands and then lifted part of the oxidation hair dye. The stringy state and the state in which the foam was separated were visually observed. The results were evaluated according to the following evaluation criteria.

5: The foam is not stringy and is excellent in separation.
4: The foam is insignificantly stringy and is good in separation.
3: The foam is slightly stringy, but is favorably separated.
2: The foam is stringy and is slightly poorly separated.
1: The foam is very stringy and is poorly separated.

Numeric values of the evaluation results are shown in the "Evaluation for handleability" columns of Tables 11 to 13.

<Evaluation for Applicability>

Expert panelists applied the oxidation hair dye of each of Examples and Reference Examples to their hair and evaluated this status according to the following evaluation criteria.

5: Spread on hair and adhesion to hair are excellent.
4: Spread on hair and adhesion to hair are good.
3: Spread on hair and adhesion to hair are favorable.
2: Spread on hair or adhesion to hair is slightly poor.
1: Spread on hair or adhesion to hair is poor.

Numeric values of the evaluation results are shown in the "Evaluation for applicability" columns of Tables 11 to 13.

<Evaluation of Hair Texture>

The oxidation hair dye of each of Examples and Reference Examples was applied to a hair bundle and left for the predetermined time, and then the hair bundle was washed with hot water for washing off the hair dye, to carry out the dyeing stage. Expert panelists conducted sensory evaluation according to the following evaluation criteria for the texture of the hair bundle when the hair bundle was washed with hot water (during wash off) and the texture of the hair bundle after drying with a drier (after finish).

5: There is not perceivable stickiness during wash off and after finish.
4: There is little perceivable stickiness during wash off and after finish.
3: There is slightly perceivable stickiness during wash off or after finish.
2: There is perceivable stickiness during wash off or after finish.
1: There is perceivable stickiness during wash off and after finish.

Numeric values of the evaluation results are shown in the "Evaluation of hair texture" columns of Tables 11 to 13.

TABLE 11

|  |  | Example 5-1 | Example 5-2 | Example 5-3 | Example 5-4 | Example 5-5 | Reference Example 5-1 | Reference Example 5-2 | Reference Example 5-3 |
|---|---|---|---|---|---|---|---|---|---|
|  | First agent |  |  |  |  |  |  |  |  |
|  | Ammonium sulfate | 15 | 15 | 15 | 15 | 15 | 15 | 15 | 15 |
|  | Sodium carbonate | 30 | 30 | 30 | 30 | 30 | 30 | 30 | 30 |
|  | Disodium edetate | 3 | 3 | 3 | 3 | 3 | 3 | 3 | 3 |
|  | Magnesium stearate | 1 | 1 | 1 | 1 | 1 | 1 | 1 | 1 |
|  | Toluene-2,5-diamine sulfate | 3 | 3 | 3 | 3 | 3 | 3 | 3 | 3 |
| (C) | Sodium lauryl sulfate | 5 | 5 | 5 | 17 | — | 5 | 5 | 5 |
|  | Sucrose fatty acid ester | — | — | — | — | 5 | — | — | — |
|  | Carboxymethylcellulose | 15 | 15 | 15 | 15 | 15 | 15 | 15 | 15 |
|  | Sodium sulfate | Remainder | Remainder | Remainder | Remainder | Remainder | Remainder | Remainder | Remainder |
|  | Total | 100 | 100 | 100 | 100 | 100 | 100 | 100 | 100 |
|  | Second agent |  |  |  |  |  |  |  |  |
|  | 35% hydrogen peroxide | 15 | 15 | 15 | 15 | 15 | 15 | 15 | 15 |
| (A) | Coconut oil fatty acid amidopropyl betaine | 2.4 | 2.4 | 2.4 | — | 2.4 | 2.4 | 2.4 | 2.4 |
|  | POE(5) lauryl ether | 0.5 | 0.5 | 0.5 | 0.5 | 0.5 | 0.5 | 0.5 | 0.5 |
| (b-1) | Stearyl trimethyl ammonium chloride (C18) | — | — | 0.50 | — | — | — | — | 1.00 |
| (b-1) | Distearyl dimethyl ammonium chloride (C18) | — | 0.50 | — | — | — | — | — | — |
| (b-1) | Cetyl trimethyl ammonium chloride (C16) | 0.50 | — | — | 0.50 | 0.50 | — | 1.50 | 0.50 |
| (b-2) | Lauryl trimethyl ammonium chloride (C12) | 1.00 | 1.00 | 1.00 | 1.00 | 1.00 | 1.50 | — | — |
|  | Purified water | Remainder | Remainder | Remainder | Remainder | Remainder | Remainder | Remainder | Remainder |
|  | Total | 100 | 100 | 100 | 100 | 100 | 100 | 100 | 100 |
|  | Mixing ratio (first agent:second agent) | 1:5 | 1:5 | 1:5 | 1:5 | 1:5 | 1:5 | 1:5 | 1:5 |
|  | Content of (b-1) in use | 0.4 | 0.4 | 0.4 | 0.4 | 0.4 | — | 1.3 | 1.3 |
|  | Content of (b-2) in use | 0.8 | 0.8 | 0.8 | 0.8 | 0.8 | 1.3 | — | — |
|  | Mass ratio = (b-2)/(b-1) | 2 | 2 | 2 | 2 | 2 | — | — | — |
|  | Evaluation for operability | 5 | 4 | 4 | 4 | 4 | 3 | 1 | 1 |
|  | Evaluation for applicability | 5 | 5 | 5 | 4 | 4 | 1 | 3 | 3 |
|  | Evaluation of hair texture | 5 | 5 | 5 | 5 | 5 | 5 | 5 | 5 |

TABLE 12

|  |  | Example 5-6 | Example 5-7 | Example 5-8 | Example 5-9 | Example 5-10 | Example 5-11 |
|---|---|---|---|---|---|---|---|
|  | First agent |  |  |  |  |  |  |
|  | Ammonium sulfate | 15 | 15 | 15 | 15 | 15 | 15 |
|  | Sodium carbonate | 30 | 30 | 30 | 30 | 30 | 30 |
|  | Disodium edetate | 3 | 3 | 3 | 3 | 3 | 3 |
|  | Magnesium stearate | 1 | 1 | 1 | 1 | 1 | 1 |
|  | Toluene-2,5-diamine sulfate | 3 | 3 | 3 | 3 | 3 | 3 |
| (C) | Sodium lauryl sulfate | 5 | 5 | 5 | 5 | 5 | 5 |
|  | Carboxymethylcellulose | 15 | 15 | 15 | 15 | 15 | 15 |
|  | Sodium sulfate | Remainder | Remainder | Remainder | Remainder | Remainder | Remainder |
|  | Total | 100 | 100 | 100 | 100 | 100 | 100 |
|  | Second agent |  |  |  |  |  |  |
|  | 35% hydrogen peroxide | 15 | 15 | 15 | 15 | 15 | 15 |
| (A) | Coconut oil fatty acid amidopropyl betaine | 2.4 | 2.4 | 2.4 | 2.4 | 2.4 | 2.4 |
|  | POE(5) lauryl ether | 0.5 | 0.5 | 0.5 | 0.5 | 0.5 | 0.5 |
| (b-1) | Cetyl trimethyl ammonium chloride (C16) | 0.10 | 0.25 | 0.75 | 1.00 | 1.25 | 1.40 |
| (b-2) | Lauryl trimethyl ammonium chloride (C12) | 1.40 | 1.25 | 0.75 | 0.50 | 0.25 | 0.10 |
|  | Purified water | Remainder | Remainder | Remainder | Remainder | Remainder | Remainder |
|  | Total | 100 | 100 | 100 | 100 | 100 | 100 |
|  | Mixing ratio (first agent:second agent) | 1:5 | 1:5 | 1:5 | 1:5 | 1:5 | 1:5 |
|  | Content of (b-1) in use | 0.1 | 0.2 | 0.6 | 0.8 | 1.0 | 1.2 |
|  | Content of (b-2) in use | 1.2 | 1.0 | 0.6 | 0.4 | 0.2 | 0.1 |
|  | Mass ratio = (b-2)/(b-1) | 14 | 5 | 1 | 0.5 | 0.2 | 0.07 |
|  | Evaluation for operability | 5 | 5 | 5 | 4 | 3 | 3 |

TABLE 12-continued

|  | Example 5-6 | Example 5-7 | Example 5-8 | Example 5-9 | Example 5-10 | Example 5-11 |
|---|---|---|---|---|---|---|
| Evaluation for applicability | 3 | 4 | 5 | 5 | 5 | 5 |
| Evaluation of hair texture | 5 | 5 | 5 | 5 | 5 | 5 |

TABLE 13

|  |  | Example 5-12 | Example 5-13 | Example 5-14 | Example 5-15 | Example 5-16 | Example 5-17 |
|---|---|---|---|---|---|---|---|
|  | First agent |  |  |  |  |  |  |
|  | Ammonium sulfate | 15 | 15 | 15 | 15 | 15 | 15 |
|  | Sodium carbonate | 30 | 30 | 30 | 30 | 30 | 30 |
|  | Disodium edetate | 3 | 3 | 3 | 3 | 3 | 3 |
|  | Magnesium stearate | 1 | 1 | 1 | 1 | 1 | 1 |
|  | Toluene-2,5-diamine sulfate | 3 | 3 | 3 | 3 | 3 | 3 |
| (C) | Sodium lauryl sulfate | 5 | 5 | 5 | 5 | 5 | 5 |
|  | Carboxymethylcellulose | 15 | 15 | 15 | 15 | 15 | 15 |
|  | Sodium sulfate | Remainder | Remainder | Remainder | Remainder | Remainder | Remainder |
|  | Total | 100 | 100 | 100 | 100 | 100 | 100 |
|  | Second agent |  |  |  |  |  |  |
|  | 35% hydrogen peroxide | 15 | 15 | 15 | 15 | 15 | 15 |
| (A) | Coconut oil fatty acid amidopropyl betaine | 2.4 | 2.4 | 2.4 | 2.4 | 2.4 | 2.4 |
|  | POE(5) lauryl ether | 0.5 | 0.5 | 0.5 | 0.5 | 0.5 | 0.5 |
| (b-1) | Cetyl trimethyl ammonium chloride (C16) | 0.10 | 0.25 | 0.75 | 1.50 | 3.00 | 6.00 |
| (b-2) | Lauryl trimethyl ammonium chloride (C12) | 0.20 | 0.50 | 1.50 | 3.00 | 6.00 | 12.00 |
|  | Purified water | Remainder | Remainder | Remainder | Remainder | Remainder | Remainder |
|  | Total | 100 | 100 | 100 | 100 | 100 | 100 |
|  | Mixing ratio (first agent:second agent) | 1:5 | 1:5 | 1:5 | 1:5 | 1:5 | 1:5 |
|  | Content of (b-1) in use | 0.1 | 0.2 | 0.6 | 1.3 | 2.5 | 5.0 |
|  | Content of (b-2) in use | 0.2 | 0.4 | 1.3 | 2.5 | 5.0 | 10.0 |
|  | Mass ratio = (b-2)/(b-1) | 2 | 2 | 2 | 2 | 2 | 2 |
|  | Evaluation for operability | 3 | 4 | 5 | 5 | 4 | 3 |
|  | Evaluation for applicability | 3 | 4 | 5 | 5 | 4 | 4 |
|  | Evaluation of hair texture | 5 | 5 | 5 | 5 | 3 | 3 |

As shown in Table 11, Examples 5-1 to 5-5 were given a score 4 or higher in the results for operability, applicability, and hair texture. Reference Examples 5-1 to 5-3 were given a score 1 in the results for either of operability or applicability.

Reference Example 5-1 did not contain a (b-1) ammonium cationic surfactant having an alkyl group with 16 or more and 22 or less carbon atoms. Reference Example 5-2 did not contain a (b-2) ammonium cationic surfactant having an alkyl group with 10 or more and less than 16 carbon atoms. Reference Example 5-3 produced results inferior to those of Examples for applicability, though it contained two kinds of (b-1) ammonium cationic surfactants having an alkyl group with 16 or more and 22 or less carbon atoms (these surfactants differed in the number of carbon atoms in the alkyl chain).

As shown in Table 12, it was demonstrated that it became easier to enhance both effects for operability and applicability by allowing the mass ratio of the (b-2) ammonium cationic surfactant having an alkyl group with 10 or more and less than 16 carbon atoms to the (b-1) ammonium cationic surfactant having an alkyl group with 16 or more and 22 or less carbon atoms to fall within the predetermined range. As shown in Table 13, it was demonstrated that it became easier to enhance effects of operability, applicability, and hair texture by adjusting the contents of the (b-1) ammonium cationic surfactant having an alkyl group with 16 or more and 22 or less carbon atoms and the (b-2) ammonium cationic surfactant having an alkyl group with 10 or more and less than 16 carbon atoms.

The first and second agents of Examples 5-1 to 5-4 and 5-6 to 5-17 had favorable foamability at the foaming stage and maintained the foamy form for a given time without causing the disappearance (break) of foam immediately after foaming. Therefore, the foamy form was sufficiently maintained at the dyeing stage.

Test 6-1

Hair bleaches of Examples 6-1 to 6-24 and Reference Examples 6-1 to 6-4 comprising a powdery first agent and an emulsion second agent containing components shown in Tables 14 and 15 were prepared in Tables 14 and 15, units for the numeric values representing the content of each component in the hair bleaches are by mass. Then, the first and second agents were mixed at a mass ratio of 14 and stirred using a stirring rod to prepare a hair bleach. The obtained hair bleach was evaluated for the rate of onset of a thickening effect and viscosity stability. The results are shown in Tables 14 and 15.

In Tables 14 and 15, the "Mass ratio of starch" represents the mass ratio of the content of the starch to that of the thickener in use.

In Tables 14 and 15, the "Mass ratio of anionic surfactant" represents the mass ratio of the content of the anionic surfactant (component C) to that of the cationic surfactant (component B) in use.

<Measurement and Evaluation of Rate of Onset of Thickening Effect>

The viscosity of the hair bleach obtained by mixing was measured every 1 minute during and after the mixing of the first and second agents under conditions involving Rotor No. 4, the number of revolutions of 12 rpm, 25° C., and 1 minute using a type B viscometer.

In the "Rate of onset of thickening effect" columns of Tables 14 and 15, the score "5" represents 1000 mPa·s/min. or higher as the rate of rise in viscosity from the mixing of the first and second agents to 3 minutes later; the score "4" represents 850 mPa·s/min. or more and less than 1000 mPa·s/min.; the score "3" represents 650 mPa·s/min. or more and less than 850 mPa·s/min.; the score "2" represents 500 mPa·s/min. or more and less than 650 mPa·s/min.; and the score "1" represents lower than 500 mPa·s/min.

<Viscosity>

The ratio of viscosity (=viscosity after 5 minutes/viscosity after 25 minutes) was calculated from viscosity 5 minutes after the mixing of the first and second agents and viscosity 25 minutes after the mixing of the first and second agents.

This ratio of viscosity was evaluated on a 1-to-5 scale: 0.80 or more and less than 1.20 (excellent: 5); 0.60 or more and less than 0.80 or 1.2 or more and less than 2.0 (good: 4); 0.40 or more and less than 0.60 or 2.0 or more and less than 4.0 (good: 3); 0.20 or more and less than 0.40 or 4.0 or more and less than 6.0 (slightly poor: 2); and less than 0.20 or 6.0 or more (poor: 1).

TABLE 14

| | | Example 6-1 | Example 6-2 | Example 6-3 | Example 6-4 | Example 6-5 | Example 6-6 | Example 6-7 |
|---|---|---|---|---|---|---|---|---|
| | First agent (powdery) | | | | | | | |
| | Potassium persulfate | 20 | 20 | 20 | 20 | 20 | 20 | 20 |
| | Sodium persulfate | 15 | 15 | 15 | 15 | 15 | 15 | 15 |
| | Ammonium persulfate | 10 | 10 | 10 | 10 | 10 | 10 | 10 |
| | Sodium carbonate | | | | | | | |
| | Sodium metasilicate | 10 | 10 | 10 | 10 | 10 | 10 | 10 |
| | Disodium edetate | 3 | 3 | 3 | 3 | 3 | 3 | 3 |
| | Magnesium stearate | 1 | 1 | 1 | 1 | 1 | 1 | 1 |
| (C) | Sodium lauryl sulfate | 1 | | | 1 | 1 | 1 | 0.5 |
| (C) | Sodium cetyl sulfate | | 1 | | | | | |
| (C) | Disodium lauryl sulfosuccinate | | | 1 | | | | 0.5 |
| (c) | Sucrose fatty acid ester | | | | | | | |
| (E) | Carboxymethylcellulose | 5 | 5 | 5 | 5 | 5 | | 5 |
| (E) | Hydroxyethylcellulose | | | | | | 5 | |
| (D) | Potato starch | 20 | 20 | 20 | 20 | 20 | 20 | 20 |
| | Sodium sulfate | Remainder | Remainder | Remainder | Remainder | Remainder | Remainder | Remainder |
| | Total | 100 | 100 | 100 | 100 | 100 | 100 | 100 |
| | Second agent (emulsion) | | | | | | | |
| | 35% hydrogen peroxide | 17 | 17 | 17 | 17 | 17 | 17 | 17 |
| | Cetanol | 0.5 | 0.5 | 0.5 | 0.5 | 0.5 | 0.5 | 0.5 |
| | POE(5) lauryl ether | 0.5 | 0.5 | 0.5 | 0.5 | 0.5 | 0.5 | 0.5 |
| (B) | Stearyl trimethyl ammonium chloride | 0.25 | 0.25 | 0.25 | | | 0.25 | 0.25 |
| (B) | Distearyl dimethyl ammonium chloride | | | | 0.25 | | | |
| (B) | Lauryl trimethyl ammonium chloride | | | | | 0.25 | | |
| (b) | POE(30) cetyl ether | | | | | | | |
| | Purified water | Remainder | Remainder | Remainder | Remainder | Remainder | Remainder | Remainder |
| | Total | 100 | 100 | 100 | 100 | 100 | 100 | 100 |
| | First agent:second agent mixing ratio (mass ratio) | 1:4 | 1:4 | 1:4 | 1:4 | 1:4 | 1:4 | 1:4 |
| | Mass ratio of starch (starch/thickener) | 4 | 4 | 4 | 4 | 4 | 4 | 4 |
| | Mass ratio of anionic surfactant (C/B) | 1 | 1 | 1 | 1 | 1 | 1 | 1 |
| | Evaluation | | | | | | | |
| | Rate of onset of thickening effect | 5 | 5 | 5 | 5 | 5 | 5 | 5 |
| | Viscosity stability | 5 | 5 | 5 | 5 | 5 | 5 | 5 |

| | | Example 6-8 | Example 6-9 | Reference Example 6-1 | Reference Example 6-2 | Reference Example 6-3 | Reference Example 6-4 |
|---|---|---|---|---|---|---|---|
| | First agent (powdery) | | | | | | |
| | Potassium persulfate | 20 | 20 | 20 | 20 | 20 | 20 |
| | Sodium persulfate | 15 | 15 | 15 | 15 | 15 | 15 |
| | Ammonium persulfate | 10 | 10 | 10 | 10 | 10 | 10 |
| | Sodium carbonate | | 5 | | | | |
| | Sodium metasilicate | 10 | 5 | 10 | 10 | 10 | 10 |
| | Disodium edetate | 3 | 3 | 3 | 3 | 3 | 3 |
| | Magnesium stearate | 1 | 1 | 1 | 1 | 1 | 1 |

TABLE 14-continued

|  |  | | | | | | |
|---|---|---|---|---|---|---|---|
| (C) | Sodium lauryl sulfate | 1 | 1 |  | 1 | 1 | 1 |
| (C) | Sodium cetyl sulfate |  |  |  |  |  |  |
| (C) | Disodium lauryl sulfosuccinate |  |  |  |  |  |  |
| (c) | Sucrose fatty acid ester |  |  | 1 |  |  |  |
| (E) | Carboxymethylcellulose | 5 | 5 | 5 | 5 |  | 5 |
| (E) | Hydroxyethylcellulose |  |  |  |  |  |  |
| (D) | Potato starch | 20 | 20 | 20 | 20 | 20 |  |
|  | Sodium sulfate | Remainder | Remainder | Remainder | Remainder | Remainder | Remainder |
|  | Total | 100 | 100 | 100 | 100 | 100 | 100 |
|  | Second agent (emulsion) | | | | | | |
|  | 35% hydrogen peroxide | 17 | 17 | 17 | 17 | 17 | 17 |
|  | Cetanol | 0.5 | 0.5 | 0.5 | 0.5 | 0.5 | 0.5 |
|  | POE(5) lauryl ether | 0.5 | 0.5 | 0.5 | 0.5 | 0.5 | 0.5 |
| (B) | Stearyl trimethyl ammonium chloride | 0.15 | 0.25 | 0.25 |  | 0.25 | 0.25 |
| (B) | Distearyl dimethyl ammonium chloride | 0.1 |  |  |  |  |  |
| (B) | Lauryl trimethyl ammonium chloride |  |  |  |  |  |  |
| (b) | POE(30) cetyl ether |  |  |  | 0.25 |  |  |
|  | Purified water | Remainder | Remainder | Remainder | Remainder | Remainder | Remainder |
|  | Total | 100 | 100 | 100 | 100 | 100 | 100 |
|  | First agent:second agent mixing ratio (mass ratio) | 1:4 | 1:4 | 1:4 | 1:4 | 1:4 | 1:4 |
|  | Mass ratio of starch (starch/thickener) | 4 | 4 | 4 | 4 | — | — |
|  | Mass ratio of anionic surfactant (C/B) | 1 | 1 | — | — | 1 | 1 |
|  | Evaluation | | | | | | |
|  | Rate of onset of thickening effect | 5 | 5 | 1 | 1 | 1 | 2 |
|  | Viscosity stability | 5 | 5 | 1 | 1 | 4 | 2 |

TABLE 15

|  |  | Example 6-10 | Example 6-11 | Example 6-12 | Example 6-13 | Example 6-14 | Example 6-15 | Example 6-16 | Example 6-17 |
|---|---|---|---|---|---|---|---|---|---|
|  | First agent (powdery) | | | | | | | | |
|  | Potassium persulfate | 20 | 20 | 20 | 20 | 20 | 20 | 20 | 20 |
|  | Sodium persulfate | 15 | 15 | 15 | 15 | 15 | 15 | 15 | 15 |
|  | Ammonium persulfate | 10 | 10 | 10 | 10 | 10 | 10 | 10 | 10 |
|  | Sodium metasilicate | 10 | 10 | 10 | 10 | 10 | 10 | 10 | 10 |
|  | Disodium edetate | 3 | 3 | 3 | 3 | 3 | 3 | 3 | 3 |
|  | Magnesium stearate | 1 | 1 | 1 | 1 | 1 | 1 | 1 | 1 |
| (C) | Sodium lauryl sulfate | 1 | 1 | 1 | 1 | 1 | 1 | 1 | 0.1 |
| (E) | Carboxymethylcellulose | 1 | 10 | 20 | 5 | 5 | 5 | 5 | 5 |
| (D) | Potato starch | 20 | 20 | 20 | 2 | 10 | 25 | 35 | 20 |
|  | Sodium sulfate | Remainder | Remainder | Remainder | Remainder | Remainder | Remainder | Remainder | Remainder |
|  | Total | 100 | 100 | 100 | 100 | 100 | 100 | 100 | 100 |
|  | Second agent (emulsion) | | | | | | | | |
|  | 35% hydrogen peroxide | 17 | 17 | 17 | 17 | 17 | 17 | 17 | 17 |
|  | Cetanol | 0.5 | 0.5 | 0.5 | 0.5 | 0.5 | 0.5 | 0.5 | 0.5 |
|  | POE(5) lauryl ether | 0.5 | 0.5 | 0.5 | 0.5 | 0.5 | 0.5 | 0.5 | 0.5 |
| (B) | Stearyl trimethyl ammonium chloride | 0.25 | 0.25 | 0.25 | 0.25 | 0.25 | 0.25 | 0.25 | 0.25 |
|  | Purified water | Remainder | Remainder | Remainder | Remainder | Remainder | Remainder | Remainder | Remainder |
|  | Total | 100 | 100 | 100 | 100 | 100 | 100 | 100 | 100 |
|  | First agent:second agent mixing ratio (mass ratio) | 1:4 | 1:4 | 1:4 | 1:4 | 1:4 | 1:4 | 1:4 | 1:4 |
|  | Mass ratio of starch (starch/thickener) | 20 | 2 | 1 | 0.4 | 2 | 5 | 7 | 4 |
|  | Mass ratio of anionic surfactant (C/B) | 1 | 1 | 1 | 1 | 1 | 1 | 1 | 0.1 |

TABLE 15-continued

| Evaluation | | | | | | | | |
|---|---|---|---|---|---|---|---|---|
| Rate of onset of thickening effect | 3 | 5 | 5 | 3 | 4 | 5 | 5 | 3 |
| Viscosity stability | 3 | 5 | 4 | 3 | 5 | 5 | 5 | 3 |

| | | Example 6-18 | Example 6-19 | Example 6-20 | Example 6-21 | Example 6-22 | Example 6-23 | Example 6-24 |
|---|---|---|---|---|---|---|---|---|
| | First agent (powdery) | | | | | | | |
| | Potassium persulfate | 20 | 20 | 20 | 20 | 20 | 20 | 20 |
| | Sodium persulfate | 15 | 15 | 15 | 15 | 15 | 15 | 15 |
| | Ammonium persulfate | 10 | 10 | 10 | 10 | 10 | 10 | 10 |
| | Sodium metasilicate | 10 | 10 | 10 | 10 | 10 | 10 | 10 |
| | Disodium edetate | 3 | 3 | 3 | 3 | 3 | 3 | 3 |
| | Magnesium stearate | 1 | 1 | 1 | 1 | 1 | 1 | 1 |
| (C) | Sodium lauryl sulfate | 0.5 | 5 | 10 | 8 | 4 | 2 | 0.5 |
| (E) | Carboxymethylcellulose | 5 | 5 | 5 | 5 | 5 | 5 | 5 |
| (D) | Potato starch | 20 | 20 | 20 | 20 | 20 | 20 | 20 |
| | Sodium sulfate | Remainder | Remainder | Remainder | Remainder | Remainder | Remainder | Remainder |
| | Total | 100 | 100 | 100 | 100 | 100 | 100 | 100 |
| | Second agent (emulsion) | | | | | | | |
| | 35% hydrogen peroxide | 17 | 17 | 17 | 17 | 17 | 17 | 17 |
| | Cetanol | 0.5 | 0.5 | 0.5 | 0.5 | 0.5 | 0.5 | 0.5 |
| | POE(5) lauryl ether | 0.5 | 0.5 | 0.5 | 0.5 | 0.5 | 0.5 | 0.5 |
| (B) | Stearyl trimethyl ammonium chloride | 0.25 | 0.25 | 0.25 | 2 | 1 | 0.5 | 0.125 |
| | Purified water | Remainder | Remainder | Remainder | Remainder | Remainder | Remainder | Remainder |
| | Total | 100 | 100 | 100 | 100 | 100 | 100 | 100 |
| | First agent:second agent mixing ratio (mass ratio) | 1:4 | 1:4 | 1:4 | 1:4 | 1:4 | 1:4 | 1:4 |
| | Mass ratio of starch (starch/thickener) | 4 | 4 | 4 | 4 | 4 | 4 | 4 |
| | Mass ratio of anionic surfactant (C/B) | 0.5 | 5 | 10 | 1 | 1 | 1 | 1 |
| | Evaluation | | | | | | | |
| | Rate of onset of thickening effect | 4 | 5 | 5 | 5 | 5 | 5 | 4 |
| | Viscosity stability | 4 | 5 | 4 | 4 | 5 | 5 | 4 |

As shown in Tables 14 and 15, the hair bleaches of Examples that were constituted by formulating an anionic surfactant, a thickener, and starch in the first agent and formulating a cationic surfactant in the second agent produced favorable results for both the items of the "rate of onset of thickening effect" and "viscosity stability".

As shown in Table 14, it was demonstrated that Reference Example 6-1 containing a nonionic surfactant instead of an anionic surfactant in the first agent and Reference Example 6-2 containing a nonionic surfactant instead of a cationic surfactant in the second agent were less regarded than Examples in the item "rate of onset of thickening effect". Reference Examples 6-1 and 6-2 produced evaluation results inferior to those of Examples in the item "viscosity stability", because the viscosity continued to gradually rise over time.

Reference Example 6-3 containing no thickener in the first agent produced evaluation results inferior to those of Examples in the item "rate of onset of thickening effect", because the final viscosity of the mixture was low. Reference Example 6-4 containing no starch in the first agent produced evaluation results inferior to those of Examples in the item "rate of onset of thickening effect", because the final viscosity of the mixture was low. However, Reference Example 6-4 produced evaluation results inferior to those of Examples in the item "viscosity stability", because the viscosity continued to gradually decrease over time.

Test 6-2

Hair bleaches of Example 6-25 and Reference Examples 6-5 to 6-7 comprising a powdery first agent and an emulsion second agent containing components shown in Table 16 were prepared. In Table 16, units for the numeric values representing the content of each component in the hair bleaches are % by mass. Then, the first and second agents were added at a mass ratio of 1:4 to the same sealable container as the container 20 shown in FIGS. 1(a) to 2. This container was tightly closed and shaken approximately 20 to 30 times to obtain a foamy hair bleach. The obtained hair bleach was evaluated for the rate of onset of a thickening effect and viscosity stability by the methods shown below.

<Measurement and Evaluation of Rate of Onset of Thickening Effect>

The obtained foamy hair bleach was evaluated for viscosity by five expert panelists based on the degree of dripping after lifting of the foam by hand three minutes after the mixing of the first and second agents. In the "Rate of onset of thickening effect" columns of Table 16, the score "5" indicates that the onset of a thickening effect is excellent without dripping three minutes after the mixing of the first and second agents; the score "4" indicates that the onset of a thickening effect is good with little dripping; the score "3" indicates that the onset of a thickening effect is favorable with not much dripping; the score "2" indicates that the onset of a thickening effect is slightly poor with dripping; and the score "1" indicates that the onset of a thickening effect is poor with much dripping.
<Viscosity Stability>

The difference in the degree of dripping between the lifting of the foam by hand five minutes after the mixing of the first and second agents and that of 25 minutes after the mixing of the first and second agents was evaluated by five expert panelists.

In the "Viscosity stability" column of Table 15, the score "5" indicates that the viscosity stability is excellent without difference in dripping between 5 minutes and 25 minutes after the mixing of the first and second agents; the score "4" indicates that the viscosity stability is good with little difference in dripping; the score "3" indicates that the viscosity stability is favorable with not much difference in dripping; the score "2" indicates that the viscosity stability is slightly poor with difference in dripping; and the score "1" indicates that the viscosity stability is poor with distinct difference in dripping.

Examples in the item "rate of onset of thickening effect", because the final viscosity of the mixture was also low.

Reference Example 6-7 containing no starch in the first agent produced evaluation results inferior to those of Examples in the item "viscosity stability", because the viscosity continued to gradually decrease over time and the liquid increasingly dripped.

Test 7

Hair dyes of Examples 7-1 to 7-13 and Reference Examples 7-1 to 7-5 comprising a powdery first agent containing components shown in Table 17 and a liquid second agent containing components shown in Tables 18 to 20 were prepared. In Tables 17 to 20, units for the numeric values representing the content of each component in the hair dyes are by mass. In this test, MERQUAT 550 (manufactured by Ondeo Nalco) was used as a dimethyl diallyl ammonium

TABLE 16

|  | Example 6-25 | Reference Example 6-5 | Reference Example 6-6 | Reference Example 6-7 |
|---|---|---|---|---|
| First agent (powdery) | | | | |
| Ammonium sulfate | 15 | 15 | 15 | 15 |
| Sodium carbonate | 30 | 30 | 30 | 30 |
| Disodium edetate | 3 | 3 | 3 | 3 |
| Magnesium stearate | 1 | 1 | 1 | 1 |
| (C) Sodium lauryl sulfate | 4 | 4 | 4 | 4 |
| (E) Carboxymethylcellulose | 10 | 10 | 10 | |
| (D) Potato starch | 20 | 20 | | 20 |
| Sodium sulfate | Remainder | Remainder | Remainder | Remainder |
| Total | 100 | 100 | 100 | 100 |
| Second agent (emulsion) | | | | |
| 35% hydrogen peroxide | 15 | 15 | 15 | 15 |
| Coconut oil fatty acid amidopropyl betaine solution (30%) | 10 | 10 | 10 | 10 |
| POE(5) lauryl ether | 0.5 | 0.5 | 0.5 | 0.5 |
| (B) Stearyl trimethyl ammonium chloride | 1 | | 1 | 1 |
| (b) Sodium lauryl sulfate | | 1 | | |
| Purified water | Remainder | Remainder | Remainder | Remainder |
| Total | 100 | 100 | 100 | 100 |
| First agent:second agent mixing ratio (mass ratio) | 1:4 | 1:4 | 1:4 | 1:4 |
| Mass ratio of starch (starch/thickener) | 2 | 2 | — | — |
| Mass ratio of anionic surfactant (C/B) | 1 | — | — | 1 |
| Evaluation | | | | |
| Rate of onset of thickening effect | 5 | 1 | 1 | 3 |
| Viscosity stability | 5 | 1 | 2 | 1 |

As shown in Table 15, the hair bleach of Example 6-25 that was constituted by formulating an anionic surfactant, a thickener, and starch in the first agent and formulating a cationic surfactant in the second agent produced favorable results for both the items of "rate of onset of thickening effect" and "viscosity stability". This demonstrated that the hair bleach that is in a foamy form in use is also good in the "rate of onset of thickening effect" and "viscosity stability".

As shown in Table 16, it was demonstrated that Reference Example 6-5 containing an anionic surfactant instead of a cationic surfactant in the second agent was less regarded than Examples in the evaluation of the item "rate of onset of thickening effect". Reference Example 6-5 produced evaluation results inferior to those of Examples in the item "viscosity stability", because the foam was hardened over time.

Reference Example 6-6 containing no thickener in the first agent produced evaluation results inferior to those of chloride-acrylamide copolymer; MERQUAT 295 (manufactured by Ondeo Nalco) was used as a dimethyl diallyl ammonium chloride-acrylic acid copolymer; and MERQUAT 100 (manufactured by Ondeo Nalco) was used as polydimethylmethylenepiperidinium chloride. In Tables 17 to 20, the numeric values representing the content of each component indicate the purity content of the component.

TABLE 17

| First agent (powdery) | |
|---|---|
| Ammonium sulfate | 15 |
| Sodium carbonate | 30 |
| Disodium edetate | 3 |
| Magnesium stearate | 1 |
| Toluene-2,5-diamine sulfate | 3 |
| Sodium lauryl sulfate | 5 |

TABLE 17-continued

| First agent (powdery) | |
| --- | --- |
| Carboxymethylcellulose | 15 |
| Sodium sulfate | Remainder |
| Total | 100 |

The first and second agents in the hair dye of each of Examples and Reference Examples were stored at 45° C. for 30 days and used in the subsequent tests. The first and second agents were added to the same sealable container as the container 20 shown in FIGS. 1(*a*) to 2. This container was tightly closed and shaken approximately 20 to 30 times for shaking the mixture of the first and second agents in the container to obtain a foamy hair dye. The obtained foamy hair dye was taken in gloved hand, applied to a bundle of human black hair, and then left at room temperature (25° C.) for 30 minutes. Then, the hair dye attached to the hair bundle was washed off with water, and the hair bundle was shampooed two times and treated with a hair conditioner once. Subsequently, the hair bundle was dried in hot air and then left for 1 day to obtain a dyed hair bundle. The hair dyes of Examples and Reference Examples were evaluated for foamability and the texture of the hair bundle during the wash off of the hair dye according to the methods shown below. The results are shown in Tables 18 to 20.

<Foamability>

The state of the hair dye after foaming was visually observed by expert panelists. In the "Foamability" column of Tables 18 to 20, the score "5" indicates that the foaming is excellent; the score "4" indicates that the foaming is good; the score "3" indicates that the foaming is favorable; the score "2" indicates that the foaming is slightly insufficient; and the score "1" indicates that the foaming is insufficient or too much foaming results in low viscous, light, and large bubbles.

<Hair Texture (Finger Combability)>

The texture of the hair bundle (hair) during the wash off of the hair dye was evaluated by observation by expert panelists with the touch of hand on the hair bundle. In the "Hair texture (finger combability)" columns of Tables 18 to 20, the score "5" indicates that the finger combability is excellent; the score "4" indicates that the finger combability is good; the score "3" indicates that the finger combability is favorable; the score "2" indicates that the finger combability is poor with perceivable squeakiness; and the score "1" indicates that the finger combability is very poor and the finger becomes stuck in the hair during finger combing.

TABLE 18

| | Components | Second agent (liquid) | Example 7-1 | Example 7-2 | Example 7-3 | Example 7-4 | Example 7-5 | Example 7-6 |
| --- | --- | --- | --- | --- | --- | --- | --- | --- |
| | (G) | 35% hydrogen peroxide | 15 | 15 | 15 | 15 | 15 | 15 |
| | (A) | Coconut oil fatty acid amidopropyl betaine | 2.4 | 2.4 | 2.4 | 2.4 | | |
| | (A) | Lauryldimethylaminoacetic acid betaine | | | | | 2.4 | |
| | (A) | Amidopropyl betaine laurate | | | | | | 2.4 |
| | | POE(5) lauryl ether | 0.5 | 0.5 | 0.5 | 0.5 | 0.5 | 0.5 |
| | | Stearyl trimethyl ammonium chloride | 1 | 1 | 1 | 1 | 1 | 1 |
| | | Sodium lauryl sulfate | | | | | | |
| | (H) | Dimethyl diallyl ammonium chloride-acrylamide copolymer | 1 | | | | 1 | 1 |
| | (H) | Dimethyl diallyl ammonium chloride-acrylic acid copolymer | | 1 | | | | |
| | (H) | Polydimethylmethylenepiperidinium chloride | | | 1 | | | |
| | (H) | Hydroxyethylcellulose dimethyl diallyl ammonium | | | | 1 | | |
| | | Purified water | Remainder | Remainder | Remainder | Remainder | Remainder | Remainder |
| | | Total | 100 | 100 | 100 | 100 | 100 | 100 |
| | | First agent:second agent mixing ratio (mass ratio) | 1:5 | 1:5 | 1:5 | 1:5 | 1:5 | 1:5 |
| | | Content of component A in use | 2.0 | 2.0 | 2.0 | 2.0 | 2.0 | 2.0 |
| Evaluation | | Hair texture (finger combability) | 5 | 5 | 5 | 4 | 5 | 5 |
| | | Foamability | 5 | 5 | 5 | 5 | 5 | 5 |

TABLE 19

| Components | Second agent (liquid) | Example 7-7 | Example 7-8 | Example 7-9 | Example 7-10 | Example 7-11 | Example 7-12 | Example 7-13 |
| --- | --- | --- | --- | --- | --- | --- | --- | --- |
| (G) | 35% hydrogen peroxide | 15 | 15 | 15 | 15 | 15 | 15 | 15 |
| (A) | Coconut oil fatty acid amidopropyl betaine | 0.6 | 1.8 | 3 | 4 | 5 | 6 | 10 |
| (A) | Lauryldimethylaminoacetic acid betaine | | | | | | | |
| (A) | Amidopropyl betaine laurate | | | | | | | |
| | POE(5) lauryl ether | 0.5 | 0.5 | 0.5 | 0.5 | 0.5 | 0.5 | 0.5 |
| | Stearyl trimethyl ammonium chloride | 1 | 1 | 1 | 1 | 1 | 1 | 1 |
| | Sodium lauryl sulfate | | | | | | | |
| (H) | Dimethyl diallyl ammonium chloride-acrylamide copolymer | 1 | 1 | 1 | 1 | 1 | 1 | 1 |

TABLE 19-continued

| Components | Second agent (liquid) | Example 7-7 | Example 7-8 | Example 7-9 | Example 7-10 | Example 7-11 | Example 7-12 | Example 7-13 |
|---|---|---|---|---|---|---|---|---|
| (H) | Dimethyl diallyl ammonium chloride-acrylic acid copolymer | | | | | | | |
| (H) | Polydimethylmethylenepiperidinium chloride | | | | | | | |
| (H) | Hydroxyethylcellulose dimethyl diallyl ammonium | | | | | | | |
| | Purified water | Remainder | Remainder | Remainder | Remainder | Remainder | Remainder | Remainder |
| | Total | 100 | 100 | 100 | 100 | 100 | 100 | 100 |
| | First agent:second agent mixing ratio (mass ratio) | 1:5 | 1:5 | 1:5 | 1:5 | 1:5 | 1:5 | 1:5 |
| | Content of component A in use | 0.5 | 1.5 | 2.5 | 3.3 | 4.2 | 5.0 | 8.3 |
| Evaluation | Hair texture (finger combability) | 5 | 5 | 5 | 4 | 4 | 4 | 4 |
| | Foamability | 3 | 5 | 5 | 4 | 4 | 4 | 4 |

As shown in Tables 18 and 19, Examples each containing hydrogen peroxide, an amphoteric surfactant, and a cationic polymer in the second agent produced favorable evaluation results for both the item of "hair texture (finger combability)" and "foamability". Particularly, it was demonstrated that Examples 7-1 to 7-3 each containing, as a cationic polymer, a product that was prepared in a liquid state at 25° C. were more highly regarded in the evaluation of "hair texture (finger combability)" than Example 7-4 containing a cationic polymer that was in a solid state at 25° C. Moreover, Examples 7-8 and 7-9 in which the content of the amphoteric surfactant in the second agent fell within the range of 1.5 to 3.5% by mass were highly regarded in both the evaluations for "hair texture (finger combability)" and "foamability".

Test 8

(Preparation of Hydrogen Peroxide-Containing Composition)

Hydrogen peroxide-containing compositions of Reference Examples 8-1-1 to 8-1-19 and 8-2-1 to 8-2-5 were prepared by formulating components described in Tables 21 and 22. The prepared hydrogen peroxide-containing compositions were evaluated for the stability of hydrogen peroxide and odor according to the methods shown below. In Tables 21 and 22, units for the numeric values representing the content of each component in the hydrogen peroxide-containing compositions are % by mass.

TABLE 20

| Components | Second agent (liquid) | Reference Example 7-1 | Reference Example 7-2 | Reference Example 7-3 | Reference Example 7-4 | Reference Example 7-5 |
|---|---|---|---|---|---|---|
| (G) | 35% hydrogen peroxide | 15 | 15 | 15 | 15 | 15 |
| (A) | Coconut oil fatty acid amidopropyl betaine | | | | | 2.4 |
| (A) | Lauryldimethylaminoacetic acid betaine | | | | | |
| (A) | Amidopropyl betaine laurate | | | | | |
| | POE(5) lauryl ether | 2.9 | 0.5 | 2.9 | 0.5 | 0.5 |
| | Stearyl trimethyl ammonium chloride | 1 | 6 | | | 1 |
| | Sodium lauryl sulfate | | | 1 | 6 | |
| (H) | Dimethyl diallyl ammonium chloride-acrylamide copolymer | 1 | 1 | 1 | 1 | |
| (H) | Dimethyl diallyl ammonium chloride-acrylic acid copolymer | | | | | |
| (H) | Polydimethylmethylenepiperidinium chloride | | | | | |
| (H) | Hydroxyethylcellulose dimethyl diallyl ammonium | | | | | |
| | Purified water | Remainder | Remainder | Remainder | Remainder | Remainder |
| | Total | 100 | 100 | 100 | 100 | 100 |
| | First agent:second agent mixing ration (mass ratio) | 1:5 | 1:5 | 1:5 | 1:5 | 1:5 |
| | Content of component A in use | — | — | — | — | 2.0 |
| Evaluation | Hair texture (finger combability) | 3 | 3 | 3 | 2 | 1 |
| | Foamability | 1 | 1 | 1 | 3 | 5 |

As shown in Table 20, it was demonstrated that Reference Examples 7-1 to 7-4 that contained no amphoteric surfactant in the second agent and had the increased content of a non-ionic surfactant, a cationic surfactant, or an anionic surfactant in the second agent were less regarded than Examples in both the evaluations of "hair texture (finger combability)" and "foamability". Moreover, it was demonstrated that Reference Example 7-5 containing no cationic polymer in the second agent was highly regarded in the evaluation of "foamability", but was less regarded in the evaluation of "hair texture (finger combability)".

(Stability of Hydrogen Peroxide)

Each prepared hydrogen peroxide containing composition was stored for 1 month in a thermostat bath of 45° C. Then, the amount of residual hydrogen peroxide was determined by the redox titration method, and the residual rate of hydrogen peroxide was calculated. Evaluation criteria were as follows. The evaluation results are shown in Tables 21 and 22.

5: 99% or more residual rate of hydrogen peroxide.
4: 98% or more and less than 99% residual rate of hydrogen peroxide.
3: 97% or more and less than 98% residual rate of hydrogen peroxide.
2: 96% or more and less than 97% residual rate of hydrogen peroxide.
1: Less than 96% residual rate of hydrogen peroxide.
(Regarding Odor)

Each prepared hydrogen peroxide-containing composition was evaluated for odor. Evaluation criteria were as follows. The evaluation results are shown in Tables 21 and 22.

3: There is no odor derived from the raw material phenoxyethanol.
2: There is little odor derived from the raw material phenoxyethanol.
1: There is noticeable odor derived from the raw material phenoxyethanol.

TABLE 21

| | | Reference Example 8-1-1 | Reference Example 8-1-2 | Reference Example 8-1-3 | Reference Example 8-1-4 | Reference Example 8-1-5 | Reference Example 8-1-6 | Reference Example 8-1-7 |
|---|---|---|---|---|---|---|---|---|
| | Hydrogen peroxide-containing composition | | | | | | | |
| (G) | 35% hydrogen peroxide | 15 | 15 | 15 | 15 | 15 | 15 | 15 |
| | Celanol | 0.5 | 0.5 | 0.5 | 0.5 | 0.5 | 0.5 | 0.5 |
| | POE(5) lauryl ether (nonionic surfactant) | 0.5 | 0.5 | 0.5 | 0.5 | 0.5 | 0.5 | 0.5 |
| (B) | Stearyl trimethyl ammonium chloride | — | — | — | — | 1 | — | — |
| (A) | Coconut oil fatty acid amidopropyl betaine | 1 | 1 | 1 | 1 | — | — | — |
| (A) | Lauryldimethylaminoacetic acid betaine | — | — | — | — | — | 1 | — |
| (A) | Amidopropyl betaine laurate | — | — | — | — | — | — | 1 |
| | Dipropylene glycol | 1 | 1 | 1 | 1 | 1 | 1 | 1 |
| (J) | Phenoxyethanol | 0.2 | 0.2 | 0.2 | 0.2 | 0.2 | 0.2 | 0.2 |
| | Ethanol | — | — | — | — | — | — | — |
| (K) | Benzoic acid | — | 0.2 | — | — | — | — | — |
| (K) | Sodium benzoate | 0.2 | — | 0.2 | 0.2 | 0.2 | 0.2 | 0.2 |
| | p-oxybenzoic acid ester | — | — | — | — | — | — | — |
| | Salicylic acid | — | — | — | — | — | — | — |
| | Edetic acid | — | — | 0.1 | — | — | — | — |
| | Tetrasodium edetate | — | — | 0.1 | — | — | — | — |
| | Hydroxyethanediphosphonic acid | 0.1 | 0.1 | — | — | 0.1 | 0.1 | 0.1 |
| | Tetrasodium hydroxyethanediphosphonate | 0.1 | 0.1 | — | — | 0.1 | 0.1 | 0.1 |
| | Citric acid | | | Formulated to adjust pH to 4 | | | | |
| | Purified water | Remainder | Remainder | Remainder | Remainder | Remainder | Remainder | Remainder |
| | Total | 100 | 100 | 100 | 100 | 100 | 100 | 100 |
| | J/K | 1 | 1 | 1 | 1 | 1 | 1 | 1 |
| | Evaluation | | | | | | | |
| | Stability of hydrogen peroxide | 5 | 5 | 5 | 4 | 5 | 5 | 5 |
| | Odor | 3 | 3 | 3 | 3 | 3 | 3 | 3 |

| | | Reference Example 8-1-8 | Reference Example 8-2-1 | Reference Example 8-2-2 | Reference Example 8-2-3 | Reference Example 8-2-4 | Reference Example 8-2-5 |
|---|---|---|---|---|---|---|---|
| | Hydrogen peroxide-containing composition | | | | | | |
| (G) | 35% hydrogen peroxide | 15 | 15 | 15 | 15 | 15 | 15 |
| | Celanol | 0.5 | 0.5 | 0.5 | 0.5 | 0.5 | 0.5 |
| | POE(5) lauryl ether (nonionic surfactant) | — | 0.5 | 0.5 | 0.5 | — | — |
| (B) | Stearyl trimethyl ammonium chloride | — | — | — | 1 | — | — |
| (A) | Coconut oil fatty acid amidopropyl betaine | 1 | 1 | 1 | — | 1 | 1 |
| (A) | Lauryldimethylaminoacetic acid betaine | — | — | — | — | — | — |
| (A) | Amidopropyl betaine laurate | — | — | — | — | — | — |
| | Dipropylene glycol | 1 | 1 | 1 | 1 | 1 | 1 |
| (J) | Phenoxyethanol | 0.2 | — | 0.2 | — | — | 0.2 |
| | Ethanol | — | 0.2 | — | 0.2 | 0.2 | — |
| (K) | Benzoic acid | — | — | — | — | — | — |
| (K) | Sodium benzoate | 0.2 | 0.2 | — | 0.2 | 0.2 | — |
| | p-oxybenzoic acid ester | — | — | 0.2 | — | — | 0.2 |
| | Salicylic acid | — | — | — | — | — | — |
| | Edetic acid | — | — | — | — | — | — |

TABLE 21-continued

|  | | | | | | |
|---|---|---|---|---|---|---|
| Tetrasodium edetate | — | — | — | — | — | — |
| Hydroxyethanediphosphonic acid | 0.1 | 0.1 | 0.1 | 0.1 | 0.1 | 0.1 |
| Tetrasodium hydroxyethanediphosphonate | 0.1 | 0.1 | 0.1 | 0.1 | 0.1 | 0.1 |
| Citric acid | Formulated to adjust pH to 4 | | | | | |
| Purified water | Remainder | Remainder | Remainder | Remainder | Remainder | Remainder |
| Total | 100 | 100 | 100 | 100 | 100 | 100 |
| J/K | 1 | — | — | — | — | — |
| Evaluation | | | | | | |
| Stability of hydrogen peroxide | 5 | 1 | 1 | 2 | 1 | 1 |
| Odor | 3 | 3 | 3 | 3 | 3 | 3 |

TABLE 22

|  | | Reference Example 8-1-9 | Reference Example 8-1-10 | Reference Example 8-1-11 | Reference Example 8-1-12 | Reference Example 8-1-13 | Reference Example 8-1-14 |
|---|---|---|---|---|---|---|---|
| | Hydrogen peroxide-containing composition | | | | | | |
| (G) | 35% hydrogen peroxide | 15 | 15 | 15 | 15 | 15 | 15 |
| | Cetanol | 0.5 | 0.5 | 0.5 | 0.5 | 0.5 | 0.5 |
| | POE(5) lauryl ether (nonionic surfactant) | 0.5 | 0.5 | 0.5 | 0.5 | 0.5 | 0.5 |
| (A) | Coconut oil fatty acid amidopropyl betaine solution | 1 | 1 | 1 | 1 | 1 | 1 |
| | Dipropylene glycol | 1 | 1 | 1 | 1 | 1 | 1 |
| (J) | Phenoxyethanol | 0.2 | 0.2 | 0.2 | 0.2 | 0.05 | 0.1 |
| (K) | Sodium benzoate | 0.01 | 0.1 | 0.6 | 1 | 0.4 | 0.4 |
| | Hydroxyethanediphosphonic acid | 0.1 | 0.1 | 0.1 | 0.1 | 0.1 | 0.1 |
| | Tetrasodium hydroxyethanediphosphonate | 0.1 | 0.1 | 0.1 | 0.1 | 0.1 | 0.1 |
| | Citric acid | Formulated to adjust pH to 4 | | | | | |
| | Purified water | Remainder | Remainder | Remainder | Remainder | Remainder | Remainder |
| | Total | 100 | 100 | 100 | 100 | 100 | 100 |
| | J/K | 20 | 2 | 0.33 | 0.2 | 0.13 | 0.25 |
| | Evaluation | | | | | | |
| | Stability of hydrogen peroxide | 3 | 4 | 5 | 5 | 3 | 4 |
| | Odor | 3 | 3 | 3 | 3 | 3 | 3 |

|  | | Reference Example 8-1-15 | Reference Example 8-1-16 | Reference Example 8-1-17 | Reference Example 8-1-18 | Reference Example 8-1-19 |
|---|---|---|---|---|---|---|
| | Hydrogen peroxide-containing composition | | | | | |
| (G) | 35% hydrogen peroxide | 15 | 15 | 15 | 15 | 15 |
| | Cetanol | 0.5 | 0.5 | 0.5 | 0.5 | 0.5 |
| | POE(5) lauryl ether (nonionic surfactant) | 0.5 | 0.5 | 0.5 | 0.5 | 0.5 |
| (A) | Coconut oil fatty acid amidopropyl betaine solution | 1 | 1 | 1 | 1 | 1 |
| | Dipropylene glycol | 1 | 1 | 1 | 1 | 1 |
| (J) | Phenoxyethanol | 0.15 | 0.2 | 0.4 | 0.8 | 1 |
| (K) | Sodium benzoate | 0.4 | 0.4 | 0.4 | 0.4 | 0.4 |
| | Hydroxyethanediphosphonic acid | 0.1 | 0.1 | 0.1 | 0.1 | 0.1 |
| | Tetrasodium hydroxyethanediphosphonate | 0.1 | 0.1 | 0.1 | 0.1 | 0.1 |
| | Citric acid | Formulated to adjust pH to 4 | | | | |
| | Purified water | Remainder | Remainder | Remainder | Remainder | Remainder |
| | Total | 100 | 101 | 100 | 100 | 100 |
| | J/K | 0.375 | 0.5 | 1 | 2 | 2.5 |
| | Evaluation | | | | | |
| | Stability of hydrogen peroxide | 5 | 5 | 5 | 5 | 5 |
| | Odor | 3 | 3 | 3 | 3 | 2 | shown in Table 21, the hydrogen peroxide-containing compositions of Reference Examples 8-2-1 to 8-2-5 did not contain at least one of phenoxyethanol and benzoic acid (benzoate) in the surfactant-containing system. It was demonstrated that Reference Examples 8-2-1 to 8-2-5 had the poor stability of hydrogen peroxide during storage as seen from the "Stability of hydrogen peroxide" column. Of them, the hydrogen peroxide-containing compositions of Reference Examples 8-2-1, 8-2-2, 8-2-4, and 8-2-5 contained an amphoteric surfactant as a surfactant. These particularly had poor stability of hydrogen peroxide during storage.

By contrast, the hydrogen peroxide-containing compositions of Reference Examples 8-1-1 to 8-1-19 contained both phenoxyethanol and benzoic acid (benzoate) in the surfactant-containing system and was observed to be good in stability for hydrogen peroxide during storage. From the comparison of Reference Examples 8-1-1 and 8-1-2 with Reference Examples 8-2-1 and 8-2-2, it was demonstrated that the stability of hydrogen peroxide was improved in Reference Examples 8-1-1 and 8-1-2. From the comparison of Reference Example 8-1-5 with Reference Example 8-2-4, it was demonstrated that the stability of hydrogen peroxide was improved in Reference Example 8-1-5. From the comparison of Reference Example 8-1-8 with Reference Examples 8-2-4 and 9-2-5, it was demonstrated that the stability of hydrogen peroxide was improved in Reference Example 8-1-8. From the comparison among the compositions containing an amphoteric surfactant as a surfactant (e.g., Reference Examples 8-1-1, 8-2-1, and 8-2-2), it was demonstrated that the effect of improving the stability of hydrogen peroxide is particularly high in the compositions containing the amphoteric surfactant.

From the comparison among Reference Examples 8-1-1 to 8-1-19, the followings were demonstrated from the comparison of Reference Examples 8-1-9 and 8-1-13 with the other Reference Examples, it was demonstrated that the stability of hydrogen peroxide was further improved when the mass ratio (J/K ratio) of the component J to the component K fell within the range of 0.2 to 2.5. From the comparison of Reference Examples 8-1-9 and 8-1-10 with the other Reference Examples, it was demonstrated that the stability of hydrogen peroxide was further improved when the amount of the component K was 0.1% by mass or more; and the stability of hydrogen peroxide was particularly improved when the amount of the component K was 0.15% by mass or more. From the comparison of Reference Examples 8-1-13 and 8-1-14 with the other Reference Examples, it was demonstrated that the stability of hydrogen peroxide was further improved when the amount of the component J was 0.1% by mass or more; and the stability of hydrogen peroxide was particularly improved when the amount of the component J was 0.15% by mass or more. From the comparison of Reference Example 8-1-19 with the other Reference Examples, it was demonstrated that the stability of hydrogen peroxide was achieved with phenoxyethanol odor suppressed when the amount of the component J formulated fell within the range of 0.15 to 0.8% by mass.

Test 9

(Preparation of Composition for Dyeing Hair)

First and second agents of compositions for dyeing hair of Examples 9-1 to 9-5 and 9-7 to 9-14 Reference Examples 9-1 to 9-4 and 9-6 were prepared by formulating components described in Tables 23 and 24. Subsequently, the obtained first and second agents were mixed at the mixing ratio (mass ratio) described in Tables 23 and 24 to prepare a composition for dyeing hair. For those whose final form is described as "Foam" in Tables 23 and 24, the first and second agents were placed in a sealed container, which was then shaken to obtain a foamy composition for dyeing hair. On the other hand, for those whose final form is described as "Cream" in these tables, the first and second agents were placed in an open container and gently mixed without foaming in the container. In Tables 23 and 24, units for the numeric values representing the content of each component in the compositions for dyeing hair are % by mass.

(Dyeing Treatment)

Each prepared composition for dyeing hair was applied to a hair bundle of black human hair by hand using thin-gloves (made of resin). Then, the hair bundle was left for 30 minutes in a thermostat bath (30° C.). Subsequently, the hair bundle was washed with tap water and then shampooed once and treated with a conditioner once. Subsequently, the hair bundle was dried. Then, the hair bundle was left at room temperature for 1 day. In this way, the dyeing treatment of the hair bundle was performed.

(Regarding Hair Texture (Smoothness) after Finish)

The hair texture during the finger combing of the thus-dyed hair bundle was compared with that of an undyed hair bundle. The hair texture of the dyed hair bundle was evaluated from the viewpoint of whether or not smoothness during finger combing was favorably obtained without the roughness of the hair bundle. Evaluation criteria were as follows. The evaluation results are shown in Tables 23 and 24.

5: The smoothness was very favorably obtained.
4: The smoothness was favorably obtained.
3: The smoothness was relatively favorably obtained.
2: The smoothness was slightly poorly obtained.
1: The smoothness was very poorly obtained.

(Regarding Hair Texture (Squeakiness, Tangleability, and Bristliness) after Finish)

The hair texture during the finger combing of the thus-dyed hair bundle was compared with that of an undyed hair bundle. The hair texture of the dyed hair bundle was evaluated from the viewpoint of whether or not finger combing was difficult to perform due to the squeakiness, tangleability, and bristliness of the hair bundle. Evaluation criteria were as follows. The evaluation results are shown in Tables 23 and 24.

5: The finger combability was very favorable.
4: The finger combability was favorable.
3: The finger combability was relatively favorable,
2: The finger combability was slightly poor.
1: The finger combability was very poor.

(Regarding Lightness after Finish)

The thus-dyed hair bundle was visually observed and evaluated for lightness after finish. Evaluation criteria were as follows. The evaluation results are shown in Tables 23 and 24.

5: The lightness was very favorable.
4: The lightness was favorable.
3: The lightness was relatively favorable.
2: The lightness was slightly poor.
1: The lightness was very poor.

TABLE 23

|  |  | Example 9-1 | Example 9-2 | Example 9-3 | Example 9-4 | Example 9-5 | Example 9-6 | Reference Example 9-1 | Reference Example 9-2 | Reference Example 9-3 | Reference Example 9-4 |
|---|---|---|---|---|---|---|---|---|---|---|---|
|  | First agent (powdery) |  |  |  |  |  |  |  |  |  |  |
|  | Ammonium sulfate | 15 | 15 | 15 | 15 | 15 | 15 | 15 | 15 | 15 | 15 |
| (f-1) | Sodium carbonate | 27 | 27 | 27 | — | 27 | 27 | 27 | 27 | — | — |
|  | Sodium bicarbonate | — | — | — | 27 | — | — | — | — | — | — |
| (L) | Disodium edetate | 9 | — | — | 9 | 9 | 9 | 5 | — | 9 | — |
|  | Diethylenetriaminepentaacetic acid | — | 9 | — | — | — | — | — | — | — | — |
|  | Trisodium ethylenediaminehydroxyethyltriacetate | — | — | 9 | — | — | — | — | — | — | — |
|  | Sodium metasilicate | — | — | — | — | — | — | — | — | 27 | 27 |
|  | Magnesium stearate | 1 | 1 | 1 | 1 | 1 | 1 | 1 | 1 | 1 | 1 |
|  | Toluene-2,5-diamine sulfate | 3 | 3 | 3 | 3 | 3 | 3 | 3 | 3 | 3 | 3 |
|  | Sodium lauryl sulfate | 5 | 5 | 5 | 5 | 5 | 5 | 5 | 5 | 5 | 5 |
|  | Carboxymethylcellulose | 10 | 10 | 10 | 10 | 10 | 10 | 10 | 10 | 10 | 10 |
|  | Sodium sulfate | Remainder | Remainder | Remainder | Remainder | Remainder | Remainder | Remainder | Remainder | Remainder | Remainder |
|  | Total | 100 | 100 | 100 | 100 | 100 | 100 | 100 | 100 | 100 | 100 |
|  | Second agent (emulsion) |  |  |  |  |  |  |  |  |  |  |
| (G) | 35% hydrogen peroxide | 15 | 15 | 15 | 15 | 15 | 15 | 15 | 15 | 15 | 15 |
|  | Coconut oil fatty acid amidopropyl betaine solution (30%) | 5 | 5 | 5 | 5 | 5 | 5 | 5 | 5 | 5 | 5 |
|  | POE(5) lauryl ether | 0.5 | 0.5 | 0.5 | 0.5 | 0.5 | 0.5 | 0.5 | 0.5 | 0.5 | 0.5 |
|  | Stearyl trimethyl ammonium chloride | 1 | 1 | 1 | 1 | 1 | 1 | 1 | 1 | 1 | 1 |
| (H) | Dimethyl diallyl ammonium chloride-acrylamide copolymer solution | 0.02 | 0.02 | 0.02 | 0.02 | — | 0.02 | 0.02 | 0.02 | 0.02 | 0.02 |
|  | Polydimethylmethylenepiperidinium chloride solution | 0.6 | 0.6 | 0.6 | 0.6 | — | 0.6 | 0.6 | 0.6 | 0.6 | 0.6 |
|  | Purified water | Remainder | Remainder | Remainder | Remainder | Remainder | Remainder | Remainder | Remainder | Remainder | Remainder |
|  | Total | 100 | 100 | 100 | 100 | 100 | 100 | 100 | 100 | 100 | 100 |
|  | First agent:second agent mixing ratio (mass ratio) | 1:5 | 1:5 | 1:5 | 1:5 | 1:5 | 1:5 | 1:5 | 1:5 | 1:5 | 1:5 |
|  | Final form | Foam | Foam | Foam | Foam | Foam | Cream | Foam | Foam | Foam | Foam |
|  | Amount of component f-1 incorporated | 4.5 | 4.5 | 4.5 | 4.5 | 4.5 | 4.5 | 4.5 | 4.5 | 0 | 0 |
|  | Amount of component L incorporated | 1.5 | 1.5 | 1.5 | 1.5 | 1.5 | 1.5 | 0.8 | — | 1.5 | 1.5 |
|  | (f-1)/L formulation ratio (mass ratio) | 3 | 3 | 3 | 3 | 3 | 3 | 5.4 | — | 0 | 0 |
|  | Evaluation |  |  |  |  |  |  |  |  |  |  |
|  | Hair texture (smoothness) | 5 | 5 | 5 | 5 | 4 | 3 | 2 | 1 | 3 | 3 |
|  | Hair texture (squeakiness, tangleability, and bristliness) | 5 | 5 | 5 | 5 | 5 | 5 | 5 | 5 | 5 | 1 |
|  | Lightness | 5 | 5 | 5 | 4 | 5 | 5 | 4 | 4 | 5 | 5 |

TABLE 24

|  |  | Example 9-7 | Example 9-8 | Example 9-9 | Example 9-10 | Example 9-11 | Example 9-12 | Example 9-13 | Example 9-14 |
|---|---|---|---|---|---|---|---|---|---|
|  | First agent (powdery) |  |  |  |  |  |  |  |  |
|  | Ammonium sulfate | 15 | 15 | 15 | 15 | 15 | 15 | 15 | 15 |
| (f-1) | Sodium carbonate | 39 | 27 | 15 | 39 | 15 | 27 | 27 | 27 |
| (L) | Disodium edetate | 6 | 6 | 6 | 9 | 9 | 12 | 18 | 30 |
|  | Magnesium stearate | 1 | 1 | 1 | 1 | 1 | 1 | 1 | 1 |
|  | Toluene-2,5-diamine sulfate | 3 | 3 | 3 | 3 | 3 | 3 | 3 | 3 |
|  | Sodium lauryl sulfate | 5 | 5 | 5 | 5 | 5 | 5 | 5 | 5 |
|  | Carboxymethylcellulose | 10 | 10 | 10 | 10 | 10 | 10 | 10 | 10 |
|  | Sodium sulfate | Remainder | Remainder | Remainder | Remainder | Remainder | Remainder | Remainder | Remainder |
|  | Total | 100 | 100 | 100 | 100 | 100 | 100 | 100 | 100 |
|  | Second agent (emulsion) |  |  |  |  |  |  |  |  |
| (G) | 35% hydrogen peroxide | 15 | 15 | 15 | 15 | 15 | 15 | 15 | 15 |
|  | Coconut oil fatty acid amidopropyl betaine solution (30%) | 5 | 5 | 5 | 5 | 5 | 5 | 5 | 5 |
|  | POE(5) lauryl ether | 0.5 | 0.5 | 0.5 | 0.5 | 0.5 | 0.5 | 0.5 | 0.5 |
|  | Stearyl trimethyl ammonium chloride | 1 | 1 | 1 | 1 | 1 | 1 | 1 | 1 |

TABLE 24-continued

|   |   | Example 9-7 | Example 9-8 | Example 9-9 | Example 9-10 | Example 9-11 | Example 9-12 | Example 9-13 | Example 9-14 |
|---|---|---|---|---|---|---|---|---|---|
| (H) | Dimethyl diallyl ammonium chloride-acrylamide copolymer solution | 0.02 | 0.02 | 0.02 | 0.02 | 0.02 | 0.02 | 0.02 | 0.02 |
|  | Polydimethylmethylenepiperidinium chloride solution | 0.6 | 0.6 | 0.6 | 0.6 | 0.6 | 0.6 | 0.6 | 0.6 |
|  | Purified water | Remainder | Remainder | Remainder | Remainder | Remainder | Remainder | Remainder | Remainder |
|  | Total | 100 | 100 | 100 | 100 | 100 | 100 | 100 | 100 |
|  | First agent:second agent mixing ratio (mass ratio) | 1:5 | 1:5 | 1:5 | 1:5 | 1:5 | 1:5 | 1:5 | 1:5 |
|  | Final form | Foam | Foam | Foam | Foam | Foam | Foam | Foam | Foam |
|  | Amount of component f-1 incorporated | 6.5 | 4.5 | 2.5 | 6.5 | 2.5 | 4.5 | 4.5 | 4.5 |
|  | Amount of component L incorporated | 1.0 | 1.0 | 1.0 | 1.5 | 1.5 | 2.0 | 3.0 | 5.0 |
|  | (f-1)/L formulation ratio (mass ratio) | 6.5 | 4.5 | 2.5 | 4.3 | 1.7 | 2.3 | 1.5 | 0.9 |
|  | Evaluation |   |   |   |   |   |   |   |   |
|  | Hair texture (smoothness) | 3 | 4 | 5 | 5 | 5 | 5 | 5 | 5 |
|  | Hair texture (squeakiness, tangleability, and bristliness) | 5 | 5 | 5 | 5 | 5 | 5 | 5 | 5 |
|  | Lightness | 5 | 5 | 4 | 5 | 4 | 5 | 5 | 5 |

As seen from Tables 23 and 24, the composition for dyeing hair of Reference Example 9-1 offered slightly poor hair texture (smoothness) after finish, because the amount of the component L incorporated was less than 1% by mass. Moreover, the composition for dyeing hair of Reference Example 9-2 offered very poor hair texture (smoothness) after finish, because the component L was not incorporated therein.

By contrast, the compositions for dyeing hair of Examples were observed to offer favorable hair texture (smoothness) after finish and also favorable lightness after finish. When the composition for dyeing hair was compared among Examples, particular cationic polymer was not incorporated in Example 9-5. Therefore, it was slightly inferior in hair texture (smoothness) after finish to the other Examples. Moreover, the final form was a cream form in Reference Example 9-6. The final form was a foamy form in Examples, which was observed, to offer more favorable hair texture after finish than that of Reference Example 9-6.

Moreover, the mass ratio of the component f-1 to the component L exceeded 4.5 in Example 9-7. By contrast, this mass ratio fell within the range of 0.02 to 4.5 in Examples other than Example 9-7, which was observed to offer more favorable hair texture (smoothness) after finish than that of Example 9-7.

Reference Examples 9-3 and 9-4 used sodium metasilicate instead of the component f-1. Reference Example 9-3, compared with Reference Example 9-4, was not found to have the effect of improving smoothness after finish by suppressing roughness after finish, though this Example was found to have improvement in hair texture after finish by virtue of suppression of hair texture such as the stiff and squeaky hair bundle, tangled hair, and bristliness after finish.

The embodiments of the present invention have been described above in detail. However, the present invention is not limited to the embodiments by any means, and various changes or modifications may be made without departing from the spirit of the present invention.

Test 10-1

Hair dyes comprising a powdery first agent containing components shown in Table 25 and an emulsion second agent shown in Tables 26 and 27 were prepared. The second agent was prepared by first preparing an amphoteric surfactant-containing aqueous solution and next mixing the amphoteric surfactant-containing aqueous solution with other components, for example, hydrogen peroxide. In Tables 25 to 27, units for the numeric values representing the content of each component in the hair dyes are % by mass. Then, the first and second agents were mixed at a mass ratio of 1:5 and stirred using a stirring rod to prepare a foamy hair dye. The obtained hair dye was evaluated for foamability. Moreover, the obtained, second agent was evaluated for pH change and pH stability. The results are shown in Tables 26 and 27.

In Tables 26 and 27, the numeric values in the "Ma ratio of amphoteric surfactant" columns represent the mass ratio (A/I) of the content of the amphoteric surfactant to that of the inorganic salt of alkali metal in the amphoteric surfactant-containing aqueous solution.

In Tables 26 and 27, AMOGEN CB-H (30% by mass of coconut oil fatty acid amidopropyl betaine (desalted); manufactured by Dai-Ichi Kogyo Seiyaku Co., Ltd.) was used as coconut oil fatty acid amidopropyl betaine. The coconut oil fatty acid amidopropyl betaine in Examples 10-8 and 10-9 was used after water evaporation by applying heat at 80° C. to this product having a concentration of 30% by mass. In Tables 26 and 27, OBAZOLINE LB-SF (35% by mass of lauryldimethylaminoacetic acid betaine (desalted); manufactured by Toho Chemical Industry Co., Ltd.) was used as lauryldimethylaminoacetic acid betaine. In Tables 26 and 27, SOFTAZOLINE LPB-R (30% by mass of amidopropyl betaine laurate (desalted) manufactured by Kawaken Fine Chemicals Co., Ltd.) was used as amidopropyl betaine laurate. In Tables 26 and 27, the numeric values representing the content of each component represent the content of purity of the component.

<pH Change and pH Stability of Second Agent>

The second agent of the hair dye of each of Examples and Reference Examples was stored for 1 month in a thermostat bath of 45° C. Then, the pH of the second agent was measured. From the value, the value of pH change from pH 4 at the time of preparation of the second agent was determined.

In the "pH stability of second agent" columns of Tables 26 and 27, the score "5" indicates that the value of pH change is less than 0.10; the score "4" indicates that the value of pH change is 0.10 or more and less than 0.15; the score "3" indicates that the value of pH change is 0.15 or more and less than 0.20; the score "2" indicates that the value of pH change is 0.20 or more and less than 0.25; and the score "1" indicates that the value of pH change is 0.25 or more.

<Foamability>

The state of the hair dye after foaming was visually observed by expert panelists. In the "Foamability" columns of Tables 26 and 27, the score "5" indicates that the foaming is excellent; the score "4" indicates that the foaming is good; the score "3" indicates that the foaming is favorable; the score "2" indicates that the foaming is slightly insufficient; and the score "1" indicates that the foaming is insufficient or too much foaming results in low viscous, light, and large bubbles.

TABLE 25

| First agent (powdery) | |
| --- | --- |
| Ammonium sulfate | 15 |
| Sodium carbonate | 30 |
| Disodium edetate | 3 |
| Magnesium stearate | 1 |
| Toluene-2,5-diamine sulfate | 3 |
| Sodium lauryl sulfate | 5 |
| Carboxymethylcellulose | 10 |
| Sodium sulfate | Remainder |
| Total | 100 |

TABLE 26

| | | Example 10-1 | Example 10-2 | Example 10-3 | Example 10-4 | Example 10-5 | Example 10-6 | Reference Example 10-1 | Reference Example 10-2 | Reference Example 10-3 | Reference Example 10-4 |
| --- | --- | --- | --- | --- | --- | --- | --- | --- | --- | --- | --- |
| | Amphoteric surfactant-containing aqueous solution | | | | | | | | | | |
| (A) | Coconut oil fatty acid amidopropyl betaine | 30 | | | 30 | 30 | 30 | 30 | 20 | | 30 |
| (A) | Lauryldimethylaminoacetic acid betaine | | 30 | | | | | | | | |
| (A) | Amidopropyl betaine laurate | | | 30 | | | | | | | |
| (I) | Sodium chloride | 5 | 5 | 5 | | | | | | 5 | |
| (I) | Potassium chloride | | | | 5 | | | | | | |
| (I) | Sodium sulfate | | | | | 5 | | | | | |
| (I) | Disodium phosphate | | | | | | 5 | | | | |
| (I) | Sodium citrate | | | | | | | | | | 5 |
| | Purified water | Remainder | Remainder | Remainder | Remainder | Remainder | Remainder | Remainder | Remainder | Remainder | Remainder |
| | Total | 100 | 100 | 100 | 100 | 100 | 100 | 100 | 100 | 100 | 100 |
| | Second agent | | | | | | | | | | |
| (G) | 35 w/v % hydrogen peroxide | 15 | 15 | 15 | 15 | 15 | 15 | 15 | 15 | 15 | 15 |
| | The amphoteric surfactant-containing aqueous solution | 10 | 10 | 10 | 10 | 10 | 10 | 10 | 10 | 10 | 10 |
| | Cetanol | 0.5 | 0.5 | 0.5 | 0.5 | 0.5 | 0.5 | 0.5 | 0.5 | 0.5 | 0.5 |
| | Stearyl trimethyl ammonium chloride | 1 | 1 | 1 | 1 | 1 | 1 | 1 | 1 | 1 | 1 |
| | POE(5) lauryl ether | 0.5 | 0.5 | 0.5 | 0.5 | 0.5 | 0.5 | 0.5 | 0.5 | 0.5 | 0.5 |
| | Citric acid | Formulated to adjust pH to 4 | | | | | | Formulated to adjust pH to 4 | | | |
| | Purified water | Remainder | Remainder | Remainder | Remainder | Remainder | Remainder | Remainder | Remainder | Remainder | Remainder |
| | Total | 100 | 100 | 100 | 100 | 100 | 100 | 100 | 100 | 100 | 100 |
| | First agent:second agent mixing ratio (mass ratio) | 1:5 | 1:5 | 1:5 | 1:5 | 1:5 | 1:5 | 1:5 | 1:5 | 1:5 | 1:5 |
| | Mass ratio of amphoteric surfactant (A/I) | 6 | 6 | 6 | 6 | 6 | 6 | — | — | 0 | — |
| | Amount of amphoteric surfactant (A) incorporated in second agent | 3 | 3 | 3 | 3 | 3 | 3 | 3 | 2 | 0 | 3 |
| | Amount of inorganic salt of alkali metal (I) incorporated in second agent | 0.5 | 0.5 | 0.5 | 0.5 | 0.5 | 0 | 0 | 0 | 0.5 | 0 |
| | Evaluation | | | | | | | | | | |
| | pH change of second agent | 0.07 | 0.07 | 0.08 | 0.09 | 0.1 | 0.18 | 0.35 | 0.24 | 0.06 | 0.32 |
| | pH stability of second agent | 5 | 5 | 5 | 5 | 4 | 3 | 1 | 2 | 5 | 1 |
| | Foamability | 5 | 5 | 5 | 5 | 5 | 5 | 5 | 3 | 1 | 5 |

TABLE 27

| | | Example 10-7 | Example 10-8 | Example 10-9 | Example 10-10 | Example 10-11 | Example 10-12 | Example 10-13 | Example 10-14 | Example 10-15 | Example 10-16 | Example 10-17 | Example 10-18 |
|---|---|---|---|---|---|---|---|---|---|---|---|---|---|
| | Amphoteric surfactant-containing aqueous solution | | | | | | | | | | | | |
| (A) | Coconut oil fatty acid amidopropyl betaine | 20 | 35 | 40 | 25 | 25 | 25 | 25 | 25 | 25 | 25 | 25 | 25 |
| (I) | Sodium chloride | 5 | 5 | 5 | 0.5 | 1.25 | 2.5 | 3.5 | 5 | 7.5 | 10 | 12.5 | 15 |
| | Purified water | Remainder | Remainder | Remainder | Remainder | Remainder | Remainder | Remainder | Remainder | Remainder | Remainder | Remainder | Remainder |
| | Total | 100 | 100 | 100 | 100 | 100 | 100 | 100 | 100 | 100 | 100 | 100 | 100 |
| | Second agent | | | | | | | | | | | | |
| (G) | 35 w/v % hydrogen peroxide | 15 | 15 | 15 | 15 | 15 | 15 | 15 | 15 | 15 | 15 | 15 | 15 |
| | The amphoteric surfactant-containing aqueous solution | 10 | 10 | 10 | 10 | 10 | 10 | 10 | 10 | 10 | 10 | 10 | 10 |
| | Cetanol | 0.5 | 0.5 | 0.5 | 0.5 | 0.5 | 0.5 | 0.5 | 0.5 | 0.5 | 0.5 | 0.5 | 0.5 |
| | Stearyl trimethyl ammonium chloride | 1 | 1 | 1 | 1 | 1 | 1 | 1 | 1 | 1 | 1 | 1 | 1 |
| | POE(5) lauryl ether | 0.5 | 0.5 | 0.5 | 0.5 | 0.5 | 0.5 | 0.5 | 0.5 | 0.5 | 0.5 | 0.5 | 0.5 |
| | Citric acid | | | | | Formulated to adjust pH to 4 | | | | | | | |
| | Purified water | Remainder | Remainder | Remainder | Remainder | Remainder | Remainder | Remainder | Remainder | Remainder | Remainder | Remainder | Remainder |
| | Total | 100 | 100 | 100 | 100 | 100 | 100 | 100 | 100 | 100 | 100 | 100 | 100 |
| | First agent:second agent mixing ratio (mass ratio) | 1:5 | 1:5 | 1:5 | 1:5 | 1:5 | 1:5 | 1:5 | 1:5 | 1:5 | 1:5 | 1:5 | 1:5 |
| | Mass ratio of amphoteric surfactant (A/I) | 4 | 7 | 8 | 50 | 20 | 10 | 7.1 | 5 | 3.3 | 2.5 | 2 | 1.7 |
| | Amount of amphoteric surfactant (A) incorporated in second agent | 2 | 3.5 | 4 | 2.5 | 2.5 | 2.5 | 2.5 | 2.5 | 2.5 | 2.5 | 2.5 | 2.5 |
| | Amount of inorganic salt of alkali metal (I) incorporated in second agent | 0.5 | 0.5 | 0.5 | 0.05 | 0.125 | 0.25 | 0.35 | 0.5 | 0.75 | 1 | 1.25 | 1.5 |
| | Evaluation | | | | | | | | | | | | |
| | pH change of second agent | 0.07 | 0.07 | 0.08 | 0.17 | 0.15 | 0.14 | 0.09 | 0.07 | 0.07 | 0.08 | 0.15 | 0.17 |
| | pH stability of second agent | 5 | 5 | 5 | 3 | 3 | 4 | 5 | 5 | 5 | 5 | 4 | 3 |
| | Foamability | 4 | 4 | 5 | 5 | 5 | 5 | 5 | 5 | 5 | 5 | 4 | 4 |

As shown in Tables 26 and 27, the hair dyes of Examples that were constituted by formulating a (B) amphoteric surfactant and a (C) inorganic salt of alkali metal in the second agent produced favorable results for the item "pH stability".

Moreover, it was demonstrated that Reference Examples 10-1 and 10-2 containing no inorganic salt of alkali metal in the second agent were less regarded than Examples in the evaluation for the item "pH stability".

Reference Example 10-3 containing no amphoteric surfactant in the second agent produced evaluation results inferior to those of Examples in the item "foamability". When no amphoteric surfactant is used, it is difficult to obtain a favorable foamy hair dye.

Reference Example 10-4 containing sodium citrate instead of an inorganic salt of alkali metal in the second agent produced evaluation results inferior to those of Examples in the item "pH stability".

Test 10-2

An emulsion second agent containing each component shown in Tables 28 to 34 was prepared. For the second agent, an amphoteric surfactant-containing aqueous solution was first prepared by mixing the components described in each table, starting from the one at the top of the table. Next, other components were incorporated, starting from the one at the top of the table, in the amphoteric surfactant-containing aqueous solution to prepare the second agent. In Tables 28 to 34, the numeric values in the columns showing each component represent the content (unit: by mass) of the component described in the columns unless otherwise specified in the table. The numeric values of each component shown in the "Amphoteric surfactant-containing aqueous solution" column represent the content of the component in the second agent. Then, the first agent shown in Table 25 and the second agent shown in Tables 28 to 34 were mixed at a mass ratio of 1:5 and stirred using a stirring rod to prepare a foamy hair dye. The obtained hair dye was evaluated for foamability. Moreover, the obtained second agent was evaluated for pH change and pH stability. The results are shown in Tables 28 to 34.

TABLE 28

| Second agent (liquid) | Example 10-19 |
|---|---|
| Amphoteric surfactant-containing aqueous solution | |
| (A) Coconut oil fatty acid amidopropyl betaine | 2.4 |
| Purified water | 5.6 |

TABLE 28-continued

| Second agent (liquid) | Example 10-19 |
|---|---|
| (I) Sodium chloride | 0.4 |
| Cetanol | 0.5 |
| Stearyl trimethyl ammonium chloride | 1 |
| POE(5) lauryl ether | 0.5 |
| Citric acid | Formulated to adjust pH to 4 |
| Purified water | Formulated to adjust whole amount to 85% by mass |
| (G) 35 w/v % hydrogen peroxide | 15 |
| Total | 100 |
| First agent:second agent mixing ratio (mass ratio) | 1:5 |
| Content of amphoteric surfactant (A) in amphoteric surfactant-containing aqueous solution | 28.6 |
| Content of inorganic salt of alkali metal (I) in amphoteric surfactant-containing aqueous solution | 4.8 |
| Mass ratio of amphoteric surfactant (A/I) | 6 |
| Evaluation | |
| pH change of second agent | 0.07 |
| pH stability of second agent | 5 |
| Foamability | 5 |

Components were mixed starting from the one at the top of the table.

TABLE 29

| Second agent (liquid) | Example 10-20 |
|---|---|
| Amphoteric surfactant-containing aqueous solution | |
| (A) Coconut oil fatty acid amido-propyl betaine | 2.4 |
| Purified water | 9.2 |
| (I) Sodium chloride | 0.4 |
| Cetanol | 0.5 |
| Stearyl trimethyl ammonium chloride | 1 |
| POE(5) lauryl ether | 0.5 |
| Citric acid | Formulated to adjust pH to 4 |
| Purified water | Formulated to adjust whole amount to 85% by mass |
| (G) 35 w/v % hydrogen peroxide | 15 |
| Total | 100 |
| First agent:second agent mixing ratio (mass ratio) | 1:5 |
| Content of amphoteric surfactant (A) in amphoteric surfactant-containing aqueous solution | 20.0 |
| Content of inorganic salt of alkali metal (I) in amphoteric surfactant-containing aqueous solution | 3.3 |
| Mass ratio of amphoteric surfactant (A/I) | 6 |
| Evaluation | |
| pH change of second agent | 0.16 |
| pH stability of second agent | 3 |
| Foamability | 5 |

Components were mixed starting from the one at the top of the table.

TABLES 30

| Second agent (liquid) | Example 10-21 |
|---|---|
| Amphoteric surfactant-containing aqueous solution | |
| (A) Coconut oil fatty acid amido-propyl betaine | 2.4 |
| Purified water | 5.6 |
| Cetanol | 0.5 |
| (I) Sodium chloride | 0.4 |
| Stearyl trimethyl ammonium chloride | 1 |
| POE(5) lauryl ether | 0.5 |
| Citric acid | Formulated to adjust pH to 4 |
| Purified water | Formulated to adjust whole amount to 85% by mass |
| (G) 35 w/v % hydrogen peroxide | 15 |
| Total | 100 |
| First agent:second agent mixing ratio (mass ratio) | 1:5 |
| Content of amphoteric surfactant (A) in amphoteric surfactant-containing aqueous solution | 27.0 |
| Content of inorganic salt of alkali metal (I) in amphoteric surfactant-containing aqueous solution | 4.5 |
| Mass ratio of amphoteric surfactant (A/I) | 6 |
| Evaluation | |
| pH change of second agent | 0.07 |
| pH stability of second agent | 5 |
| Foamability | 5 |

Components were mixed starting from the one at the top of the table.

TABLE 31

| Second agent (liquid) | Example 10-22 |
|---|---|
| Amphoteric surfactant-containing aqueous solution | |
| (A) Coconut oil fatty acid amido-propyl betaine | 2.4 |
| Purified water | 5.6 |
| Cetanol | 0.5 |
| Stearyl trimethyl ammonium chloride | 1 |
| POE(5) lauryl ether | 0.5 |
| (I) Sodium chloride | 0.4 |
| Citric acid | Formulated to adjust pH to 4 |
| Purified water | Formulated to adjust whole amount to 85% by mass |
| (G) 35 w/v % hydrogen peroxide | 15 |
| Total | 100 |
| First agent:second agent mixing ratio (mass ratio) | 1:5 |
| Content of amphoteric surfactant (A) in amphoteric surfactant-containing aqueous solution | 23.1 |
| Content of inorganic salt of alkali metal (I) in amphoteric surfactant-containing aqueous solution | 3.8 |
| Mass ratio of amphoteric surfactant (A/I) | 6 |
| Evaluation | |
| pH change of second agent | 0.07 |
| pH stability of second agent | 5 |
| Foamability | 5 |

Components were mixed starting from the one at the top of the table.

TABLE 32

| Second agent (liquid) | Example 10-23 |
|---|---|
| Amphoteric surfactant-containing aqueous solution | |
| Purified water | 5.6 |
| (I) Sodium chloride | 0.4 |
| Cetanol | 0.5 |
| (A) Coconut oil fatty acid amidopropyl betaine | 2.4 |
| Stearyl trimethyl ammonium chloride | 1 |
| POE(5) lauryl ether | 0.5 |
| Citric acid | Formulated to adjust pH to 4 |
| Purified water | Formulated to adjust whole amount to 85% by mass |
| (G) 35 w/v % hydrogen peroxide | 15 |
| Total | 100 |
| First agent:second agent mixing ratio (mass ratio) | 1:5 |
| Content of amphoteric surfactant (A) in amphoteric surfactant-containing aqueous solution | 27.0 |
| Content of inorganic salt of alkali metal (I) in amphoteric surfactant-containing aqueous solution | 4.5 |
| Mass ratio of amphoteric surfactant (A/I) | 6 |
| Evaluation | |
| pH change of second agent | 0.08 |
| pH stability of second agent | 5 |
| Foamability | 5 |

Components were mixed starting from the one at the top of the table.

TABLE 33

| Second agent (liquid) | Example 10-24 |
|---|---|
| Amphoteric surfactant-containing aqueous solution | |
| Purified water | 5.6 |
| (I) Sodium chloride | 0.2 |
| Cetanol | 0.5 |
| (A) Coconut oil fatty acid amidopropyl betaine | 2.4 |
| Stearyl trimethyl ammonium chloride | 1 |
| POE(5) lauryl ether | 0.5 |
| Citric acid | Formulated to adjust pH to 4 |
| Purified water | Formulated to adjust whole amount to 85% by mass |
| (G) 35 w/v % hydrogen peroxide | 15 |
| Total | 100 |
| First agent:second agent mixing ratio (mass ratio) | 1:5 |
| Content of amphoteric surfactant (A) in amphoteric surfactant-containing aqueous solution | 27.6 |
| Content of inorganic salt of alkali metal (I) in amphoteric surfactant-containing aqueous solution | 2.3 |
| Mass ratio of amphoteric surfactant (A/I) | 12 |
| Evaluation | |
| pH change of second agent | 0.15 |
| pH stability of second agent | 3 |
| Foamability | 5 |

Components were mixed starting from the one at the top of the table.

TABLE 34

| Second agent (liquid) | Example 10-25 |
|---|---|
| Amphoteric surfactant-containing aqueous solution | |
| Purified water | 8.7 |
| (I) Sodium chloride | 0.4 |
| Cetanol | 0.5 |
| (A) Coconut oil fatty acid amidopropyl betaine | 2.4 |
| Stearyl trimethyl ammonium chloride | 1 |
| POE(5) lauryl ether | 0.5 |
| Citric acid | Formulated to adjust pH to 4 |
| Purified water | Formulated to adjust whole amount to 85% by mass |
| (G) 35 w/v % hydrogen peroxide | 15 |
| Total | 100 |
| First agent:second agent mixing ratio (mass ratio) | 1:5 |
| Content of amphoteric surfactant (A) in amphoteric surfactant-containing aqueous solution | 20.0 |
| Content of inorganic salt of alkali metal (I) in amphoteric surfactant-containing aqueous solution | 3.3 |
| Mass ratio of amphoteric surfactant (A/I) | 6 |
| Evaluation | |
| pH change of second agent | 0.16 |
| pH stability of second agent | 3 |
| Foamability | 5 |

Components were mixed starting from the one at the top of the table.

As shown in Tables 28 to 31, it was demonstrated that the amphoteric surfactant-containing aqueous solutions of Examples 10-19, 10-21, and 10-22 prepared by formulating approximately 2.3 parts by mass of water with respect to 1 part by mass of an amphoteric surfactant and then adding sodium chloride were better in pH stability than Example 10-20 prepared by formulating approximately 3.8 parts by mass of water with respect to 1 part by mass of an amphoteric surfactant and then adding sodium chloride.

As shown in Tables 32 to 34, it was demonstrated that the amphoteric surfactant-containing aqueous solution of Example 10-23 prepared by formulating approximately 14 parts by mass of water with respect to 1 part by mass of sodium chloride and then adding an amphoteric surfactant was better in pH stability than Examples 10-24 and 10-25 prepared by formulating approximately 20 parts by mass or more of water with respect to 1 part by mass of sodium chloride and then adding an amphoteric surfactant.

Next, technical ideas that can be grasped from the embodiments and the modifications will be described additionally below.

A hair cosmetic comprising:

a hair cosmetic composition which is applied to hair in a foamy form obtained by mixing a powdery agent and a liquid agent and foaming the mixture by shaking; and a foaming tool for mixing the powdery agent and the liquid agent and foaming the mixture by shaking.

In this case, a foamy hair cosmetic composition can be prepared easily.

REFERENCE SIGNS LIST

10: hair bleach/hair dye remover, 11: first agent, 12: second agent, 13: mixture, 14: foamy hair bleach/hair dye remover, 20: container, 21: main body of the container, 22: lid.

The invention claimed is:

1. A hair cosmetic composition constituted as a hair dye or a hair bleach/hair dye remover comprising a plurality of agents, wherein the plurality of agents comprise a powdery first agent and a liquid second agent, wherein the powdery first agent comprises an alkali agent nonionic polymer, thickener and an anionic surfactant, and wherein the liquid second agent comprises hydrogen peroxide an amphoteric surfactant, cationic polymer and a cationic surfactant, and further wherein the hair cosmetic composition is applied to hair in a foamy form obtained by mixing the powdery first agent and the liquid second agent and foaming the mixture by shaking.

2. The hair cosmetic composition according to claim 1, wherein the cationic surfactant contains at least one of: (i) an ammonium cationic surfactant having an alkyl group with a number of carbon atoms in a range of from 16 to 22 and (ii) an ammonium cationic surfactant having an alkyl group with a number of carbon atoms in a range of from 10 to 16.

3. The hair cosmetic composition according to claim 1, wherein the liquid second agent further contains phenoxyethanol and at least one selected from the group consisting of benzoic acid and benzoates.

4. The hair cosmetic composition according to claim 1, wherein
the alkali agent is carbonate,
the hair cosmetic composition further contains 1 to 5% by mass of a chelating agent, and
the mass ratio of the content of the carbonate in the hair cosmetic composition to that of the chelating agent in the hair cosmetic composition is 0.02 to 6.5.

5. A method for using the hair cosmetic composition according to claim 1, comprising:
forming the hair cosmetic composition in a foamy form by mixing the powdery first agent and the liquid second agent in the hair cosmetic composition and foaming the mixture by shaking; and
applying the obtained hair cosmetic composition in a foamy form to hair by hand.

* * * * *